(12) United States Patent
Pomerantz et al.

(10) Patent No.: US 11,993,791 B2
(45) Date of Patent: *May 28, 2024

(54) MODIFICATION OF 3' TERMINAL ENDS OF NUCLEIC ACIDS BY DNA POLYMERASE THETA

(71) Applicant: Temple University-Of The Commonwealth System of Higher Education, Philadelphia, PA (US)

(72) Inventors: Richard T. Pomerantz, Brooklyn, NY (US); Tatiana Kent, Philadelphia, PA (US)

(73) Assignee: Temple University-Of The Commonwealth System of Higher Education, Philadelphia, PA (US)

(*) Notice: Subject to any disclaimer, the term of this patent is extended or adjusted under 35 U.S.C. 154(b) by 568 days.

This patent is subject to a terminal disclaimer.

(21) Appl. No.: 17/120,973

(22) Filed: Dec. 14, 2020

(65) Prior Publication Data

US 2021/0171920 A1 Jun. 10, 2021

Related U.S. Application Data

(63) Continuation of application No. 15/772,192, filed as application No. PCT/US2016/059419 on Oct. 28, 2016, now Pat. No. 10,865,396.

(60) Provisional application No. 62/338,119, filed on May 18, 2016, provisional application No. 62/248,083, filed on Oct. 29, 2015.

(51) Int. Cl.
| | |
|---|---|
| *C12N 9/12* | (2006.01) |
| *C07H 21/04* | (2006.01) |
| *C12P 19/34* | (2006.01) |
| *C12Q 1/68* | (2018.01) |
| *C12Q 1/6806* | (2018.01) |
| *C12Q 1/6827* | (2018.01) |
| *C12Q 1/6844* | (2018.01) |
| *C12Q 1/6853* | (2018.01) |

(52) U.S. Cl.
CPC ............ *C12N 9/1252* (2013.01); *C12P 19/34* (2013.01); *C12Q 1/68* (2013.01); *C12Q 1/6806* (2013.01); *C12Q 1/6827* (2013.01); *C12Q 1/6844* (2013.01); *C12Q 1/6853* (2013.01); *C07H 21/04* (2013.01); *C12N 2310/344* (2013.01); *C12Q 2521/101* (2013.01); *C12Q 2525/101* (2013.01); *C12Q 2563/137* (2013.01); *C12Y 207/07007* (2013.01)

(58) Field of Classification Search
CPC .. C12N 9/1252; C12N 2310/344; C12Q 1/68; C12Q 1/6806; C12Q 1/6853; C12Q 2521/101; C12Q 2525/101; C12Q 2563/137

USPC ...................... 435/6.1, 91.1, 91.31
See application file for complete search history.

(56) References Cited

U.S. PATENT DOCUMENTS

| | | | |
|---|---|---|---|
| 10,865,396 B2* | 12/2020 | Pomerantz | C12Q 1/68 |
| 2005/0032177 A1* | 2/2005 | Hogrefe | C12N 15/102 |
| | | | 435/91.2 |
| 2009/0075378 A1* | 3/2009 | Horlick | C07K 16/461 |
| | | | 435/254.2 |
| 2011/0275523 A1* | 11/2011 | Quake | C12Q 1/68 |
| | | | 435/6.1 |

FOREIGN PATENT DOCUMENTS

| | | | |
|---|---|---|---|
| WO | 2004007773 A1 | 1/2004 | |
| WO | 2004072238 A2 | 8/2004 | |
| WO | WO 2103/074632 | * 5/2013 | ............ C12Q 1/68 |

OTHER PUBLICATIONS

Tabor et al (Proc. Natl. Acad. Sci, vol. 86, pp. 407604080 (1989)) (Year: 1989).*
Arana et al (Nucleic Acids Res., vol. 36, No. 11, pp. 3847-3856 (2008)) (Year: 2008).*
Hogg et al.(Nucl. Acids Res., vol. 40, No. 6, pp. 2611-2622 (publ. online Dec. 1, 2011) (Year: 2011).*
Extended European Search Report for Application No. 16860925.3, dated May 29, 2019, 8 pages.
Samuel Black et al: "DNA Polymerase [theta]: A Unique Multifunctional End-Joining Machine", GENES, vol. 7, No. 9, Sep. 21, 2016 (Sep. 21, 2016), p. 67, XP055590016, DOI: 10.3390/genes7090067.
Hayley J. Schultz et al: "Taq DNA Polymerase Mutants and 2'-Modified Sugar Recognition", Biochemistry, vol. 54, No. 38, Sep. 29, 2015 (Sep. 29, 2015), pp. 5999-6008, XP055590034, ISSN: 0006-2960, DOI: 10.1021/acs.biochem.5b00689.
Khandazhinskaya, Anastasiya L., et al. "New substrates of terminal deoxynucleotidyl transferase: synthesis and biological evaluation." Collection of Czechoslovak Chemical Communications 5 (2016): 344-347.
Sale, Julian E., Alan R. Lehmann, and Roger Woodgate. "Y-family DNA polymerases and their role in tolerance of cellular DNA damage." Nature reviews Molecular cell biology 13.3 (2012): 141-152.
Waters, Lauren S., et al. "Eukaryotic translesion polymerases and their roles and regulation in DNA damage tolerance." Microbiol. Mol. Biol. Rev. 73.1 (2009): 134-154.

(Continued)

*Primary Examiner* — Jane J Zara
(74) *Attorney, Agent, or Firm* — Riverside Law LLP

(57) ABSTRACT

The invention provides compositions and methods for modifying the 3'-terminal ends of nucleic acids using DNA polymerase θ terminal transferase activity.

27 Claims, 58 Drawing Sheets
Specification includes a Sequence Listing.

(56) References Cited

OTHER PUBLICATIONS

Kent, Tatiana, et al. "Mechanism of microhomology-mediated end-joining promoted by human DNA polymerase θ." Nature structural & molecular biology 22.3 (2015): 230-237.
Yoon, Jung-Hoon, et al. "A role for DNA polymerase θ in promoting replication through oxidative DNA lesion, thymine glycol, in human cells." Journal of Biological Chemistry 289.19 (2014): 13177-13185.
Yousefzadeh, Matthew J., et al. "Mechanism of suppression of chromosomal instability by DNA polymerase POLQ." PLoS genetics 10.10 (2014): e1004654, 15 pages.
Mateos-Gomez, Pedro A., et al. "Mammalian polymerase θ promotes alternative NHEJ and suppresses recombination." Nature 518.7538 (2015): 254-257.
Hogg, Matthew, et al. "Lesion bypass activity of DNA polymerase e (POLQ) is an intrinsic property of the pol domain and depends on unique sequence inserts." Journal of molecular biology 405.3 (2011): 642-652.
Seki, Mineaki, Federica Marini, and Richard D. Wood. "POLQ (Pol θ), a DNA polymerase and DNA☐ dependent ATPase in human cells." Nucleic acids research 31.21 (2003): 6117-6126.
Chan, Sze Ham, Amy Marie Yu, and Mitch McVey. "Dual roles for DNA polymerase theta in alternative end-joining repair of double-strand breaks in *Drosophila*." PLoS genetics 6.7 (2010): e1001005.
Koole, Wouter, et al. "A Polymerase Theta-dependent repair pathway suppresses extensive genomic instability at endogenous G4 DNA sites." Nature communications 5.1 (2014): 3216.
Zahn, Karl E., et al. "Human DNA polymerase θ grasps the primer terminus to mediate DNA repair." Nature structural & molecular biology 22.4 (2015): 304-311.
Domínguez, Orlando, et al. "DNA polymerase mu (Pol µ), homologous to TdT, could act as a DNA mutator in eukaryotic cells." The EMBO journal 19.7 (2000): 1731-1742.
McElhinny, Stephanie A. Nick, and Dale A. Ramsden. "Polymerase mu is a DNA-directed DNA/RNA polymerase." Molecular and cellular biology 23.7 (2003): 2309-2315.
Motea, Edward A., and Anthony J. Berdis. "Terminal deoxynucleotidyl transferase: the story of a misguided DNA polymerase." Biochimica et Biophysica Acta (BBA)-Proteins and Proteomics 1804.5 (2010): 1151-1166.
Martin, Maria Jose, et al. "Ribonucleotides and manganese ions improve non-homologous end joining by human Polµ." Nucleic acids research 41.4 (2013): 2428-2436.
Walmacq, Celine, et al. "Rpb9 subunit controls transcription fidelity by delaying NTP sequestration in RNA polymerase II." Journal of Biological Chemistry 284.29 (2009): 19601-19612.
MacDermott, M. A. R. Y. "The intracellular concentration of free magnesium in extensor digitorum longus muscles of the rat." Experimental Physiology: Translation and Integration 75.6 (1990): 763-769.
Andrade, Paula, et al. "Limited terminal transferase in human DNA polymerase µ defines the required balance between accuracy and efficiency in NHEJ." Proceedings of the National Academy of Sciences 106.38 (2009): 16203-16208.
Schmitz, Carsten, et al. "Regulation of vertebrate cellular Mg2+ homeostasis by TRPM7." Cell 114.2 (2003): 191-200.
Visser, Daan, et al. "Function and regulation of the channel-kinase TRPM7 in health and disease." European journal of cell biology 93.10-12 (2014): 455-465.

Lee-Theilen, Mieun, et al. "CtIP promotes microhomology-mediated alternative end joining during class-switch recombination." Nature structural & molecular biology 18.1 (2011): 75-79.
Truong, Lan N., et al. "Microhomology-mediated End Joining and Homologous Recombination share the initial end resection step to repair DNA double-strand breaks in mammalian cells." Proceedings of the National Academy of Sciences 110.19 (2013): 7720-7725.
Zhang, Yu, and Maria Jasin. "An essential role for CtIP in chromosomal translocation formation through an alternative end-joining pathway." Nature structural & molecular biology 18.1 (2011): 80-84.
Audebert, Marc, Bernard Salles, and Patrick Calsou. "Involvement of poly (ADP-ribose) polymerase-1 and XRCC1/DNA ligase III in an alternative route for DNA double-strand breaks rejoining." Journal of Biological Chemistry 279.53 (2004): 55117-55126.
Simsek, Deniz, et al. "DNA ligase III promotes alternative nonhomologous end-joining during chromosomal translocation formation." PLoS genetics 7.6 (2011): e1002080.
Brissett, Nigel C., et al. "Structure of a NHEJ polymerase-mediated DNA synaptic complex." Science 318.5849 (2007): 456-459.
Ceccaldi, Raphael, et al. "Homologous-recombination-deficient tumours are dependent on Polθ-mediated repair." Nature 518.7538 (2015): 258-262.
Higgins, Geoff S., et al. "Overexpression of POLQ confers a poor prognosis in early breast cancer patients." Oncotarget 1.3 (2010): 175-184.
Lemée, Fanny, et al. "DNA polymerase θ up-regulation is associated with poor survival in breast cancer, perturbs DNA replication, and promotes genetic instability." Proceedings of the National Academy of Sciences 107.30 (2010): 13390-13395.
Trujillo, Kelly M., et al. "Nuclease activities in a complex of human recombination and DNA repair factors Rad50, Mre11, and p95." Journal of Biological Chemistry 273.34 (1998): 21447-21450.
Cannavo, Elda, and Petr Cejka. "Sae2 promotes dsDNA endonuclease activity within Mre11-Rad50-Xrs2 to resect DNA breaks." Nature 514.7520 (2014): 122-125.
Van Schendel, Robin, et al. "Polymerase Θ is a key driver of genome evolution and of CRISPR/Cas9-mediated mutagenesis." Nature communications 6.1 (2015): 7394.
Thomas, Crystal, et al. "One-step enzymatic modification of RNA 3' termini using polymerase θ." Nucleic acids research 47.7 (2019): 3272-3283.
ISR and Written Opinion PCT/US2016/059419.
Foti JJ et al., "SnapShot: DNA polymerases I prokaryotes", Cell, 2010, 141:191-192.
Lange SS et al., "DNA polymerases and cancer", Nature reviews Cancer, 2011, 11:96-110.
Seki M et al., "High-efficiency bypass of DNA damage by human DNA polymerase Q", EMBO J, 2004, 23:4484-4494.
Arana ME et al., "Low-fidelity DNA synthesis by human DNA polymerase theta", Nucleic Acids Res., 2008, 36:3847-3856.
Tabor S et al., "Effect of manganese ions on the incorporation of dideoxynucleotides by bacteriophage T7 DNA polymerase and *Escherichia coli* DNA polymerase I" Proc. Natl. Acad. Sci, 1989, 86:4076-4080.
Hogg M et al., "Promiscuous DNA synthesis by human DNA polymerase theta.", Nucl Acids Res., 2012, 10:2611-2622.
Lahiri et al., 2013, "Kinetic Characterization of Exonuclease-Deficient *Staphylococcus aureus* PoIC, a C-family Replicative DNA Polymerase", PLOS ONE, 8:e63489.

* cited by examiner

SEQUENCE LISTING

```
<160> NUMBER OF SEQ ID NOS: 32

<210> SEQ ID NO 1
<211> LENGTH: 799
<212> TYPE: PRT
<213> ORGANISM: Homo sapiens

<400> SEQUENCE: 1

Gly Phe Lys Asp Asn Ser Pro Ile Ser Asp Thr Ser Phe Ser Leu Gln
1               5                   10                  15

Leu Ser Gln Asp Gly Leu Gln Leu Thr Pro Ala Ser Ser Ser Ser Glu
            20                  25                  30

Ser Leu Ser Ile Ile Asp Val Ala Ser Asp Gln Asn Leu Phe Gln Thr
        35                  40                  45

Phe Ile Lys Glu Trp Arg Cys Lys Lys Arg Phe Ser Ile Ser Leu Ala
    50                  55                  60

Cys Glu Lys Ile Arg Ser Leu Thr Ser Ser Lys Thr Ala Thr Ile Gly
65                  70                  75                  80

Ser Arg Phe Lys Gln Ala Ser Ser Pro Gln Glu Ile Pro Ile Arg Asp
                85                  90                  95

Asp Gly Phe Pro Ile Lys Gly Cys Asp Asp Thr Leu Val Val Gly Leu
            100                 105                 110

Ala Val Cys Trp Gly Gly Arg Asp Ala Tyr Tyr Phe Ser Leu Gln Lys
        115                 120                 125

Glu Gln Lys His Ser Glu Ile Ser Ala Ser Leu Val Pro Pro Ser Leu
    130                 135                 140

Asp Pro Ser Leu Thr Leu Lys Asp Arg Met Trp Tyr Leu Gln Ser Cys
145                 150                 155                 160

Leu Arg Lys Glu Ser Asp Lys Glu Cys Ser Val Val Ile Tyr Asp Phe
                165                 170                 175

Ile Gln Ser Tyr Lys Ile Leu Leu Leu Ser Cys Gly Ile Ser Leu Glu
            180                 185                 190

Gln Ser Tyr Glu Asp Pro Lys Val Ala Cys Trp Leu Leu Asp Pro Asp
        195                 200                 205

Ser Gln Glu Pro Thr Leu His Ser Ile Val Thr Ser Phe Leu Pro His
    210                 215                 220

Glu Leu Pro Leu Leu Glu Gly Met Glu Thr Ser Gln Gly Ile Gln Ser
225                 230                 235                 240

Leu Gly Leu Asn Ala Gly Ser Glu His Ser Gly Arg Tyr Arg Ala Ser
```

```
            245                 250                 255

Val Glu Ser Ile Leu Ile Phe Asn Ser Met Asn Gln Leu Asn Ser Leu
            260                 265                 270

Leu Gln Lys Glu Asn Leu Gln Asp Val Phe Arg Lys Val Glu Met Pro
            275                 280                 285

Ser Gln Tyr Cys Leu Ala Leu Leu Glu Leu Asn Gly Ile Gly Phe Ser
            290                 295                 300

Thr Ala Glu Cys Glu Ser Gln Lys His Ile Met Gln Ala Lys Leu Asp
305                 310                 315                 320

Ala Ile Glu Thr Gln Ala Tyr Gln Leu Ala Gly His Ser Phe Ser Phe
                325                 330                 335

Thr Ser Ser Asp Asp Ile Ala Glu Val Leu Phe Leu Glu Leu Lys Leu
            340                 345                 350

Pro Pro Asn Arg Glu Met Lys Asn Gln Gly Ser Lys Lys Thr Leu Gly
            355                 360                 365

Ser Thr Arg Arg Gly Ile Asp Asn Gly Arg Lys Leu Arg Leu Gly Arg
            370                 375                 380

Gln Phe Ser Thr Ser Lys Asp Val Leu Asn Lys Leu Lys Ala Leu His
385                 390                 395                 400

Pro Leu Pro Gly Leu Ile Leu Glu Trp Arg Arg Ile Thr Asn Ala Ile
                405                 410                 415

Thr Lys Val Val Phe Pro Leu Gln Arg Glu Lys Cys Leu Asn Pro Phe
            420                 425                 430

Leu Gly Met Glu Arg Ile Tyr Pro Val Ser Gln Ser His Thr Ala Thr
            435                 440                 445

Gly Arg Ile Thr Phe Thr Glu Pro Asn Ile Gln Asn Val Pro Arg Asp
            450                 455                 460

Phe Glu Ile Lys Met Pro Thr Leu Val Gly Ser Pro Pro Ser Gln
465                 470                 475                 480

Ala Val Gly Lys Gly Leu Leu Pro Met Gly Arg Gly Lys Tyr Lys Lys
                485                 490                 495

Gly Phe Ser Val Asn Pro Arg Cys Gln Ala Gln Met Glu Glu Arg Ala
            500                 505                 510

Ala Asp Arg Gly Met Pro Phe Ser Ile Ser Met Arg His Ala Phe Val
            515                 520                 525

Pro Phe Pro Gly Gly Ser Ile Leu Ala Ala Asp Tyr Ser Gln Leu Glu
            530                 535                 540

Leu Arg Ile Leu Ala His Leu Ser His Asp Arg Arg Leu Ile Gln Val
545                 550                 555                 560

Leu Asn Thr Gly Ala Asp Val Phe Arg Ser Ile Ala Ala Glu Trp Lys
                565                 570                 575

Met Ile Glu Pro Glu Ser Val Gly Asp Leu Arg Gln Gln Ala Lys
            580                 585                 590

Gln Ile Cys Tyr Gly Ile Ile Tyr Gly Met Gly Ala Lys Ser Leu Gly
            595                 600                 605

Glu Gln Met Gly Ile Lys Glu Asn Asp Ala Ala Cys Tyr Ile Asp Ser
            610                 615                 620

Phe Lys Ser Arg Tyr Thr Gly Ile Asn Gln Phe Met Thr Glu Thr Val
625                 630                 635                 640

Lys Asn Cys Lys Arg Asp Gly Phe Val Gln Thr Ile Leu Gly Arg Arg
                645                 650                 655

Arg Tyr Leu Pro Gly Ile Lys Asp Asn Asn Pro Tyr Arg Lys Ala His
            660                 665                 670
```

```
Ala Glu Arg Gln Ala Ile Asn Thr Ile Val Gln Gly Ser Ala Ala Asp
        675                 680                 685

Ile Val Lys Ile Ala Thr Val Asn Ile Gln Lys Gln Leu Glu Thr Phe
690                 695                 700

His Ser Thr Phe Lys Ser His Gly His Arg Glu Gly Met Leu Gln Ser
705                 710                 715                 720

Asp Gln Thr Gly Leu Ser Arg Lys Arg Lys Leu Gln Gly Met Phe Cys
                725                 730                 735

Pro Ile Arg Gly Gly Phe Phe Ile Leu Gln Leu His Asp Glu Leu Leu
            740                 745                 750

Tyr Glu Val Ala Glu Glu Asp Val Val Gln Val Ala Gln Ile Val Lys
        755                 760                 765

Asn Glu Met Glu Ser Ala Val Lys Leu Ser Val Lys Leu Lys Val Lys
    770                 775                 780

Val Lys Ile Gly Ala Ser Trp Gly Glu Leu Lys Asp Phe Asp Val
785                 790                 795

<210> SEQ ID NO 2
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 2
gcgggagaaa tggatatgaa                                            20

<210> SEQ ID NO 3
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 3
ttgacgcctt ccttcttctg                                            20

<210> SEQ ID NO 4
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 4
aacctttgaa aaagcccaca                                            20

<210> SEQ ID NO 5
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 5
gcacgtttcc gacttgagtt                                            20

<210> SEQ ID NO 6
<211> LENGTH: 20
<212> TYPE: DNA
<213> ORGANISM: Artificial Sequence
<220> FEATURE:
```

<223> OTHER INFORMATION: Chemically Synthesized

<400> SEQUENCE: 6
ggcggatcac aagcaataat                                                    20

<210> SEQ ID NO 7
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 7
ctgccattcc agagattggt                                                    20

<210> SEQ ID NO 8
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 8
agccacagtg ctcacatcac                                                    20

<210> SEQ ID NO 9
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 9
tcccaaagtc gctctgagtt                                                    20

<210> SEQ ID NO 10
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 10
cacagattct ggcaggctgc agatcgc                                            27

<210> SEQ ID NO 11
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 11
cacagattct ggcaggctgc agatcgc                                            27

<210> SEQ ID NO 12
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 12
cactgtgagc ttagggttag agatac                                             26

<210> SEQ ID NO 13
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 13
cactgtgagc ttagggttag agccgg                                      26

<210> SEQ ID NO 14
<211> LENGTH: 37
<212> TYPE: DNA
<213> ORGANISM: Artificial Sequence
<220> FEATURE:
<223> OTHER INFORMATION: Chemically Synthesized

<400> SEQUENCE: 14
cgaaatagac agatcgctga ggataggtgc ctcactg                          37

<210> SEQ ID NO 15
<211> LENGTH: 37
<212> TYPE: DNA
<213> ORGANISM: Artificial Sequence
<220> FEATURE:
<223> OTHER INFORMATION: Chemically Synthesized

<400> SEQUENCE: 15
cagtgaggca cctatcctca gcgatctgtc tatttcg                          37

<210> SEQ ID NO 16
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 16
catcttttac ttccaccagc gtttctggg                                   29

<210> SEQ ID NO 17
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 17
cccagaaacg ctggtggaag taaaagatg                                   29

<210> SEQ ID NO 18
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 18
gtggatgaat tacacatgct gggagactc                                   29

<210> SEQ ID NO 19
<211> LENGTH: 29
<212> TYPE: DNA
<213> ORGANISM: Artificial Sequence
<220> FEATURE:
<223> OTHER INFORMATION: Chemically Synthesized

```
<400> SEQUENCE: 19
gagtctccca gcatgtgtaa ttcatccac                                    29

<210> SEQ ID NO 20
<211> LENGTH: 37
<212> TYPE: DNA
<213> ORGANISM: Artificial Sequence
<220> FEATURE:
<223> OTHER INFORMATION: Chemically Synthesized

<400> SEQUENCE: 20
actgtgagct tagggttagg gttagggtta gggttag                           37

<210> SEQ ID NO 21
<211> LENGTH: 36
<212> TYPE: DNA
<213> ORGANISM: Artificial Sequence
<220> FEATURE:
<223> OTHER INFORMATION: Chemically Synthesized

<400> SEQUENCE: 21
ggaggttagg cactgtgagc ttagggttag agatac                            36

<210> SEQ ID NO 22
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 22
ctaagctcac agtgcctaac ctcc                                         24

<210> SEQ ID NO 23
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 23
gagcacgtcc aggcgatctg cagcctg                                      27

<210> SEQ ID NO 24
<211> LENGTH: 39
<212> TYPE: DNA
<213> ORGANISM: Artificial Sequence
<220> FEATURE:
<223> OTHER INFORMATION: Chemically Synthesized

<400> SEQUENCE: 24
gagcacgtcc aggcgatctg cagcctgcca gaatctgtg                         39

<210> SEQ ID NO 25
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 25
cactgtgagc ttagggttag agatac                                       26

<210> SEQ ID NO 26
<211> LENGTH: 45
```

```
<212> TYPE: DNA
<213> ORGANISM: Artificial Sequence
<220> FEATURE:
<223> OTHER INFORMATION: Chemically Synthesized

<400> SEQUENCE: 26
tttttttttt tttttttgc gatctgcagc ctgccagaat ctgtg         45

<210> SEQ ID NO 27
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 27
cactgtgagc ttagggttag agatcg                              26

<210> SEQ ID NO 28
<211> LENGTH: 9
<212> TYPE: DNA
<213> ORGANISM: Artificial Sequence
<220> FEATURE:
<223> OTHER INFORMATION: Chemically Synthesized

<400> SEQUENCE: 28 aucgagagg                                                  9

<210> SEQ ID NO 29
<211> LENGTH: 14
<212> TYPE: DNA
<213> ORGANISM: Artificial Sequence
<220> FEATURE:
<223> OTHER INFORMATION: Chemically Synthesized

<400> SEQUENCE: 29
ctaagctcac agtg                                           14

<210> SEQ ID NO 30
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 30
cgccacctct gacttgagcg                                     20

<210> SEQ ID NO 31
<211> LENGTH: 39
<212> TYPE: DNA
<213> ORGANISM: Artificial Sequence
<220> FEATURE:
<223> OTHER INFORMATION: Chemically Synthesized

<400> SEQUENCE: 31
gagcacgtcc acgcgatctg cagcctgcca gaatctgtg                39

<210> SEQ ID NO 32
<211> LENGTH: 2397
<212> TYPE: PRT
<213> ORGANISM: Homo sapiens

<400> SEQUENCE: 32

Gly Gly Asn Thr Thr Tyr Ala Ala Arg Gly Ala Tyr Ala Ala Tyr Trp
1               5                   10                  15
```

```
Ser Asn Cys Cys Asn Ala Thr His Trp Ser Asn Gly Ala Tyr Ala Cys
            20                  25                  30

Asn Trp Ser Asn Thr Thr Tyr Trp Ser Asn Tyr Thr Asn Cys Ala Arg
        35                  40                  45

Tyr Thr Asn Trp Ser Asn Cys Ala Arg Gly Ala Tyr Gly Gly Asn Tyr
    50                  55                  60

Thr Asn Cys Ala Arg Tyr Thr Asn Ala Cys Asn Cys Cys Asn Gly Cys
65                  70                  75                  80

Asn Trp Ser Asn Trp Ser Asn Trp Ser Asn Trp Ser Asn Gly Ala Arg
                85                  90                  95

Trp Ser Asn Tyr Thr Asn Trp Ser Asn Ala Thr His Ala Thr His Gly
            100                 105                 110

Ala Tyr Gly Thr Asn Gly Cys Asn Trp Ser Asn Gly Ala Tyr Cys Ala
        115                 120                 125

Arg Ala Ala Tyr Tyr Thr Asn Thr Thr Tyr Cys Ala Arg Ala Cys Asn
    130                 135                 140

Thr Thr Tyr Ala Thr His Ala Ala Arg Gly Ala Arg Thr Gly Gly Met
145                 150                 155                 160

Gly Asn Thr Gly Tyr Ala Ala Arg Ala Ala Arg Met Gly Asn Thr Thr
                165                 170                 175

Tyr Trp Ser Asn Ala Thr His Trp Ser Asn Tyr Thr Asn Gly Cys Asn
            180                 185                 190

Thr Gly Tyr Gly Ala Arg Ala Ala Arg Ala Thr His Met Gly Asn Trp
        195                 200                 205

Ser Asn Tyr Thr Asn Ala Cys Asn Trp Ser Asn Trp Ser Asn Ala Ala
    210                 215                 220

Arg Ala Cys Asn Gly Cys Asn Ala Cys Asn Ala Thr His Gly Gly Asn
225                 230                 235                 240

Trp Ser Asn Met Gly Asn Thr Thr Tyr Ala Ala Arg Cys Ala Arg Gly
                245                 250                 255

Cys Asn Trp Ser Asn Trp Ser Asn Cys Cys Asn Cys Ala Arg Gly Ala
            260                 265                 270

Arg Ala Thr His Cys Cys Asn Ala Thr His Met Gly Asn Gly Ala Tyr
        275                 280                 285

Gly Ala Tyr Gly Gly Asn Thr Thr Tyr Cys Cys Asn Ala Thr His Ala
    290                 295                 300

Ala Arg Gly Gly Asn Thr Gly Tyr Gly Ala Tyr Gly Ala Tyr Ala Cys
305                 310                 315                 320

Asn Tyr Thr Asn Gly Thr Asn Gly Thr Asn Gly Gly Asn Tyr Thr Asn
                325                 330                 335

Gly Cys Asn Gly Thr Asn Thr Gly Tyr Thr Gly Gly Gly Gly Asn Gly
            340                 345                 350

Gly Asn Met Gly Asn Gly Ala Tyr Gly Cys Asn Thr Ala Tyr Thr Ala
        355                 360                 365

Tyr Thr Thr Tyr Trp Ser Asn Tyr Thr Asn Cys Ala Arg Ala Ala Arg
    370                 375                 380

Gly Ala Arg Cys Ala Arg Ala Ala Arg Cys Ala Tyr Trp Ser Asn Gly
385                 390                 395                 400

Ala Arg Ala Thr His Trp Ser Asn Gly Cys Asn Trp Ser Asn Tyr Thr
                405                 410                 415

Asn Gly Thr Asn Cys Cys Asn Cys Cys Asn Trp Ser Asn Tyr Thr Asn
            420                 425                 430
```

-continued

```
Gly Ala Tyr Cys Cys Asn Trp Ser Asn Tyr Thr Asn Ala Cys Asn Tyr
            435                 440                 445

Thr Asn Ala Ala Arg Gly Ala Tyr Met Gly Asn Ala Thr Gly Thr Gly
450                 455                 460

Gly Thr Ala Tyr Tyr Thr Asn Cys Ala Arg Trp Ser Asn Thr Gly Tyr
465                 470                 475                 480

Tyr Thr Asn Met Gly Asn Ala Ala Arg Gly Ala Arg Trp Ser Asn Gly
                485                 490                 495

Ala Tyr Ala Ala Arg Gly Ala Arg Thr Gly Tyr Trp Ser Asn Gly Thr
            500                 505                 510

Asn Gly Thr Asn Ala Thr His Thr Ala Tyr Gly Ala Tyr Thr Thr Tyr
        515                 520                 525

Ala Thr His Cys Ala Arg Trp Ser Asn Thr Ala Tyr Ala Ala Arg Ala
    530                 535                 540

Thr His Tyr Thr Asn Tyr Thr Asn Tyr Thr Asn Trp Ser Asn Thr Gly
545                 550                 555                 560

Tyr Gly Gly Asn Ala Thr His Trp Ser Asn Tyr Thr Asn Gly Ala Arg
                565                 570                 575

Cys Ala Arg Trp Ser Asn Thr Ala Tyr Gly Ala Arg Gly Ala Tyr Cys
            580                 585                 590

Cys Asn Ala Ala Arg Gly Thr Asn Gly Cys Asn Thr Gly Tyr Thr Gly
        595                 600                 605

Gly Tyr Thr Asn Tyr Thr Asn Gly Ala Tyr Cys Cys Asn Gly Ala Tyr
    610                 615                 620

Trp Ser Asn Cys Ala Arg Gly Ala Arg Cys Cys Asn Ala Cys Asn Tyr
625                 630                 635                 640

Thr Asn Cys Ala Tyr Trp Ser Asn Ala Thr His Gly Thr Asn Ala Cys
                645                 650                 655

Asn Trp Ser Asn Thr Thr Tyr Tyr Thr Asn Cys Cys Asn Cys Ala Tyr
            660                 665                 670

Gly Ala Arg Tyr Thr Asn Cys Cys Asn Tyr Thr Asn Tyr Thr Asn Gly
        675                 680                 685

Ala Arg Gly Gly Asn Ala Thr Gly Gly Ala Arg Ala Cys Asn Trp Ser
    690                 695                 700

Asn Cys Ala Arg Gly Gly Asn Ala Thr His Cys Ala Arg Trp Ser Asn
705                 710                 715                 720

Tyr Thr Asn Gly Gly Asn Tyr Thr Asn Ala Ala Tyr Gly Cys Asn Gly
                725                 730                 735

Gly Asn Trp Ser Asn Gly Ala Arg Cys Ala Tyr Trp Ser Asn Gly Gly
            740                 745                 750

Asn Met Gly Asn Thr Ala Tyr Met Gly Asn Gly Cys Asn Trp Ser Asn
        755                 760                 765

Gly Thr Asn Gly Ala Arg Trp Ser Asn Ala Thr His Tyr Thr Asn Ala
    770                 775                 780

Thr His Thr Thr Tyr Ala Ala Tyr Trp Ser Asn Ala Thr Gly Ala Ala
785                 790                 795                 800

Tyr Cys Ala Arg Tyr Thr Asn Ala Ala Tyr Trp Ser Asn Tyr Thr Asn
                805                 810                 815

Tyr Thr Asn Cys Ala Arg Ala Ala Arg Gly Ala Arg Ala Ala Tyr Tyr
            820                 825                 830

Thr Asn Cys Ala Arg Gly Ala Tyr Gly Thr Asn Thr Thr Tyr Met Gly
        835                 840                 845

Asn Ala Ala Arg Gly Thr Asn Gly Ala Arg Ala Thr Gly Cys Cys Asn
```

-continued

```
    850                 855                 860

Trp Ser Asn Cys Ala Arg Thr Ala Tyr Thr Gly Tyr Tyr Thr Asn Gly
865                 870                 875                 880

Cys Asn Tyr Thr Asn Tyr Thr Asn Gly Ala Arg Tyr Thr Asn Ala Ala
                885                 890                 895

Tyr Gly Gly Asn Ala Thr His Gly Gly Asn Thr Thr Tyr Trp Ser Asn
            900                 905                 910

Ala Cys Asn Gly Cys Asn Gly Ala Arg Thr Gly Tyr Gly Ala Arg Trp
        915                 920                 925

Ser Asn Cys Ala Arg Ala Ala Arg Cys Ala Tyr Ala Thr His Ala Thr
    930                 935                 940

Gly Cys Ala Arg Gly Cys Asn Ala Ala Arg Tyr Thr Asn Gly Ala Tyr
945                 950                 955                 960

Gly Cys Asn Ala Thr His Gly Ala Arg Ala Cys Asn Cys Ala Arg Gly
                965                 970                 975

Cys Asn Thr Ala Tyr Cys Ala Arg Tyr Thr Asn Gly Cys Asn Gly Gly
            980                 985                 990

Asn Cys Ala Tyr Trp Ser Asn Thr  Thr Tyr Trp Ser Asn  Thr Thr Tyr
        995                 1000                1005

Ala Cys  Asn Trp Ser Asn Trp  Ser Asn Gly Ala Tyr  Gly Ala Tyr
    1010                 1015                 1020

Ala Thr  His Gly Cys Asn Gly  Ala Arg Gly Thr Asn  Tyr Thr Asn
    1025                 1030                 1035

Thr Thr  Tyr Tyr Thr Asn Gly  Ala Arg Tyr Thr Asn  Ala Ala Arg
    1040                 1045                 1050

Tyr Thr  Asn Cys Cys Asn Cys  Cys Asn Ala Ala Tyr  Met Gly Asn
    1055                 1060                 1065

Gly Ala  Arg Ala Thr Gly Ala  Ala Arg Ala Ala Tyr  Cys Ala Arg
    1070                 1075                 1080

Gly Gly  Asn Trp Ser Asn Ala  Ala Arg Ala Ala Arg  Ala Cys Asn
    1085                 1090                 1095

Tyr Thr  Asn Gly Gly Asn Trp  Ser Asn Ala Cys Asn  Met Gly Asn
    1100                 1105                 1110

Met Gly  Asn Gly Gly Asn Ala  Thr His Gly Ala Tyr  Ala Ala Tyr
    1115                 1120                 1125

Gly Gly  Asn Met Gly Asn Ala  Ala Arg Tyr Thr Asn  Met Gly Asn
    1130                 1135                 1140

Tyr Thr  Asn Gly Gly Asn Met  Gly Asn Cys Ala Arg  Thr Thr Tyr
    1145                 1150                 1155

Trp Ser  Asn Ala Cys Asn Trp  Ser Asn Ala Ala Arg  Gly Ala Tyr
    1160                 1165                 1170

Gly Thr  Asn Tyr Thr Asn Ala  Ala Tyr Ala Ala Arg  Tyr Thr Asn
    1175                 1180                 1185

Ala Ala  Arg Gly Cys Asn Tyr  Thr Asn Cys Ala Tyr  Cys Cys Asn
    1190                 1195                 1200

Tyr Thr  Asn Cys Cys Asn Gly  Gly Asn Tyr Thr Asn  Ala Thr His
    1205                 1210                 1215

Tyr Thr  Asn Gly Ala Arg Thr  Gly Gly Met Gly Asn  Met Gly Asn
    1220                 1225                 1230

Ala Thr  His Ala Cys Asn Ala  Ala Tyr Gly Cys Asn  Ala Thr His
    1235                 1240                 1245

Ala Cys  Asn Ala Ala Arg Gly  Thr Asn Gly Thr Asn  Thr Thr Tyr
    1250                 1255                 1260
```

-continued

```
Cys Cys Asn Tyr Thr Asn Cys Ala Arg Met Gly Asn Gly Ala Arg
    1265                1270                1275

Ala Ala Arg Thr Gly Tyr Tyr Thr Asn Ala Ala Tyr Cys Cys Asn
    1280                1285                1290

Thr Thr Tyr Tyr Thr Asn Gly Gly Asn Ala Thr Gly Gly Ala Arg
    1295                1300                1305

Met Gly Asn Ala Thr His Thr Ala Tyr Cys Cys Asn Gly Thr Asn
    1310                1315                1320

Trp Ser Asn Cys Ala Arg Trp Ser Asn Cys Ala Tyr Ala Cys Asn
    1325                1330                1335

Gly Cys Asn Ala Cys Asn Gly Gly Asn Met Gly Asn Ala Thr His
    1340                1345                1350

Ala Cys Asn Thr Thr Tyr Ala Cys Asn Gly Ala Arg Cys Cys Asn
    1355                1360                1365

Ala Ala Tyr Ala Thr His Cys Ala Arg Ala Ala Tyr Gly Thr Asn
    1370                1375                1380

Cys Cys Asn Met Gly Asn Gly Ala Tyr Thr Thr Tyr Gly Ala Arg
    1385                1390                1395

Ala Thr His Ala Ala Arg Ala Thr Gly Cys Cys Asn Ala Cys Asn
    1400                1405                1410

Tyr Thr Asn Gly Thr Asn Gly Gly Asn Gly Ala Arg Trp Ser Asn
    1415                1420                1425

Cys Cys Asn Cys Cys Asn Trp Ser Asn Cys Ala Arg Gly Cys Asn
    1430                1435                1440

Gly Thr Asn Gly Gly Asn Ala Ala Arg Gly Gly Asn Tyr Thr Asn
    1445                1450                1455

Tyr Thr Asn Cys Cys Asn Ala Thr Gly Gly Gly Asn Met Gly Asn
    1460                1465                1470

Gly Gly Asn Ala Ala Arg Thr Ala Tyr Ala Ala Arg Ala Ala Arg
    1475                1480                1485

Gly Gly Asn Thr Thr Tyr Trp Ser Asn Gly Thr Asn Ala Ala Tyr
    1490                1495                1500

Cys Cys Asn Met Gly Asn Thr Gly Tyr Cys Ala Arg Gly Cys Asn
    1505                1510                1515

Cys Ala Arg Ala Thr Gly Gly Ala Arg Gly Ala Arg Met Gly Asn
    1520                1525                1530

Gly Cys Asn Gly Cys Asn Gly Ala Tyr Met Gly Asn Gly Gly Asn
    1535                1540                1545

Ala Thr Gly Cys Cys Asn Thr Thr Tyr Trp Ser Asn Ala Thr His
    1550                1555                1560

Trp Ser Asn Ala Thr Gly Met Gly Asn Cys Ala Tyr Gly Cys Asn
    1565                1570                1575

Thr Thr Tyr Gly Thr Asn Cys Cys Asn Thr Thr Tyr Cys Cys Asn
    1580                1585                1590

Gly Gly Asn Gly Gly Asn Trp Ser Asn Ala Thr His Tyr Thr Asn
    1595                1600                1605

Gly Cys Asn Gly Cys Asn Gly Ala Tyr Thr Ala Tyr Trp Ser Asn
    1610                1615                1620

Cys Ala Arg Tyr Thr Asn Gly Ala Arg Tyr Thr Asn Met Gly Asn
    1625                1630                1635

Ala Thr His Tyr Thr Asn Gly Cys Asn Cys Ala Tyr Tyr Thr Asn
    1640                1645                1650
```

-continued

```
Trp Ser  Asn Cys Ala Tyr Gly  Ala Tyr Met Gly Asn  Met Gly Asn
    1655                 1660                 1665

Tyr Thr  Asn Ala Thr His Cys  Ala Arg Gly Thr Asn  Tyr Thr Asn
    1670                 1675                 1680

Ala Ala  Tyr Ala Cys Asn Gly  Gly Asn Gly Cys Asn  Gly Ala Tyr
    1685                 1690                 1695

Gly Thr  Asn Thr Thr Tyr Met  Gly Asn Trp Ser Asn  Ala Thr His
    1700                 1705                 1710

Gly Cys  Asn Gly Cys Asn Gly  Ala Arg Thr Gly Gly  Ala Ala Arg
    1715                 1720                 1725

Ala Thr  Gly Ala Thr His Gly  Ala Arg Cys Cys Asn  Gly Ala Arg
    1730                 1735                 1740

Trp Ser  Asn Gly Thr Asn Gly  Gly Asn Gly Ala Tyr  Gly Ala Tyr
    1745                 1750                 1755

Tyr Thr  Asn Met Gly Asn Cys  Ala Arg Cys Ala Arg  Gly Cys Asn
    1760                 1765                 1770

Ala Ala  Arg Cys Ala Arg Ala  Thr His Thr Gly Tyr  Thr Ala Tyr
    1775                 1780                 1785

Gly Gly  Asn Ala Thr His Ala  Thr His Thr Ala Tyr  Gly Gly Asn
    1790                 1795                 1800

Ala Thr  Gly Gly Gly Asn Gly  Cys Asn Ala Ala Arg  Trp Ser Asn
    1805                 1810                 1815

Tyr Thr  Asn Gly Gly Asn Gly  Ala Arg Cys Ala Arg  Ala Thr Gly
    1820                 1825                 1830

Gly Gly  Asn Ala Thr His Ala  Ala Arg Gly Ala Arg  Ala Ala Tyr
    1835                 1840                 1845

Gly Ala  Tyr Gly Cys Asn Gly  Cys Asn Thr Gly Tyr  Thr Ala Tyr
    1850                 1855                 1860

Ala Thr  His Gly Ala Tyr Trp  Ser Asn Thr Thr Tyr  Ala Ala Arg
    1865                 1870                 1875

Trp Ser  Asn Met Gly Asn Thr  Ala Tyr Ala Cys Asn  Gly Gly Asn
    1880                 1885                 1890

Ala Thr  His Ala Ala Tyr Cys  Ala Arg Thr Thr Tyr  Ala Thr Gly
    1895                 1900                 1905

Ala Cys  Asn Gly Ala Arg Ala  Cys Asn Gly Thr Asn  Ala Ala Arg
    1910                 1915                 1920

Ala Ala  Tyr Thr Gly Tyr Ala  Ala Arg Met Gly Asn  Gly Ala Tyr
    1925                 1930                 1935

Gly Gly  Asn Thr Thr Tyr Gly  Thr Asn Cys Ala Arg  Ala Cys Asn
    1940                 1945                 1950

Ala Thr  His Tyr Thr Asn Gly  Gly Asn Met Gly Asn  Met Gly Asn
    1955                 1960                 1965

Met Gly  Asn Thr Ala Tyr Tyr  Thr Asn Cys Cys Asn  Gly Gly Asn
    1970                 1975                 1980

Ala Thr  His Ala Ala Arg Gly  Ala Tyr Ala Ala Tyr  Ala Ala Tyr
    1985                 1990                 1995

Cys Cys  Asn Thr Ala Tyr Met  Gly Asn Ala Ala Arg  Gly Cys Asn
    2000                 2005                 2010

Cys Ala  Tyr Gly Cys Asn Gly  Ala Arg Met Gly Asn  Cys Ala Arg
    2015                 2020                 2025

Gly Cys  Asn Ala Thr His Ala  Ala Tyr Ala Cys Asn  Ala Thr His
    2030                 2035                 2040

Gly Thr  Asn Cys Ala Arg Gly  Gly Asn Trp Ser Asn  Gly Cys Asn
```

-continued

```
    2045                2050                2055

Gly Cys  Asn Gly Ala Tyr Ala  Thr His Gly Thr Asn  Ala Ala Arg
    2060                2065                2070

Ala Thr  His Gly Cys Asn Ala  Cys Asn Gly Thr Asn  Ala Ala Tyr
    2075                2080                2085

Ala Thr  His Cys Ala Arg Ala  Ala Arg Cys Ala Arg  Tyr Thr Asn
    2090                2095                2100

Gly Ala  Arg Ala Cys Asn Thr  Thr Tyr Cys Ala Tyr  Trp Ser Asn
    2105                2110                2115

Ala Cys  Asn Thr Thr Tyr Ala  Ala Arg Trp Ser Asn  Cys Ala Tyr
    2120                2125                2130

Gly Gly  Asn Cys Ala Tyr Met  Gly Asn Gly Ala Arg  Gly Gly Asn
    2135                2140                2145

Ala Thr  Gly Tyr Thr Asn Cys  Ala Arg Trp Ser Asn  Gly Ala Tyr
    2150                2155                2160

Cys Ala  Arg Ala Cys Asn Gly  Gly Asn Tyr Thr Asn  Trp Ser Asn
    2165                2170                2175

Met Gly  Asn Ala Ala Arg Met  Gly Asn Ala Ala Arg  Tyr Thr Asn
    2180                2185                2190

Cys Ala  Arg Gly Gly Asn Ala  Thr Gly Thr Thr Tyr  Thr Gly Tyr
    2195                2200                2205

Cys Cys  Asn Ala Thr His Met  Gly Asn Gly Gly Asn  Gly Gly Asn
    2210                2215                2220

Thr Thr  Tyr Thr Thr Tyr Ala  Thr His Tyr Thr Asn  Cys Ala Arg
    2225                2230                2235

Tyr Thr  Asn Cys Ala Tyr Gly  Ala Tyr Gly Ala Arg  Tyr Thr Asn
    2240                2245                2250

Tyr Thr  Asn Thr Ala Tyr Gly  Ala Arg Gly Thr Asn  Gly Cys Asn
    2255                2260                2265

Gly Ala  Arg Gly Ala Arg Gly  Ala Tyr Gly Thr Asn  Gly Thr Asn
    2270                2275                2280

Cys Ala  Arg Gly Thr Asn Gly  Cys Asn Cys Ala Arg  Ala Thr His
    2285                2290                2295

Gly Thr  Asn Ala Ala Arg Ala  Ala Tyr Gly Ala Arg  Ala Thr Gly
    2300                2305                2310

Gly Ala  Arg Trp Ser Asn Gly  Cys Asn Gly Thr Asn  Ala Ala Arg
    2315                2320                2325

Tyr Thr  Asn Trp Ser Asn Gly  Thr Asn Ala Ala Arg  Tyr Thr Asn
    2330                2335                2340

Ala Ala  Arg Gly Thr Asn Ala  Ala Arg Gly Thr Asn  Ala Ala Arg
    2345                2350                2355

Ala Thr  His Gly Gly Asn Gly  Cys Asn Trp Ser Asn  Thr Gly Gly
    2360                2365                2370

Gly Gly  Asn Gly Ala Arg Tyr  Thr Asn Ala Ala Arg  Gly Ala Tyr
    2375                2380                2385

Thr Thr  Tyr Gly Ala Tyr Gly  Thr Asn
    2390                2395
```

MODIFICATION OF 3' TERMINAL ENDS OF NUCLEIC ACIDS BY DNA POLYMERASE THETA

CROSS-REFERENCE TO RELATED APPLICATIONS

This application is a Continuation of U.S. application Ser. No. 15/772,192, filed Apr. 30, 2018, which is a U.S. national phase application filed under 35 U.S.C. § 371 claiming benefit to International Patent Application No. PCT/US16/59419, filed Oct. 28, 2016, which claims priority to U.S. Provisional Application No. 62/338,119, filed May 18, 2016, and U.S. Provisional Application No. 62/248,083, filed Oct. 29, 2015, the disclosures of which are incorporated herein by reference in their entireties.

STATEMENT REGARDING FEDERALLY SPONSORED RESEARCH OR DEVELOPMENT

This invention was made with government support under 1R01GM115472-01 and 4R00CA160648-03 awarded by the National Institute of Health. The government has certain rights in the invention.

BACKGROUND OF THE INVENTION

DNA polymerases (Pols) are crucial to life since they are necessary for the propagation and maintenance of genetic information. Intriguingly, human cells encode for several different types of Pols, many of which are intrinsically error-prone due to their open active sites which enables them to tolerate particular DNA lesions (Sale et al., 2012, Nature Rev Mol Cell Biol 13:141-52; Waters et al., 2009, Microbiol Mol Biol Rev 73:134-54). Such enzymes are referred to as translesion polymerases and are mostly among the Y-family of polymerases. A unique A-family polymerase encoded by POLQ, however, also tolerates bulky lesions and is capable of replicating past the most lethal lesion, a double-strand break (DSB) (Kent et al., 2015, Nat Struct Mol Biol 22:230-7; Yoon et al., 2014, J Biol Chem 289:13177-85; Yousefzadeh et al., 2014, PLoS Genet 10:e1004654; Mateos-Gomez et al., 2015, Nature 518:254-7; Hogg et al., 2011, J Mol Biol 405:642-52; Seki et al., 2003, Nucleic Acids Res 31:6117-26; Chan et al., 2010, PLoS Genet 6:e1001005; Koole et al., 2014, Nat Commun 5:3216). For example, recent studies demonstrate the ability of the polymerase domain encoded by human POLQ, herein referred to as Polθ, to perform microhomology-mediated end-joining (MMEJ)—also referred to as alternative non-homologous endjoining (alt-NHEJ)—which involves the ability of the polymerase to perform replication across a DNA synapse stabilized by a minimal amount of sequence homology (Kent et al., 2015, Nat Struct Mol Biol 22:230-7). Further studies show that Polθ is essential for MMEJ/alt-NHEJ (Yousefzadeh et al., 2014, PLoS Genet 10:e1004654; Mateos-Gomez et al., 2015, Nature 518:254-7; Chan et al., 2010, PLoS Genet 6:e1001005; Koole et al., 2014, Nat Commun 5:3216), and as a potential result of this, promotes the survival of cancer cells deficient in the accurate homologous recombination (HR) pathway (Mateos-Gomez et al., 2015, Nature 518:254-7).

Studies in invertebrates and mammalian cells demonstrate the presence of non-templated nucleotide insertions at alt-NHEJ repair junctions which were shown to be dependent on the DNA synthesis activity of Polθ (Yousefzadeh et al., 2014, PLoS Genet 10:e1004654; Mateos-Gomez et al., 2015, Nature 518:254-7; Chan et al., 2010, PLoS Genet 6:e1001005; Koole et al., 2014, Nat Commun 5:3216). Yet, insofar Polθ template-independent terminal transferase activity has not been demonstrated in vitro. For example, early in vitro studies showed the unusual ability of Polθ to extend ssDNA and partial ssDNA substrates with 3' overhangs (pssDNA) (Hogg et al., 2012, Nucleic Acid Res 40:2611-22). Although it was suggested that this activity might be the result of template-independent terminal transferase activity, the polymerase failed to extend homopolymeric ssDNA templates, which contain a single type of base, without the complementary dNTP present (Hogg et al., 2012, Nucleic Acid Res 40:2611-22). These previous studies therefore demonstrated a lack of template-independent terminal transferase activity by Polθ (Hogg et al., 2012, Nucleic Acid Res 40:2611-22). More recent studies presented evidence suggesting that the polymerase extends ssDNA by transiently annealing two oligonucleotides together in an anti-parallel manner, resulting in repeated use of the opposing ssDNA as a template in trans (Yousefzadeh et al., 2014, PLoS Genet 10:e1004654). Although this is a formal possibility given the ability of Polθ to promote MMEJ of pssDNA, recent studies have instead showed that the polymerase extends ssDNA by performing 'snap-back' replication on the same template (Kent et al., 2015, Nat Struct Mol Biol 22:230-7). Regardless of the mechanisms by which the polymerase extended ssDNA under the particular conditions used in previous studies, to date the ability of Polθ to perform template-independent terminal transferase activity in vitro has not been demonstrated. Thus, it remains unclear how the polymerase generates random nucleotide insertions during alt-NHEJ in vivo. For example, it remains unknown whether auxiliary proteins or co-factors are necessary for activating Polθ template-independent terminal transferase activity.

Considering that template-independent transfer of canonical and modified deoxyribonucleotides and ribonucleotides to DNA and RNA is important for many applications in biotechnology and biomedical research, investigating the ability of Polθ to extend DNA and RNA substrates is potentially critical for identifying a new mechanism of template-independent terminal transferase activity. Currently, the only marketed enzyme for modifying the 3' terminal ends of DNA is terminal deoxynucleotidyl transferase (TdT). However, TdT is limited in this activity in many ways.

Thus, there is a need in the art for compositions and methods providing an effective template-independent transfer of canonical and modified deoxyribonucleotides and ribonucleotides to both DNA and RNA. The present invention satisfies this unmet need.

SUMMARY OF THE INVENTION

In one aspect, the invention provides a method of modifying a 3' terminal end of a nucleic acid with a substrate. In one embodiment, the method comprises forming a mixture comprising an A family polymerase, a substrate, a nucleic acid, and a reaction solution, wherein the reaction solution comprises at least one divalent metal; incubating the mixture; and isolating a 3'-terminal end modified nucleic acid.

In one embodiment, the nucleic acid is s single stranded DNA (ssDNA), double stranded DNA, partial ssDNA, RNA or telomeric ssDNA.

In one embodiment, the A family polymerase is Polθ or an active fragment thereof. In one embodiment, Polθ comprises the amino acid sequence of SEQ ID NO 1.

In one embodiment, the labeled dNTP cy3-dUTP, Digoxigenin-11-dUTP, Biotin-16AA-dUTP, Texas Red-5-dCTP, Cyanine 3-AA-UTP, 4-Thio-UTP, Biotin-16-AACTP, Ganciclovir Triphosphate, N6-(6-Azido)hexyl-adenosine-5'-triphosphate, or 5-Hydroxymethyl-2'-deoxyuridine-5'-Triphosphate.

In one embodiment, the divalent metal is manganese ($Mn^{2+}$), cobalt ($Co^{2+}$), or a combination thereof. In one embodiment, the divalent metal is at a concentration of about 1 mM to about 50 mM. In some embodiments, the divalent metal is at a concentration of about 5 mM.

In one embodiment, the reaction solution further comprises glycerol, a non-ionic detergent, and a buffer. In one embodiment the concentration of the glycerol in the reaction solution is less than or equal to 20%. In one embodiment, the concentration of glycerol in the reaction solution is 10%. In one embodiment, concentration of the non-ionic detergent is less than 1%. In one embodiment, the concentration of the non-ionic detergent is 0.1%. In one embodiment, the buffer is MES/TRIS and wherein MES/TRIS is at a concentration of about 20 mM to about 100 mM. In one embodiment, the pH of the buffer is 6.5-8.8. In one embodiment, the pH of the buffer is 8.2.

In one embodiment, the step incubating the mixture comprises incubating the mixture for at least 2 hours. In one embodiment, the step incubating the mixture comprises incubating the mixture at 25° C.-42° C. In one embodiment, the step incubating the mixture comprises incubating the mixture at 42° C.

The present invention also provides a kit for modifying a 3' terminal end of a nucleic acid with a substrate. In one embodiment, the kit comprises an A-family polymerase and a reaction solution. In one embodiment, the kit further comprising the substrate.

In one embodiment the A-family polymerase is Polθ.

In on embodiment the reaction solution comprises 5 mM $Mn^{2+}$, 20 mM Tris HCl pH 8.2, 10% glycerol, 0.01% NP-40 and 0.1 mg/mL BSA.

The present invention also provides a method de novo synthesis of nucleic acids. In one embodiment, the method comprises forming a mixture comprising an A family polymerase, at least one nucleobase, and a reaction solution, wherein the reaction solution comprises at least one divalent metal; incubating the mixture; and isolating a nucleic acid.

In one embodiment, A family polymerase is Polθ.

In one embodiment, the at least one nucleobase is selected from ATP, UTP, GTP, dATP, dTTP, dGTP, dCTP, and any combination thereof.

In one embodiment the at least one divalent metal is Mn2+.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts denaturing gels showing Polθ extension of poly-dC ssDNA with dTTP in the presence of indicated divalent cations. FIG. 1B depicts denaturing gels showing Polθ extension of poly-dC ssDNA with dTTP in the presence of increasing amounts of $Mn^{2+}$. FIG. 1C depicts denaturing gels showing Polθ extension of poly-dC ssDNA with dTTP in the presence of indicated pH levels and buffer concentrations. FIG. 1D depicts denaturing gels showing Polθ extension of poly-dC ssDNA with dTTP in the presence of indicated amounts of salts. FIG. 1E depicts denaturing gels showing Polθ extension of poly-dC ssDNA with dTTP in the presence of increasing concentrations of glycerol and NP-40.

FIG. 2, comprising FIG. 2A depicts denaturing gels showing Polθ extension of poly-dC ssDNA with dTTP in the presence of increasing amounts of Polθ. FIG. 2B depicts denaturing gels showing Polθ extension of poly-dC ssDNA with dTTP at increasing time intervals at the indicated temperatures.

FIG. 3, comprising FIG. 3A depicts denaturing gels showing Polθ extension of poly-dC (left) and poly-dT (right) ssDNA with the indicated dNTPs. FIG. 3B depicts a denaturing gel showing Polθ extension of the indicated ssDNA with indicated dNTPs. FIG. 3C depicts a denaturing gel showing Polθ extension of the indicated non-homopolymeric ssDNA in the presence of magnesium and manganese. FIG. 3D depicts denaturing gels showing Polθ extension of the indicated dsDNA with indicated dNTPs. FIG. 3E depicts a denaturing gel showing Polθ extension of double-strand DNA. FIG. 3F depicts a denaturing gel showing Polθ extension of the indicated pssDNA with indicated dNTPs. FIG. 3G depicts enaturing gels showing Polθ extension of ssDNA modeled after telomere sequence with the indicated dNTPs.

FIG. 4, comprising FIG. 4A depicts denaturing gels showing Polθ (lanes 1-6) and Polµ (lanes 7-12) extension of poly-dC (left) and nonhomopolymeric ssDNA (right) with the indicated dNTPs. FIG. 4B depicts a denaturing gel showing Polθ (lanes 1-5) and TdT (lanes 6-10) extension of ssDNA with the indicated dNTPs. FIG. 4C depicts a denaturing gel showing Polθ and TdT extension of ssDNA with the indicated ribonucleotides (rNTPs). FIG. 4D depicts a denaturing gel showing Polθ and TdT extension of ssDNA with the following modified nucleotide analogs: 1, cy3-dUTP; 2, Digoxigenin-11-dUTP; 3, Biotin-16AA-dUTP; 4, Texas Red-5-dCTP; 5, N6-(6-Azido)hexyl-ATP; 6, Cyanine 3-AA-UTP; 7, 4-Thio-UTP; 8, Biotin-16-AACTP; 9, Ganciclovir Triphosphate; 10, 5-Hydroxymethyl-2'-deoxyuridine-5'-Triphosphate.

FIG. 6, comprising FIG. 6A depicts a denaturing gels showing Polθ extension of RNA in the presence of deoxyribonucleotides. FIG. 6B depicts a denaturing gel showing Polθ extension of RNA with the indicated modified nucleotides (see FIG. 5).

FIG. 7, comprising FIG. 7A depicts a model of Polθ dependent DNA end-joining where Polθ uses existing sequence microhomology to facilitate DNA end-joining. FIG. 7B depicts a model of Polθ dependent DNA end-joining where Polθ extends ssDNA by a template-independent mechanism, then uses the newly generated sequence to facilitate DNA end-joining. FIG. 7C depicts a model of Polθ dependent DNA end-joining where Polθ extends ssDNA by using the opposing overhang as a template in trans, then after DNA synapse dissociation Polθ uses the newly generated sequence to facilitate DNA end-joining. FIG. 7D depicts a denaturing gel showing Polθ extension of poly-dC ssDNA in the presence of indicated dNTPs and 10 mM $Mg^{2+}$. FIG. 7E depicts a denaturing gel showing Polθ extension of poly-dC ssDNA in the presence of dTTP and indicated divalent cation concentrations and time intervals. FIG. 7F depicts a denaturing gel showing Polθ extension of poly-dC ssDNA in the presence of dTTP and indicated divalent cation concentrations and temperatures. FIG. 7G depicts denaturing gels showing Polθ extension of indicated ssDNA in the presence of all four dNTPs and 10 mM $Mg^{2+}$ or 5 mM $Mn^{2+}$.

FIG. 8, comprising FIG. 8A depicts denaturing gels showing Polθ extension of poly-dT in the presence of dCTP with indicated concentrations of $Mn^{2+}$ and $Mg^{2+}$. FIG. 8B depicts plots of percent ssDNA extension observed in panel A. Percent extension was calculated by dividing the intensity of the sum of the extended products by the sum of the intensity of all DNA in each lane.

FIG. 9, comprising FIG. 9A depicts a denaturing gel showing Pol-$Mn^{2+}$ extension of poly-dC ssDNA in the presence of dTTP with indicated [$Mn^{2+}$]. FIG. 9B a denaturing gel showing Pol-$Mn^{2+}$ extension of poly-dC ssDNA in the presence of dTTP with 5 mM $Mn^{2+}$ and the indicated buffer. FIG. 9C a denaturing gel showing Pol-$Mn^{2+}$ extension of poly-dC ssDNA in the presence of dTTP with 5 mM $Mn^{2+}$ and the indicated salt. FIG. 9D a denaturing gel showing Pol-$Mn^{2+}$ extension of poly-dC ssDNA in the presence of dTTP with 5 mM $Mn^{2+}$ and the indicated detergent and glycerol. FIG. 9E a denaturing gel showing Pol-$Mn^{2+}$ extension of poly-dC ssDNA in the presence of dTTP with 5 mM $Mn^{2+}$ and the indicated Polθ concentration.

FIG. 10, comprising FIG. 10A depicts a schematic of method used to sequence Polθ-$Mg^{2+}$ extension products. FIG. 10B depicts, sequences of extension products generated by Polθ in the presence of 10 mM $Mg^{2+}$, all four dNTPs, and ssDNA RP347. Initial sequence of RP347 ssDNA is indicated at top. Sequences of extension products are shown in a 5'-3' direction. Black underline, sequence copied from template. FIG. 10C depicts a model of how Polθ-$Mg^{2+}$ repeatedly generates products 1-8 from RP347 ssDNA via snap-back replication. FIG. 10D depicts representative sequence traces of products 1-8 demonstrating non-identical sequencing reactions and files. Certain sequences are represented as complements due to their particular orientation resulting from cloning into plasmid vectors.

FIG. 11, comprising FIG. 11A through FIG. 11E, depicts results of experiments demonstrating that Polθ oscillates between three different modes of terminal transferase activity. FIG. 11A depicts sequences of Polθ ssDNA extension products in the presence of 5 mM $Mn^{2+}$. Initial ssDNA sequences are indicated at top. Black underlines, sequences copied from either original template or complementary sequences generated from original template; matching colored lines, complementary sequences due to snap-back replication. FIG. 11B depicts sequences of Polθ ssDNA extension products in the presence of 10 mM $Mg^{2+}$ and 1 mM $Mn^{2+}$. Initial ssDNA sequences are indicated at top. Black underlines, sequences copied from either original template or complementary sequences generated from original template; matching colored lines, complementary sequences due to snap-back replication. FIG. 11C depicts models of Polθ terminal transferase activities. (Top) Polθ preferentially exhibits template-independent activity in the presence of $Mg^{2+}$ and $Mn^{2+}$. Polθ also performs templated ssDNA extension in cis (bottom left) and in trans (bottom right), and oscillates between these three mechanisms. FIG. 11D depicts models of Polθ terminal transferase activity based on sequences 3 and 8 from FIG. 11B. FIG. 11E depicts a plot showing lengths of ssDNA products generated by Polθ in the presence of indicated divalent cations.

FIG. 13, comprising FIG. 13A depicts a scheme for reconstitution of Polθ mediated alt-EJ in vitro (top) and sequences of alt-EJ products generated by Polθ in vitro using 10 mM $Mg^{2+}$ and 1 mM $Mn^{2+}$ (bottom). Red text, insertions; black text, original DNA sequence; black and grey underlines, sequences copied from original template; red underlines, complementary sequences due to snap-back replication; red sequence without underlines, random insertions; superscript 1, suggests sequences were copied from a template portion that was subsequently deleted during alt-EJ; superscript 2, suggests sequences were copied from the template in more than one way. Original DNA sequences indicated at top. Blue type, mutations. FIG. 13B depicts a plot of insertion tract lengths generated in FIG. 13A. FIG. 13C depicts a chart depicting percent of individual nucleotide insertion events due to non-templated extension, templated extension in cis and templated extension in trans. t test indicates no significant difference between percent of non-templated and templated in cis insertions. FIG. 13D depicts models of Polθ activity based on end-joining products 1 and 2 from FIG. 13A.

FIG. 14, comprising FIG. 14A depicts a scheme for Polθ mediated alt-EJ of site-specific DSBs in mouse embryonic stem cells (top) and sequences of alt-EJ products generated by Polθ in cells (bottom). FIG. 14B depicts a plot of insertion tract lengths generated in FIG. 14A. FIG. 14C depicts a chart depicting percent of individual nucleotide insertion events due to non-templated extension, templated extension in cis and templated extension in trans. t test indicates no significant difference between percent of non-templated and templated in cis insertions. FIG. 14D depicts models of Polθ activity based on end-joining products 1 and 2 from FIG. 14A.

FIG. 15, comprising FIG. 15A depicts a schematic of experimental conditions. FIG. 15B depicts a model of sequential activity of Polθ-Mn$^{2+}$ on a primer-template (top). Sequences generated by Polθ-Mn$^{2+}$ during primer-extension in solid-phase in the presence of 5 mM Mn$^{2+}$. Black sequence, template-dependent; red sequence, template-independent; blue sequence, misincorporation; dash, frameshift mutation. Colored lines, complementary sequences generated by snap-back replication. FIG. 15C depicts models of Polθ activity on a primer-template in the presence of Mg$^{2+}$ and Mn$^{2+}$ (top). Denaturing gels showing Polθ primer-extension products in the presence of 10 mM Mg$^{2+}$ (left) and 5 mM Mn$^{2+}$ (right). FIG. 15d depicts models of Polθ-Mn$^{2+}$ activity on a primer-template and ssDNA in the presence of dATP (top). Denaturing gels showing template-dependent (left) and template-independent (right) Polθ-Mn$^{2+}$ activities on a primer-template (left) and primer (right), respectively, in the presence of 5 mM Mn$^{2+}$ and dATP.

FIG. 17, comprising FIG. 17A depicts the schematic of the experiment (left) and a denaturing gel showing inhibition of Polθ-Mn$^{2+}$ terminal transferase activity by a ssDNA trap (right). FIG. 17B depicts the schematic of the experiment (left) and a denaturing gel showing a time course of Polθ-Mn$^{2+}$ terminal transferase activity in the presence and absence of ssDNA trap (right).

FIG. 18, comprising FIG. 18A depicts a scheme of experiment performed in solid-phase. FIG. 18B depicts a bar graph depicting ssDNA product lengths generated by Polθ in the presence (orange) and absence (grey) of excess ssDNA with 10 mM Mg$^{2+}$ and 1 mM Mn$^{2+}$. FIG. 18C depicts sequences generated by Polθ incubated with the indicated ssDNA substrate in the presence of excess ssDNA trap with 10 mM Mg$^{2+}$, 1 mM Mn$^{2+}$, and all four dNTPs. Black underlines, sequences identical or complementary to initial ssDNA substrate; red underlines, sequences complementary to ssDNA trap; colored lines above text, complementary sequences within individual ssDNA products. FIG. 18D depicts sequences generated by Polθ incubated with the indicated ssDNA substrate in the absence of excess ssDNA trap with 10 mM Mg$^{2+}$, 1 mM Mn$^{2+}$, and all four dNTPs. Black underlines, sequences identical or complementary to initial ssDNA substrate; red underlines, sequences complementary to ssDNA trap; colored lines above text, complementary sequences within individual ssDNA products.

FIG. 19 depicts results of experiments demonstrating that Polθ oscillates between templated and non-templated terminal transferase activities in the presence of physiological concentrations of Mg$^{2+}$ and Mn$^{2+}$. Sequences generated by Polθ during ssDNA extension in the presence of 1 mM Mg$^{2+}$ and 50 µM Mn$^{2+}$. Black and grey inderlines, sequence complementary to initial ssDNA substrate; red underline, sequence identical to initial ssDNA substrate; blue lines, complementary sequence generated by snap-back replication; red text without lines, random insertions. Initial ssDNA sequence indicated at top.

FIG. 20, comprising FIG. 20A depicts a schematic of alt-EJ reaction and subsequent procedures used for amplification and sequencing of endjoining products. Control alt-EJ reactions were performed with 10 mM Mg$^{2+}$ and 1 mM Mn$^{2+}$. FIG. 20B depicts non-denaturing gels showing the products of PCR reactions containing either purified DNA from alt-EJ reactions performed in the presence of Polθ and Lig3 (top left), Polθ alone (top middle), and in the absence of Polθ and Lig3 (top right), or no DNA with primers only (bottom middle). Products in the top middle and top right gels are due to primer-dimer events as shown in the primers only control (bottom middle gel). Lanes 1-8 represent PCR reactions performed at the following respective temperatures: 61° C., 60.8° C., 60.4° C., 59.9° C., 59.2° C., 58.6° C., 58.2° C., 58° C. Lanes 9-13 represent PCR reactions performed in the absence of PCR primers RP435 and RP431 and at the following respective temperatures: 61° C., 60.4° C., 59.9° C., 59.2° C., 58.2° C. The absence of PCR products in lanes 9-13 show that Taq polymerase cannot amplify original pssDNA templates via endjoining or other mechanisms. FIG. 20C depicts a plot showing percent of end-joining products observed in cloning vectors following end-joining reactions containing the indicated proteins. Red, end-joining products with insertions; grey, end-joining products without insertions. n=64 (+Polθ, +Lig3), n=72 (+Polθ, −Lig3), n=12 (−Polθ, −Lig3). End-joining products in the absence of Polθ and Lig3 are likely due to infrequent byproducts of PCR.

FIG. 21, comprising FIG. 21A depicts a scheme for reconstitution of Polθ mediated alt-EJ in vitro with ssDNA trap (top) and sequences of alt-EJ products generated by Polθ in vitro using 10 mM Mg$^{2+}$ and 1 mM Mn$^{2+}$ (bottom). FIG. 21B depicts a plot of insertion tract lengths generated in FIG. 21A.

FIG. 22, comprising FIG. 22A depicts a scheme for reconstitution of Polθ mediated alt-EJ in vitro with 1 mM Mg$^{2+}$ and 50 µM Mn$^{2+}$ (top) and sequences of Polθ-mediated alt-EJ products with insertions >2 bp (bottom). FIG. 22B depicts a plot of insertion tract lengths illustrated in FIG. 22A. FIG. 22C depicts a plot showing percentage of Polθ-mediated alt-EJ products with and without insertions. n=32.

FIG. 24, comprising FIG. 24A depicts a scheme for Polθ mediated alt-EJ of site-specific DSBs in mouse embryonic stem cells (top) and sequences of alt-EJ products generated by Polθ in cells (bottom). FIG. 24B depicts a pie chart of insertion tract lengths generated in vivo. n=118.

FIG. 25, comprising FIG. 25A depicts denaturing gels showing Polθ extension of poly-dC (left) and poly-dT (right) ssDNA with 5 mM $Mn^{2+}$ and the indicated dNTPs. FIG. 25B depicts a denaturing gel showing Polθ extension of the indicated ssDNA with 5 mM $Mn^{2+}$ and indicated dNTPs. FIG. 25C depicts a denaturing gel showing Polθ extension of the indicated dsDNA with 5 mM $Mn^{2+}$ and indicated dNTPs. FIG. 25D depicts a denaturing gel showing Polθ extension of a primer-template with 5 mM $Mn^{2+}$ and all four dNTPs. Model of Polθ-$Mn^{2+}$ activity on a primer-template (right). FIG. 25E depicts a denaturing gel showing Polθ extension of the indicated pssDNA with 5 mM $Mn^{2+}$ and indicated dNTPs. FIG. 25F depicts denaturing gels showing Polθ extension of ssDNA modeled after telomere sequence with 5 mM $Mn^{2+}$ and the indicated dNTPs.

FIG. 26, comprising FIG. 26A depicts a denaturing gel showing Polθ and Polμ extension of poly-dC in the presence of $Mn^{2+}$ and the indicated nucleotides. FIG. 26B depicts a denaturing gel showing Polθ and Polμ extension of RP347 ssDNA in the presence of $Mn^{2+}$ and the indicated nucleotides.

FIG. 27, comprising FIG. 27A through FIG. 27G depicts results of experiments demonstrating that conserved residues contribute to Polθ processivity and template-independent terminal transferase activity.

FIG. 27A depicts a sequence alignment of Polθ and related A-family Pols. Conserved positively charged residues (2202, 2254) and loop 2 in Polθ are highlighted in yellow and grey, respectively. Black boxes indicate conserved motifs. *=identical residues, :=residues sharing very similar properties, .=residues sharing some properties.

FIG. 28, comprising FIG. 28A depicts a denaturing gel showing Polθ-$Mn^{2+}$ (lanes 1-5) and TdT (lanes 6-10) extension of ssDNA with the indicated dNTPs. FIG. 28B depicts a denaturing gel showing Pol-$Mn^{2+}$ (lanes 1-6) and TdT (lanes 7-12) extension of ssDNA with the indicated ribonucleotides (rNTPs). FIG. 28C depicts a denaturing gel showing Polθ-$Mn^{2+}$ (lanes 1-11) and TdT (lanes 12-22) extension of ssDNA with the indicated nucleotide analogs illustrated in FIG. 28D. Boxed lanes indicate nucleotides analogs that are exclusively transferred by Polθ-$Mn^{2+}$. FIG. 28D depicts Nucleotide analogs: 1, cy3-dUTP; 2, Digoxigenin-11-dUTP; 3, Biotin-16AA-dUTP; 4, Texas Red-5-dCTP; 5, N6-(6-Azido) hexyl-ATP; 6, Cyanine 3-AA-UTP; 7, 4-Thio-UTP; 8, Biotin-16AA-CTP; 9, Ganciclovir Triphosphate; 10, 5-Hydroxymethyl-2'-deoxyuridine-5'-Triphosphate. Underlined nucleotide analogs (4,5,9) are exclusively transferred by Polθ-$Mn^{2+}$. FIG. 28E depicts a denaturing gel showing Polθ-$Mn^{2+}$ extension of RNA with all four dNTPs in the presence (lane 3) and absence (lane 2) of unlabeled ssDNA (left panel) and a denaturing gel showing Pol-$Mn^{2+}$ extension of RNA with the indicated nucleotide analogs (right panel).

DETAILED DESCRIPTION

Figures 1A, 1B:
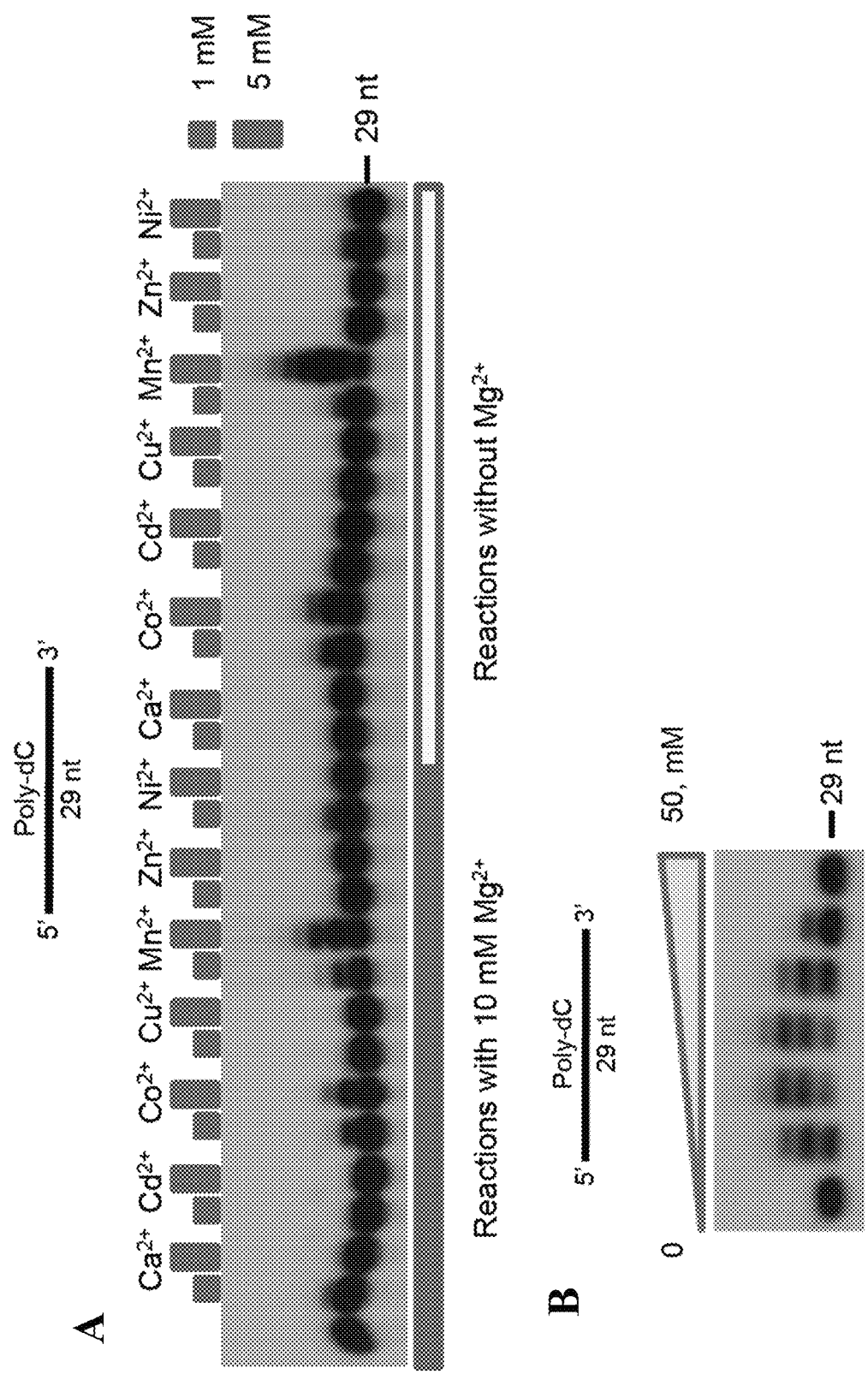
FIG. 1A through FIG. 1E, depicts results of experiments demonstrating that Polθ exhibits template-independent terminal transferase activity in the presence of manganese and cobalt.

The present invention is based on the discovery that Polθ possesses robust template-independent terminal transferase activity on DNA and RNA. In some instances, Polθ possesses robust template-independent terminal transferase activity exclusively in the presence of manganese. In other instances, Polθ possesses robust template-independent terminal transferase activity exclusively in the presence of cobalt. Under these conditions, Polθ efficiently transfers deoxyribonucleotides to the 3' terminal end of single-strand DNA (ssDNA), partial ssDNA (pssDNA), double-strand DNA (dsDNA), and single-strand RNA (RNA). Polθ also efficiently transfers ribonucleotides and modified nucleotide analogs containing various large functional groups, such as fluorophores, biotin, and digoxigenin, to DNA and RNA. Unexpectedly, Polθ is more effective in transferring ribonucleotides and modified nucleotides to ssDNA compared to commercially available terminal deoxynucleotidyl transferase (TdT).

Accordingly, the invention provides methods and compositions for modifying the terminal 3' ends of nucleic acids.

In one embodiment, the method of the invention comprises reacting an A-family polymerase with a nucleic acid to be modified on the 3' terminal end, a substrate to modify the nucleic acid in a reaction solution comprising a divalent metal, incubating the reaction and then isolating a 3'-terminal end modified nucleic acid.

In some instances the nucleic acid oligo to be modified is single stranded DNA (ssDNA), double stranded DNA (dsDNA), partial ssDNA (psDNA), RNA, or telomeric ssDNA.

In one embodiment, the A-family polymerase is Polθ. In some embodiments, the A-family polymerase is a fragment of Polθ. In certain embodiments the fragment of Polθ is Polθ$_{1792-2590}$, represented by SEQ ID NO 1. In certain embodiments Polθ is encoded by the human POLQ gene. In other embodiments Polθ is encoded by the C. elegans polq-1 gene.

In one embodiment, the substrate is a nucleotide. In some embodiments the deoxyribonucleotide is dATP, dGTP, dCTP, dATP, or dUTP. In some embodiments the ribonucleotide is ATP, GTP, CTP, or UTP. In other embodiments the nucleotide is modified. In certain non-limiting embodiments, the modified nucleotide may be cy3-dUTP, Digoxigenin-11-dUTP, Biotin-16AA-dUTP, Texas Red-S-dCTP, Cyanine 3-AA-UTP, 4-Thio-UTP, Biotin-16-AACTP, Ganciclovir Triphosphate, N6-(6-Azido)hexyl-adenosine-5'-triphosphate, and 5-Hydroxymethyl-2'-deoxyuridine-5'-Triphosphate. In some embodiments the substrate can be any combination of nucleotides and modified nucleotides.

In one embodiment the divalent metal is $Mn^{2+}$ or $Co^{2+}$. In one embodiment, the concentration of the divalent metal in the reaction solution is about 1-50 mM with about 2-5 mM being preferred and about 5 mM being most preferred.

In one embodiment, the reaction solution further comprises a buffer. In certain embodiments the buffer is MES/TRIS. In one embodiment, the concentration of the buffer in the reaction solution is about 20-100 mM with about 20 mM being preferred. In yet another embodiment the pH of the buffer is about 6.5-8.8, with a pH of about 7-8.2 being preferred and a pH of about 8.2 being more preferred.

In one embodiment, the reaction solution further comprises glycerol. In one embodiment, the concentration of glycerol in the reaction solution is about 0-20% with about 10% being preferred.

In one embodiment, the reaction solution further comprises a non-ionic detergent. In certain embodiments the non-ionic detergent is NP-40. In some embodiments, the concentration of the non-ionic detergent in the reaction solution is about 0-1% with about 0.1% being preferred.

In one embodiment the reaction mixture is incubated for at least 2 hours. In one embodiment, the reaction mixture is incubated at a temperature of about 25° C.-42° C. In another embodiment the reaction mixture is incubated at a temperature of about 42° C.

The invention also provides a kit for modifying a 3' terminal end of a nucleic acid with a substrate. In one embodiment the kit comprises an A-family polymerase and a reaction solution. In another embodiment the kit further comprises the substrate.

In one embodiment the A-family polymerase is Polθ.

In one embodiment the reaction solution comprises 5 mM $Mn^2$, 20 mM Tris HCl pH 8.2, 10% glycerol, 0.01% NP-40 and 0.1 mg/mL BSA.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of 40% or 20% or 10%, $\pm 5\%$, 1%, or 0.1% from the specified value, as such variations are appropriate.

"Amplification" refers to any means by which a polynucleotide sequence is copied and thus expanded into a larger number of polynucleotide molecules, e.g., by reverse transcription, polymerase chain reaction, and ligase chain reaction, among others. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

"Homologous, homology" or "identical, identity" as used herein, refer to comparisons among amino acid and nucleic acid sequences. When referring to nucleic acid molecules, "homology," "identity," or "percent identical" refers to the percent of the nucleotides of the subject nucleic acid sequence that have been matched to identical nucleotides by a sequence analysis program. Homology can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the ExPaSy is used to align sequence fragments of genomic DNA sequences. However, equivalent alignment assessments can be obtained through the use of any standard alignment software.

As used herein, "homologous" refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'ATTGCC 3' and 5'TATGGC 3' share 50% homology.

"Hybridization probes" are oligonucleotides capable of binding in a base-specific manner to a complementary strand of nucleic acid. Such probes include peptide nucleic acids, as described in Nielsen et al., 1991, Science 254, 1497-1500, and other nucleic acid analogs and nucleic acid mimetics. See U.S. Pat. No. 6,156,501.

The term "hybridization" refers to the process in which two single-stranded nucleic acids bind non-covalently to form a double-stranded nucleic acid; triple-stranded hybridization is also theoretically possible. Complementary sequences in the nucleic acids pair with each other to form a double helix. The resulting double-stranded nucleic acid is a "hybrid." Hybridization may be between, for example, two complementary or partially complementary sequences. The hybrid may have double-stranded regions and single stranded regions. The hybrid may be, for example, DNA:DNA, RNA:DNA or DNA:RNA. Hybrids may also be formed between modified nucleic acids. One or both of the nucleic acids may be immobilized on a solid support. Hybridization techniques may be used to detect and isolate specific sequences, measure homology, or define other characteristics of one or both strands.

The stability of a hybrid depends on a variety of factors including the length of complementarity, the presence of mismatches within the complementary region, the temperature and the concentration of salt in the reaction. Hybridizations are usually performed under stringent conditions, for example, at a salt concentration of no more than 1 M and a temperature of at least 25° C. For example, conditions of 5×SSPE (750 mM NaCl, 50 mM Na Phosphate, 5 mM EDTA, pH 7.4) or 100 mM MES, 1 M Na, 20 mM EDTA, 0.01% Tween-20 and a temperature of 25-50° C. are suitable for allele-specific probe hybridizations. In a particularly preferred embodiment, hybridizations are performed at 40-50° C. Acetylated BSA and herring sperm DNA may be added to hybridization reactions. Hybridization conditions suitable for microarrays are described in the Gene Expression Technical Manual and the GeneChip Mapping Assay Manual available from Affymetrix (Santa Clara, CA).

A first oligonucleotide anneals with a second oligonucleotide with "high stringency" if the two oligonucleotides anneal under conditions whereby only oligonucleotides which are at least about 75%, and preferably at least about 90% or at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g. Sambrook et al., 2012, Molecular Cloning: A Laboratory Manual, Cold Spring Harbor Laboratory Press, Cold Spring Harbor, N.Y.).

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

As used herein, "isolate" refers to a nucleic acid obtained from an individual, or from a sample obtained from an individual. The nucleic acid may be analyzed at any time after it is obtained (e.g., before or after laboratory culture, before or after amplification.)

As used herein, the term "purified" or "to purify" refers to the removal of components (e.g., contaminants) from a sample. For example, nucleic acids are purified by removal of contaminating cellular proteins or other undesired nucleic acid species. The removal of contaminants results in an increase in the percentage of desired nucleic acid in the sample.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

The term "mismatch," "mismatch control" or "mismatch probe" refers to a nucleic acid whose sequence is not perfectly complementary to a particular target sequence. The mismatch may comprise one or more bases. While the mismatch(es) may be located anywhere in the mismatch probe, terminal mismatches are less desirable because a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

As used herein, the term "nucleic acid" refers to both naturally-occurring molecules such as DNA and RNA, but also various derivatives and analogs. Generally, the probes, hairpin linkers, and target polynucleotides of the present teachings are nucleic acids, and typically comprise DNA. Additional derivatives and analogs can be employed as will be appreciated by one having ordinary skill in the art.

The term "nucleotide base", as used herein, refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases adenine, guanine, cytosine, 6 methyl-cytosine, uracil, thymine, and analogs of the naturally occurring nucleotide bases, e.g., 7-deazaadenine, 7-deazaguanine, 7-deaza-8-azaguanine, 7-deaza-8-azaadenine, N6 delta 2-isopentenyladenine (6iA), N6-delta 2-isopentenyl-2-methylthioadenine (2 ms6iA), N2-dimethylguanine (dmG), 7methylguanine (7mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, 06-methylguanine, N6-methyladenine, 04-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385-394, CRC Press, Boca Raton, Fla., and the references cited therein.

The term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR2 or halogen groups, where each R is independently H, C1-C6 alkyl or C5-C14 aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-anomeric nucleotides, 1'-anomeric nucleotides, 2'-4'- and 3'-4'-linked and other "locked" or "LNA", bicyclic sugar modifications (see, e.g., PCT published application nos. WO 98/22489, WO 98/39352; and WO 99/14226). The term "nucleic acid" typically refers to large polynucleotides.

The term "nucleotide analogs" as used herein refers to modified or non-naturally occurring nucleotides including, but not limited to, analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner and herein incorporated by reference); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242; B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include nucleotides having one or more modification son the phosphate moiety, base moiety or sugar moiety, such as dideoxy nucleotides and 2'-O-methyl nucleotides. Nucleotide analogs include modified forms of deoxyribo-nucleotides as well as ribonucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning and amplification technology, and the like, and by synthetic means. An "oligonucleotide" as used herein refers to a short polynucleotide, typically less than 100 bases in length.

Conventional notation is used herein to describe polynucleotide sequences: the left-hand end of a single-stranded polynucleotide sequence is the 5'-end. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences." In the sequences described herein:

A=adenine,
G=guanine,
T=thymine,
C=cytosine,
U=uracil,

H=A, C or T/U,
R=A or G,
M=A or C,
K=G or T/U,
S=G or C,
Y=C or T/U,
W=A or T/U,
B=G or C or T/U,
D=A or G, or T/U,
V=A or G or C,
N=A or G or C or T/U.

The skilled artisan will understand that all nucleic acid sequences set forth herein throughout in their forward orientation, are also useful in the compositions and methods of the invention in their reverse orientation, as well as in their forward and reverse complementary orientation, and are described herein as well as if they were explicitly set forth herein.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, e.g., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with a detectable label, e.g., chromogenic, radioactive, or fluorescent moieties and used as detectable moieties. Examples of fluorescent moieties include, but are not limited to, rare earth chelates (europium chelates), Texas Red, rhodamine, fluorescein, dansyl, phycoerytherin, phycocyanin, spectrum orange, spectrum green, and/or derivatives of any one or more of the above. Other detectable moieties include digoxigenin and biotin.

As used herein a "probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, a linkage other than a phosphodiester bond may join the bases in probes, so long as it does not interfere with hybridization. Thus, probes may be peptide nucleic acids in which the constituent bases are joined by peptide bonds rather than phosphodiester linkages. The term "match," "perfect match," "perfect match probe" or "perfect match control" refers to a nucleic acid that has a sequence that is perfectly complementary to a particular target sequence. The nucleic acid is typically perfectly complementary to a portion (subsequence) of the target sequence. A perfect match (PM) probe can be a "test probe", a "normalization control" probe, an expression level control probe and the like. A perfect match control or perfect match is, however, distinguished from a "mismatch" or "mismatch probe."

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, oligonucleotides and nucleic acids.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention provides compositions and method for modifying 3' terminal ends of DNA and RNA using Polθ. In one embodiment, the invention provides a method for modification of the 3' terminal ends of a nucleic acid with a substrate by Polθ.

In one embodiment, the Polθ possesses robust template-independent terminal transferase activity exclusively in the presence of manganese. In another embodiment, Polθ possesses robust template-independent terminal transferase activity exclusively in the presence of cobalt. In one embodiment, the Polθ of the invention is more effective in transferring ribonucleotides and modified nucleotides to ssDNA compared to commercially available terminal deoxynucleotidyl transferase (TdT). In one embodiment Polθ synthesizes a nucleic acid containing a specific sequence.

Genetic Modification

In one embodiment, the invention provides recombinant Polθ. In some aspects, the invention includes an isolated protein (e.g. Polθ), wherein the protein is used to modify 3'-terminal ends of nucleic acids. In some embodiments, the isolated protein is an A family polymerase. In other embodiments, the protein is Polθ. In yet another embodiment, the protein is a fragment or active mutant of Polθ. In certain embodiments, the protein is $Polθ_{1792-2590}$ having the amino acid sequence of SEQ ID NO 1.

In one embodiment, the invention included a recombinant Polθ. Thus, the invention encompasses compositions and methods for producing recombinant Polθ, including but is not limited to, expression vectors, methods for the introduction of exogenous DNA into cells with concomitant expression of the exogenous DNA in the cells, and methods of protein modification, expression and isolation, such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York). In some embodiments Polθ is encoded by the human POLQ gene. In some embodiments Polθ is encoded by the C. elegans polq-1 gene. In some embodiments Polθ is encoded by the mouse Polq gene.

In some embodiments, the protein is a fragment or mutant of a protein which is able to modify the 3'-terminal DNA end. Therefore, another embodiment of the invention is to provide an isolated nucleic acid molecule that code for the protein fragment or the mutated protein. According to the invention, the protein fragment or mutated protein is obtained by mutating the wild type protein coding sequence. The mutagenesis technique could be by chemical, error prone PCR or site-directed approach. The suitable technique can be selected and used for introducing mutations and the mutated nucleic acid molecule can be cloned and expressed and the transferase activity of the protein can be determined.

The isolated nucleic acid sequence encoding the protein fragment or mutated protein can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA and RNA. For example, in one embodiment, the composition comprises an isolated DNA molecule, including for example, an isolated cDNA molecule, encoding the mutated protein, or functional fragment thereof. In one embodiment, the composition comprises an isolated RNA molecule encoding the mutated protein, or a functional fragment thereof.

The desired polynucleotide can be cloned into a number of types of vectors. However, the present invention should not be construed to be limited to any particular vector. Instead, the present invention should be construed to encompass a wide plethora of vectors which are readily available and/or well-known in the art. For example, a desired polynucleotide of the invention can be cloned into a vector including, but not limited to a plasmid, a phagemid, a phage derivative, an animal viruses, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

For expression of the desired polynucleotide, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928, 906). Furthermore, it is contemplated the control sequences that direct transcription and/or expression of sequences within non-nuclear organelles such as fmitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2001). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

One such promoter sequence is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In the context of an expression vector, the vector can be readily introduced into a host cell, e.g., mammalian, bacterial, yeast or insect cell by any method in the art. For example, the expression vector can be transferred into a host cell by physical, chemical or biological means. It is readily understood that the introduction of the expression vector comprising the polynucleotide of the invention yields a silenced cell with respect to a regulator.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Any DNA vector or delivery vehicle can be utilized to transfer the desired polynucleotide to a cell in vitro or in vivo. In the case where a non-viral delivery system is utilized, a preferred delivery vehicle is a liposome. The above-mentioned delivery systems and protocols therefore can be found in Gene Targeting Protocols, 2 ed., pp 1-35 (2002) and Gene Transfer and Expression Protocols, Vol. 7, Murray ed., pp 81-89 (1991).

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine nucleic acid complexes.

Transformation refers to the transfer of a nucleic acid (e.g., exogenous nucleic acid) into the genome of a host microorganism, resulting in genetically stable inheritance. Host microorganisms containing the transformed nucleic acid are referred to as "non-naturally occurring" or "recombinant" or "transformed" or "transgenic" microorganisms. Host microorganisms may be selected from, and the non-naturally occurring microorganisms generated in, any prokaryotic or eukaryotic microbial species from the domains of Archaea, Bacteria, or Eukarya. Exemplary bacteria include *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungal species include *Saccharomyces cerevisiae, Schizosaccharomyces pombe, Kluyveromyces lactis, Kluyveromyces marxianus, Aspergillus terreus, Aspergillus niger, Rhizopus arrhizus, Rhizopus oryzae, Candida, Yarrowia, Hansenula, Pichia pastoris, Torulopsis, Rhodotorula* and *Yarrowia lipolytica*. It is understood that any suitable host microorganism can be used to introduce suitable genetic modifications (e.g., an exogenous nucleic acid encoding an enzyme with methane monooxygenase activity that is stable in the presence of a chemical or environmental stress) to produce a non-naturally occurring microorganism as provided in the specification.

Reference proteins or nucleic acids, also known as "wild type" or "parent" proteins and nucleic acids are used as starting molecules for genetic engineering of variant enzymes with the desired stability.

Expression of recombinant proteins is often difficult outside their original host. For example, variation in codon usage bias has been observed across different species of bacteria (Sharp et al., 2005, Nucl. Acids. Res. 33:1141-1153). Over-expression of recombinant proteins even within their native host may also be difficult. In certain embodiments of the invention, nucleic acids (e.g., a nucleic acid encoding an enzyme with transferase activity that is stable in the presence of a chemical or environmental stress) that are to be introduced into microorganisms according to any of the embodiments disclosed herein may undergo codon optimization to enhance protein expression. Codon optimization refers to alteration of codons in genes or coding regions of nucleic acids for transformation of an organism to reflect the typical codon usage of the host organism without altering the polypeptide for which the DNA encodes. Codon optimization methods for optimum gene expression in heterologous organisms are known in the art and have been previously described (see., e.g., Welch et al., 2009, PLoS One 4:e7002; Gustafsson et al., 2004, Trends Biotechnol. 22:346-353; Wu et al., 2007, Nucl. Acids Res. 35:D76-79; Villalobos et al., 2006, BMC Bioinformatics 7:285; U.S. Patent Publication 2011/0111413; and U.S. Patent Publication 2008/0292918).

The protein of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The peptide may alternatively be made by recombinant means or by cleavage from a longer polypeptide.

The *Escherichia coli* (*E. coli*) Rosetta2(DE3)/pLysS strains, or other *E. coli* strains, may be transformed with a vector to express the modified protein and expressed in a flask or fermenter. The cells may be grown in the autoinduction medium (1× Terrific Broth, 0.5% w/v glycerol, 0.05% w/v dextrose, 0.2% w/v alpha-lactose, 100 µg/ml ampicillin and 34 µg/ml chloramphenicol) and cells harvested anytime between 60 to 70 hours after inoculation.

The cell pellet obtained by fermentation or centrifugation may be lysed after addition of suitable amount of resuspension buffer, by any method not limited to sonication, high pressure homogenization, bead mill, freeze thawing or by addition of any chemical.

According to the invention, the enzyme produced by fermentation may be enriched to obtain enzyme as usable for the transferase activity, by one or combination of methods. Methods of protein purification are known in the art. See, for example, Sambrook et al. (2001, Molecular Cloning: A Laboratory Manual, Cold Spring Harbor Laboratory, New York). The methods may involve binding of the protein to any matrix with diethylaminoethyl (DEAE) or other weak anion exchange functional group in the presence of Tris buffer or phosphate buffer and eluting with 0.4M sodium chloride (NaCl) solution. Alternatively, the methods may involve binding of the protein to matrix with $Ni^{2+}$ or other divalent metal cation affinity functional group in the presence of Tris buffer or phosphate buffer, or other buffer, and eluting with 0.5 M or other concentrations of Imidazole solution. An alternate method may involve addition of 0.3% (v/w) of polyethylenimine (PEI) to cell lysate and trapping the enzyme in the formed pellet, or releasing the enzyme from the pellet in to solution with the addition of 0.4M NaCl. In yet another alternate method 0.1% (v/v) PEI may be added stirred for suitable time, preferably 1 hour and centrifuged. To the centrifugate 60% ammonium sulfate (w/w) may be added, followed by stirring over a period of time and centrifuged. The pellet obtained with the active protein may be used for further processing. The active protein thus obtained from any of the above processes may be used as solution or as lyophilized solid or as an immobilized solid or as a granule.

The composition of a protein may be confirmed by amino acid analysis or sequencing.

The variants of the proteins according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally or chemically modified. Such variants are deemed to be within the scope of those skilled in the art from the teaching herein.

As known in the art the "similarity" between two peptides is determined by comparing the amino acid sequence and its conserved amino acid substitutes of one polypeptide to a sequence of a second polypeptide. Variants are defined to include peptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to stimulate the differentiation of a stem cell into the osteoblast lineage. The present invention includes amino acid sequences that are at least 60%, 65%, 70%, 72%, 74%, 76%, 78%, 80%, 90%, or 95% similar or identical to the original amino acid sequence. The degree of identity between two peptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The proteins of the invention can be post-translationally modified. For example, post-translational modifications that fall within the scope of the present invention include signal peptide cleavage, glycosylation, acetylation, isoprenylation, proteolysis, myristoylation, parylation, ubiquitylation, sumolation, phosphorylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The proteins of the invention may include unnatural amino acids formed by post-translational modification or by introducing unnatural amino acids during translation. A variety of approaches are available for introducing unnatural amino acids during protein translation.

A peptide or protein of the invention may be conjugated with other molecules, such as proteins, to prepare fusion proteins. This may be accomplished, for example, by the synthesis of N-terminal or C-terminal fusion proteins provided that the resulting fusion protein retains the functionality of the transferase.

A peptide or protein of the invention may be phosphorylated using conventional methods such as the method described in Reedijk et al. (The EMBO Journal 11(4):1365, 1992).

Nucleic Acids and Substrates

In one aspect, the invention provides nucleic acids which can be modified to add a substrate on the 3'-terminal ends by Polθ. The nucleic acids as well as the substrate of the invention may be from any source. Nucleic acid in the context of the present invention includes but is not limited to deoxyribonucleic acid (DNA), ribonucleic acid (RNA) and peptide nucleic acid (PNA). DNA and RNA are naturally occurring in organisms, however, they may also exist outside living organisms or may be added to organisms. The nucleic acid may be of any origin, e.g., viral, bacterial, archae-bacterial, fungal, ribosomal, eukaryotic or prokaryotic. It may be nucleic acid from any biological sample and any organism, tissue, cell or sub-cellular compartment. It may be nucleic acid from any organism. The nucleic acid may be pre-treated before quantification, e.g., by isolation, purification or modification. Also artificial or synthetic nucleic acid may be used. The length of the nucleic acids may vary. The nucleic acids may be modified, e.g. may comprise one or more modified nucleobases or modified sugar moieties (e.g., comprising methoxy groups). The backbone of the nucleic acid may comprise one or more peptide bonds as in peptide nucleic acid (PNA). The nucleic acid may comprise a base analog such as non-purine or non-pyrimidine analog or nucleotide analog. It may also comprise additional attachments such as proteins, peptides and/or or amino acids.

In one embodiment, the nucleic acid comprises single stranded DNA (ssDNA), double stranded DNA (dsDNA), partial ssDNA (pssDNA), RNA, and telomeric ssDNA. In one embodiment, the substrate is transferred to the 3'-end of the ssDNA, pssDNA, RNA, telomeric ssDNA or dsDNA.

In one embodiment, the substrate is dATP, dGTP, dCTP, dATP, dUTP, or a nucleotide analog. In some embodiments, a nucleotide or nucleotide analog can be labeled. Examples of possible labels include, but are not limited to a radioisotope, an enzyme, an enzyme cofactor, an enzyme substrate, an enzyme inhibitor, a dye, a hapten, a chemiluminescent molecule, a fluorescent molecule, a phosphorescent molecule, an electrochemiluminescent molecule, a chromophore, a magnetic particle, an affinity label, a chromogenic agent, an azide group or other groups used for click chemistry, and other moieties known in the art.

In one embodiment, the substrate is a deoxyribonucleotide or ribonucleotide modified at one or more positions within the sugar moiety, tri-phosphate moiety or base moiety. In one embodiment, the deoxyribonucleotide or ribonucleotide sugar moiety is modified. In one embodiment, the deoxyribonucleotide or ribonucleotide tri-phosphate moiety is modified. In one embodiment the deoxyribonucleotide or ribonucleotide base moiety is modified.

In certain embodiments, the substrate is cy3-dUTP, Digoxigenin-11-dUTP, Biotin-16AA-dUTP, Texas Red-5-dCTP, Cyanine 3-AA-UTP, 4-Thio-UTP, Biotin-16-AACTP, Ganciclovir Triphosphate, N6-(6-Azido)hexyl-adenosine-5'-triphosphate, or 5-Hydroxymethyl-2'-deoxyuridine-5'-Triphosphate. In some embodiments, the substrate is a 3'-O-blocked or 3'-unblocked reversible nucleotide terminator.

Methods

In one aspect, the invention provides methods of generating 3'-terminal end modified nucleic acid with a substrate. The method comprises: providing an A family member polymerase and a substrate; forming a mixture comprising the A family member polymerase, the substrate or mixture of different substrates, the nucleic acid, and a reaction solution wherein the reaction mixture comprises at least one divalent metal; incubating the mixture; and isolating the 3'-terminal end modified nucleic acid.

In one embodiment, the divalent metal is Manganese ($Mn^{2+}$) or Cobalt ($Co^{2+}$). In certain embodiments, the divalent metal is $Mn^{2+}$. In some embodiments the concentration of the divalent metal in the reaction solution is 1-50 mM, preferably 2-5 mM, and preferably 5 mM. In certain embodiments, a mixture of divalent metals including, but not limited to, $Mn^{2+}$ and magnesium $Mg^{2+}$ are used.

In one embodiment, the reaction solution further comprises a buffer. In certain embodiments, the buffer is Tris HCl. In some embodiments the pH of the buffer is 6.5-8.8, preferably 7.0-8.2 and preferably 8.2.

In one embodiment, the reaction solution further comprises glycerol. In some embodiments the concentration of glycerol in the reaction solution is less than 20%, preferably 10%.

In one embodiment, the reaction solution further comprises a non-ionic detergent. In certain embodiments, the non-ionic detergent is NP-40. In some embodiments the concentration of NP-40 in the reaction solution is less than 1%, preferably 0.1%.

In one embodiment, the reaction solution further comprises bovine serum albumin (BSA). In some embodiments the concentration of BSA in the reaction solution is 0.1 mg/ml.

In some embodiments, the step incubating the mixture comprises incubating the mixture at a controlled temperature for a controlled length of time. In certain embodiments, the incubation temperature is 25° C.-42° C. In some embodiments, the temperature is 25° C., 37° C. or preferably 42° C. In some embodiments, the incubation time is at least 2 hours. In certain embodiments, the incubation time is 2 hours.

In some embodiments, the ratio of A-family polymerase to nucleic acid is defined. In certain embodiments, the molar ratio of Pol:nucleic acid is at least 1:1, preferably 5:1.

The modified DNA product that comprises the nucleic acid and substrate can be isolated or amplified using a primer that corresponds to a primer binding site present in the ligated product (i.e., primer binding site present in the donor molecule or the resulting hybrid product).

In particular embodiments of the invention the quantifying steps comprise a method selected from the group consisting of gel electrophoresis, capillary electrophoresis, labelling reactions with subsequent detection measures and quantitative real-time PCR or isothermal target amplification.

In preferred embodiments of the invention the substrate is labelled with one or more fluorescent dye(s) and/or quencher(s) and wherein the quantifying steps comprise detecting fluorescence signals in the sample.

Particularly, the fluorescently labelled primers or probes are labelled with a dye selected from the group consisting of FAM, VIC, NED, Fluorescein, FITC, IRD-700/800, CY3, CY5, CY3.5, CY5.5, HEX, TET, TAMRA, JOE, ROX, BODIPY TMR, Oregon Green, Rhodamine Green, Rhodamine Red, Texas Red, Yakima Yellow, Alexa Fluor and PET or analogous dyes with similar excitation and emission properties.

In one embodiment, the primer or probe is a LightCycler probe (Roche) or the hydrolysis probe is a TaqMan probe (Roche). In other embodiments the primer or probe includes but is not limited to molecular beacon, Scorpion primer, Sunrise primer, LUX primer and Amplifluor primer.

The ability of Polθ to transfer various types of nucleotide analogs to the 3' terminus of nucleic acids demonstrates this enzyme can be utilized to synthesize nucleic acids of specific sequence and length.

Accordingly, in another aspect, the invention provides methods of de novo synthesis of nucleic acids. The method comprises: providing an A family member polymerase and a substrate; forming a mixture comprising the A family member polymerase, at least one nucleobase, and a reaction solution wherein the reaction mixture comprises at least one divalent metal; incubating the mixture; and isolating the synthesized nucleic acid.

In one embodiment, Polθ synthesizes nucleic acid by transferring nucleotides the 3' terminus of a nucleic acid.

In one embodiment, the length of the synthesized nucleic acid is controlled by consecutive transfer of nucleobases via individual steps.

In one embodiment, the sequence of the synthesized nucleic acid is controlled by consecutive transfer of specific nucleobases, wherein the addition of specific of nucleobases during ordered individual transfer steps dictates the synthesized nucleic sequence.

In one embodiment, the A family polymerase is Polθ. In some embodiments, the at least one nucleobase is selected from ATP, UTP, GTP, dATP, dTTP, dGTP, dCTP, and any combination thereof.

In another embodiment, the nucleotides are 3'-O-blocked or 3'-unblocked reversible terminators. In one embodiment, the reversible terminator allows for multiple controlled consecutive single nucleotide transfer events in a DNA or RNA sequence dependent manner.

In some embodiments, the step incubating the mixture comprises incubating the mixture at a controlled temperature for a controlled length of time. In certain embodiments, the incubation temperature is 25° C.-42° C. In some embodiments, the temperature is 25° C., 37° C. or preferably 42° C. In some embodiments, the incubation time from about 30 minutes to about 2 hours. In certain embodiments, the incubation time is 2 hours.

Applications

The modified DNA or RNA composition of the present invention may be used in a wide variety of protocols and technologies. For example, in certain embodiments, the modified DNA or RNA is used in the fields of molecular biology, genomics, transcriptomics, epigenetics, nucleic acid synthesis, nucleic acid sequencing, and the like. That is, modified DNA or RNA may be used in any technology that may require or benefit from the ligation, attachment or synthesis of modified DNA or RNA.

This method can be used in many technology platforms, including but not limited to microarray, bead, and flow cytometry. The method will be useful in numerous applications, such as genomic research, drug target validation, drug discovery, diagnostic biomarker identification and therapeutic assessment.

Kits

The present invention also relates to a kit for performing any of the above described methods, wherein the kit comprises one or more of: (a) an A-family polymerase (b) a reaction solution and optionally, (c) a substrate to modify a nucleic acid.

In one embodiment, the kit additionally comprises a Polθ. In another embodiment, the kit additionally comprises a polymerase. The kit may additionally also comprise a nucleotide mixture and (a) reaction buffer(s). In certain embodiments, the kit includes a reaction buffer comprising 5 mM $Mn^{2+}$, 20 mM Tris HCl pH 8.2, 10% glycerol, 0.01% NP-40 and 0.1 mg/mL BSA.

In particular embodiments, the kit additionally comprises one or more pre-quantified calibrator nucleic acids, and a substrate for the modification of said calibrator nucleic acid.

In some embodiments, one or more of the components are premixed in the same reaction container.

EXPERIMENTAL EXAMPLES

The invention is further described in detail by reference to the following experimental examples. These examples are provided for purposes of illustration only, and are not intended to be limiting unless so specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: DNA Polymerase θ Exhibits Robust Template-Independent Terminal Transferase Activity in the Presence of Manganese The data presented herein determines that Polθ definitively exhibits template-independent terminal transferase activity in vitro. After trying various conditions, Polθ was found to perform robust template independent terminal transferase activity in a manner that depends on the presence of the divalent cation manganese ($Mn^{2+}$), or cobalt ($Co^{2+}$). In the presence of $Mn^{2+}$, this activity is highly efficient, resulting in the addition of hundreds of nucleotides to 3' termini of ssDNA, pssDNA, dsDNA and RNA ends. Moreover, Polθ was found to be more effective in transferring ribonucleotides and modified nucleotide analogs containing bulky functional groups to ssDNA than commercially available terminal deoxynucleotidyl transferase (TdT). Considering that Polθ dependent non-templated nucleotide insertions occur regularly during alt-NHEJ in vivo (Yousefzadeh et al., 2014, PLoS Genet 10:e1004654; Mateos-Gomez et al., 2015, Nature 518:254-7; Chan et al., 2010, PLoS Genet 6:e1001005; Koole et al., 2014, Nat Commun 5:3216), the template-independent terminal transferase activity discovered herein likely facilitates insertion mutations associated with alt-NHEJ in cells.

The materials and methods employed in these experiments are now described.

Protein Purification

Polθ (amino-acid residues 1792-2590) was purified as described (Kent et al., 2015, Nat Struct Mol Biol 22:230-7).

Polθ Terminal Transferase Activity

The following procedure describes optimal conditions for Polθ terminal transferase activity. 500 nM or 240 nM Polθ was incubated with 50 nM of the indicated radio-labeled DNA for 120 min at 42° C. in the presence of 0.5 mM dNTPs in a 10 µl volume of the following buffer (20 mM TrisHCl pH 8.2, 10% glycerol, 5 mM MnCl, 0.01% NP-40, 0.1 mg/ml BSA). Reactions were terminated by the addition of 20 mM EDTA and 45% formamide and DNA was resolved by electrophoresis in urea polyacrylamide gels then visualized by autoradiography. Polµ terminal transferase reactions were performed using the same conditions as Polθ.

TdT Terminal Transferase Activity

TdT terminal transferase reactions were performed using conditions recommended by New England Biolabs, however, 0.6 units/of TdT was used in order to compare its activity with identical concentrations of Polθ (240 nM); 0.6 units/µl is 3-fold more than that recommended by supplier. Supplier's recommended buffer and temperature conditions used for TdT were as follows: 50 mM potassium acetate, 20 mM Tris acetate, 10 mM magnesium acetate, pH 7.9, with 0.25 mM cobalt at 37° C. Incubation times were the same as Polθ.

The results of the experiments are now described.

Polθ Possesses Template-Independent Terminal Transferase Activity in the Presence of $Mn^{2+}$ and $Co^{2+}$ To determine whether Polθ definitively exhibits template-independent terminal transferase activity, the ability of Polθ to extend a homopolymeric ssDNA substrate composed exclusively of deoxycytidine-monophosphates (poly-dC) was tested. In previous studies, it was found that Polθ is only able to extend homopolynucleotide substrates in the presence of the complementary deoxy-ribonucleotide-triphosphate (dNTP) which demonstrates its ability to exclusively perform template dependent DNA synthesis (Kent et al., 2015, Nat Struct Mol Biol 22:230-7; Hogg et al., 2012, Nucleic Acid Res 40:2611-22). Considering that divalent cations other than $Mg^{2+}$ are present in cells, they may account for the discrepancy between the ability of Polθ to perform non-templated DNA synthesis in vivo but not in vitro. Therefore tested various divalent cations were tested in a reaction including Polθ, and a 5' radio-labeled poly-dC ssDNA substrate 29 nucleotides (nt) in length in the presence and absence of $Mg^{2+}$ (FIG. 1A). The results show that $Mn^{2+}$ and $Co^{2+}$ activate Polθ extension of poly-dC with deoxythymidine-triphosphate (dTTP) which demonstrates template-independent terminal transferase activity (i.e. non-templated DNA synthesis). Since $Mn^{2+}$ and $Co^{2+}$ had a greater stimulatory effect in the absence of $Mg^{2+}$, they likely bind the same position as $Mg^{2+}$ in the active site (FIG. 1A).

Figures 1C, 1D, 1E:
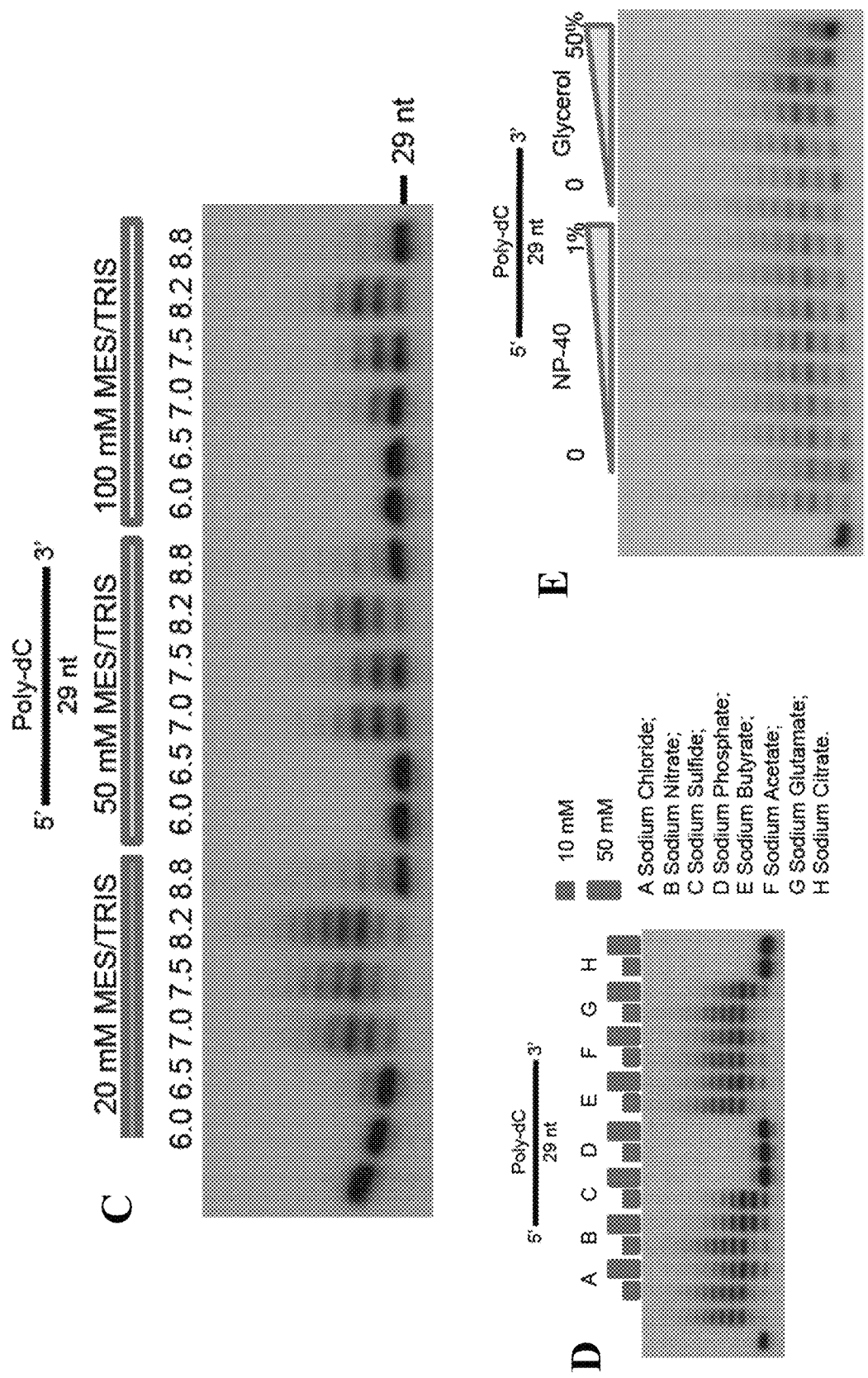

Polθ template-independent terminal transferase activity in the presence of $Mn^{2+}$ was further investigated since it showed a greater stimulatory effect than C2+. FIG. 1B shows that 2-5 mM $Mn^{2+}$ results in the most efficient extension of the poly-dC substrate in the presence of dTTP. The effects of different pH levels and buffer salt concentrations on Polθ template-independent terminal transferase activity were then examined. The results show that pH~8.2 is most amenable to this activity, and that a relatively high concentration of buffer salt is inhibitory (FIG. 1C). Next, how salts, glycerol and non-ionic detergent (NP-40) affect the observed Polθ template-independent terminal transferase activity was examined. Most of the salts had only a slight inhibitory effect at 50 mM concentration (FIG. 1D). Sodium sulfide, sodium phosphate and sodium citrate, however, significantly inhibited Polθ terminal transferase activity at lower concentrations (FIG. 1D). It was found that relatively high concentrations of glycerol inhibited this activity, whereas low amounts of non-ionic detergent slightly stimulated Polθ in this assay (FIG. 1E). Together, these data demonstrate that Polθ possesses template-independent terminal transferase activity in the presence of $Mn^{2+}$, and to a lesser extent with $Co^{2+}$, and begin to identify the optimal conditions under which the polymerase performs this novel function.

Optimization of Polθ Template-Independent Terminal Transferase Activity

Figures 2A, 2B:
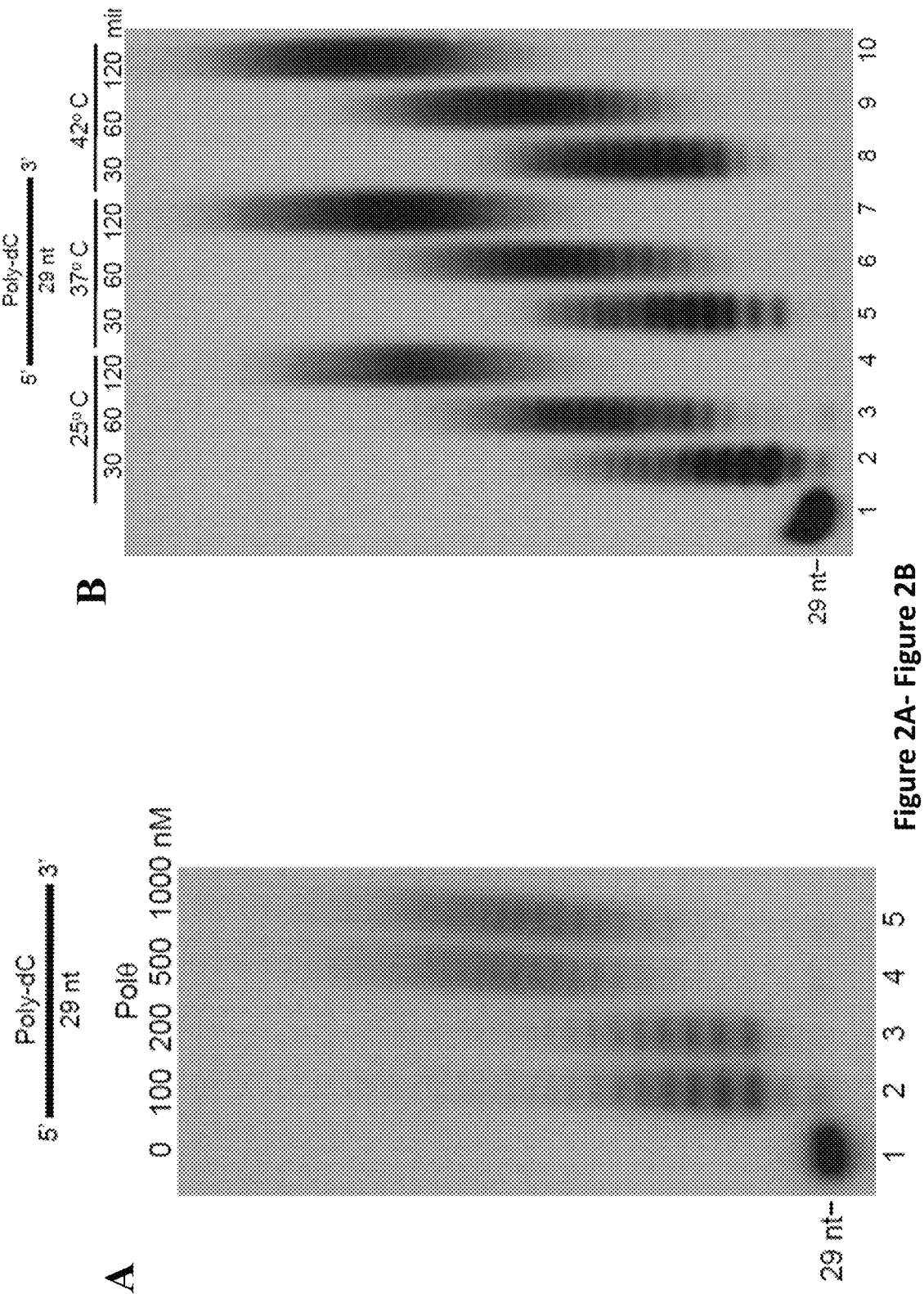
FIG. 2A and FIG. 2B, depicts results of experiments demonstrating the optimization of Polθ template-independent terminal transferase activity.

Next, it was determined whether the concentration of Polθ relative to ssDNA affects its template-independent terminal transferase activity. The results show that approximately a five-fold molar excess of the polymerase above ssDNA is needed for maximal terminal transferase activity (FIG. 2A). It was further found that maximal transferase activity requires at least 2 hours of incubation at the optimal temperature of 420° C. (FIG. 2B). Since these data were obtained on a poly-dC template in the presence of dTTP, they unequivocally demonstrate Polθ as possessing robust template-independent terminal transferase activity, and likely identify the optimal conditions for this process.

Polθ Exhibits Preferential Terminal Transferase Activity on ssDNA and pssDNA

Figures 3A, 3B:
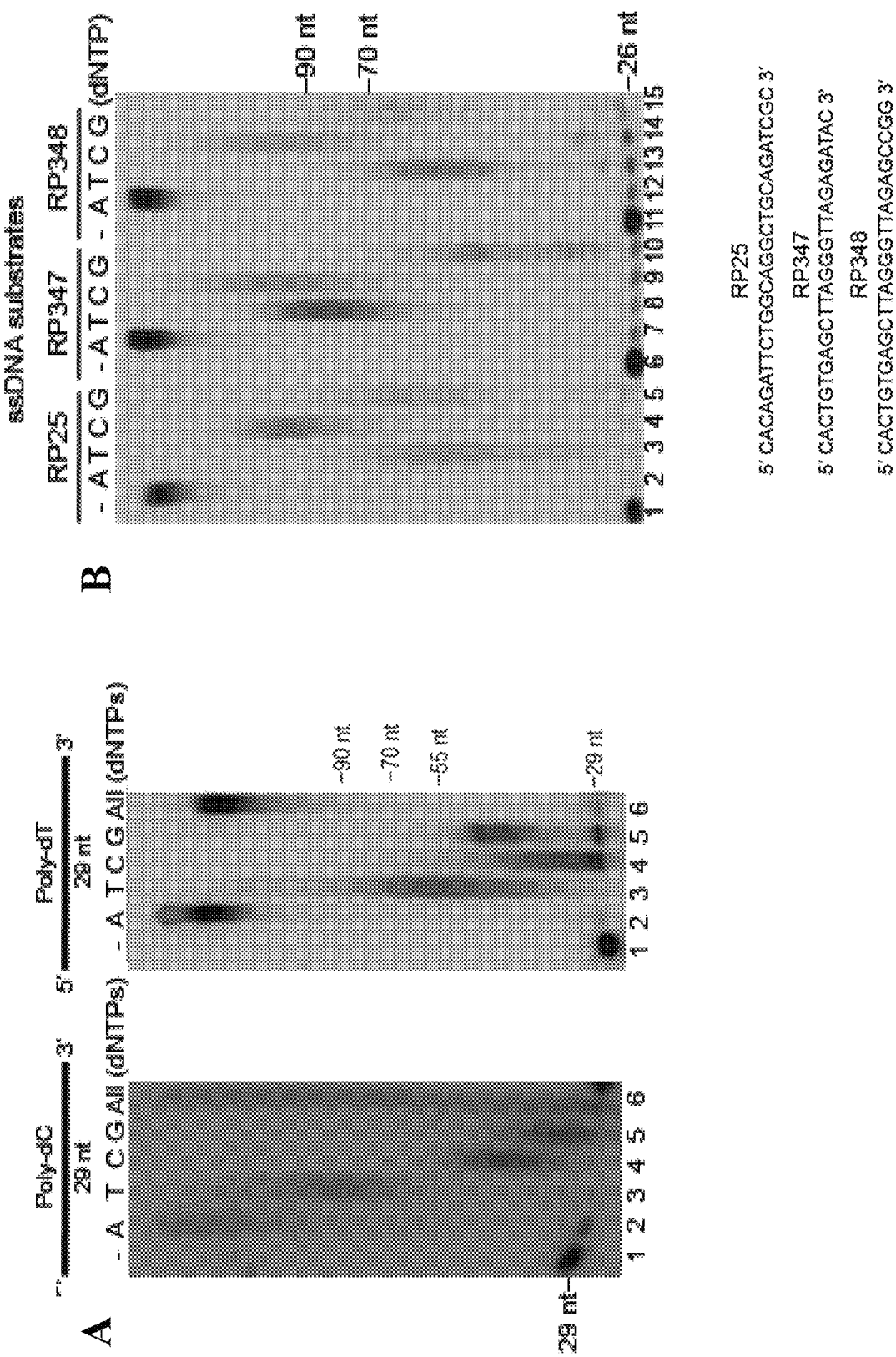
FIG. 3A through FIG. 3G, depicts results of experiments demonstrating that Polθ exhibits preferential terminal transferase activity on ssDNA and pssDNA.
Figures 3C, 3D, 3E:
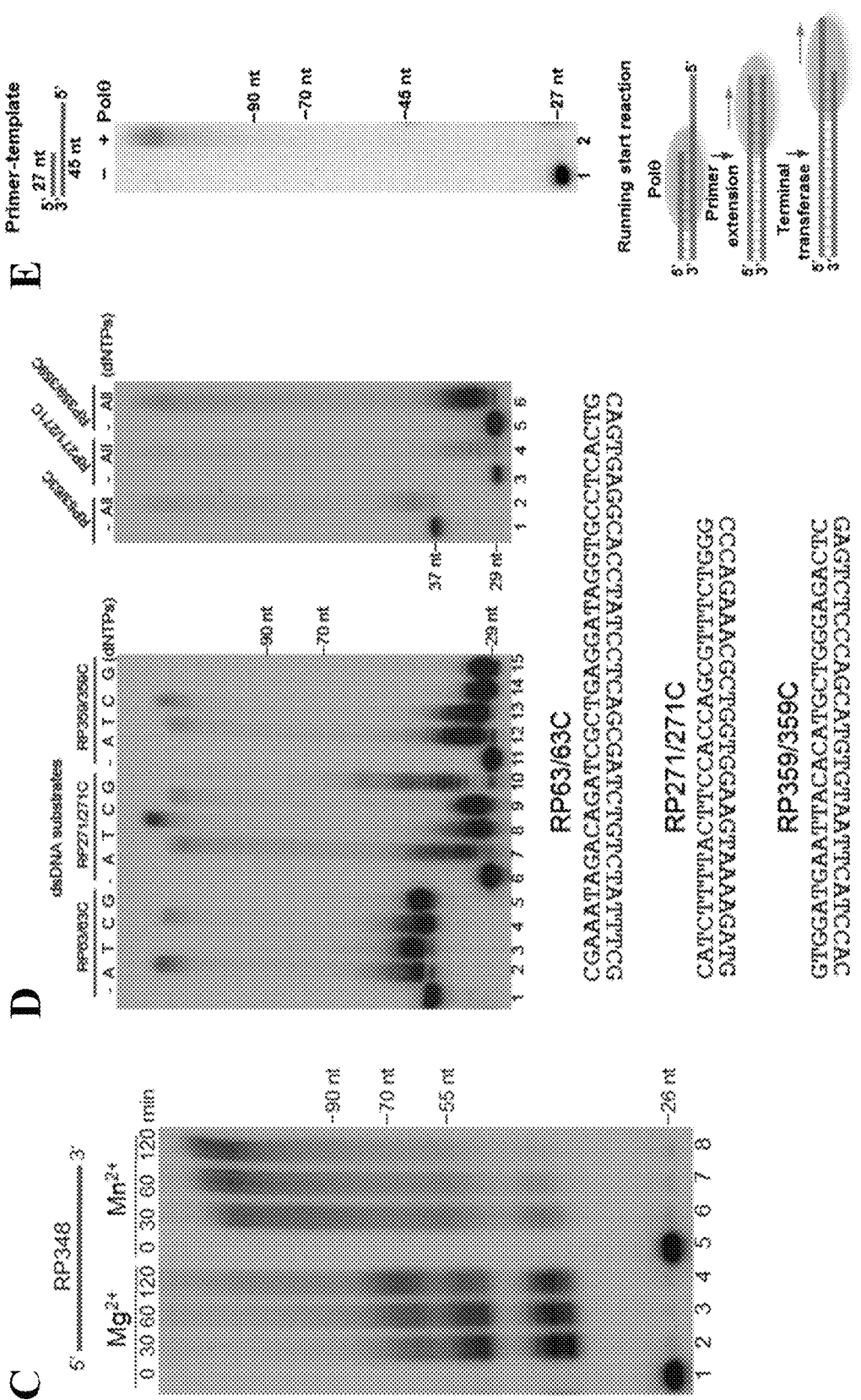

Next, the Polθ terminal transferase activity was examined in the presence of $Mn^{2+}$ on a variety of other substrates. For example, this activity was further tested on homopolymeric ssDNA composed of either deoxythymidine-monophosphates (poly-dT) or deoxycytidine-monophosphates (poly-dC), and ssDNA containing variable sequences. Interestingly, the polymerase preferentially extended these substrates by more than 100 nt in the presence of deoxyadenosine-triphosphate (dATP) regardless of the sequence context (FIGS. 3A and 3B). Considering that polymerases preferentially incorporate a deoxyadenosine-monophosphate (dAMP) opposite an abasic site, which is regarded as the A-rule, these data are consistent with Polθ template-independent activity. Polθ also extends ssDNA in the presence of dTTP, dCTP, and dGTP, however, the lengths of extension products are shorter than with dATP (FIGS. 3A and 3B). In the case of non-homopolymeric ssDNA, Polθ transfers ~30-70 nt in the presence of dTTP, dCTP, or dGTP, and transfers at least 100 nt when dATP is present (FIG. 3B). Interestingly, Polθ appears inefficient in terminal transferase activity on doublestrand DNA (dsDNA)(FIG. 3D). Here, only a small fraction of dsDNA substrates are extended which is in contrast to the results observed with ssDNA. Further experiments, however, show that Polθ efficiently extends dsDNA when a "running start" reaction is performed (FIG. 3E). For example, on a traditional primer-template substrate, Polθ extends the primer for hundreds of nucleotides past the 5' end of the template strand (FIG. 3E).

Figures 3F, 3G:
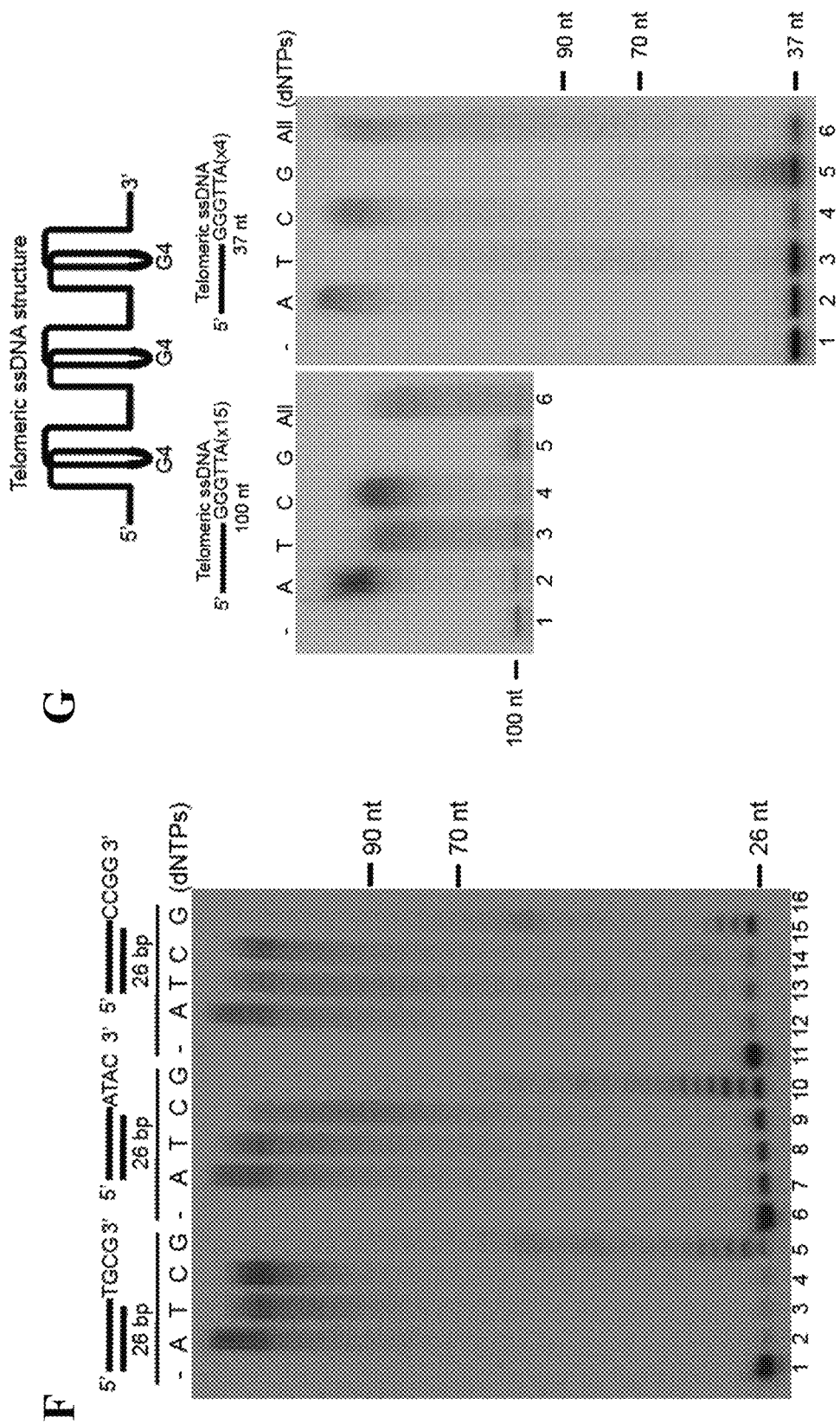

Considering that Polθ is thought to act on DSBs partially resected by Mre11 during MMEJ/alt-NHEJ3, its terminal transferase activity was examined on partial ssDNA (pssDNA) templates containing 3' overhangs. Remarkably, the polymerase exhibited the most efficient terminal transferase activity on pssDNA (FIG. 3F). For example, the polymerase extended these substrates to longer lengths with most dNTPs (compare FIG. 3F with FIG. 3B). However, in the presence of dGTP Polθ terminal transferase activity appears less efficient (FIG. 3F). Consistent with its role in promoting alt-NHEJ of telomeres in cells deficient in telomere protection proteins and non-homologous end-joining (NHEJ) factors (Mateos-Gomez et al., 2015, Nature 518: 254-7), Polθ also exhibits efficient terminal transferase activity on ssDNA modeled after telomeres which is known to contain stable G-quadruplex (G4) secondary structures (FIG. 3G). Here again extension in the presence of dGTP was the least efficient. Considering that multiple guanosines are present in the telomere repeat sequence, they likely suppress transfer of deoxyribonucloside-monophosphate (dGMP) by the polymerase. In contrast, all other nucleotides are efficiently transferred to the telomeric ssDNA substrate (FIG. 3G). Taken together, the results in FIG. 3 show that Polθ exhibits the most effective terminal transferase activity on pssDNA, which is consistent with its role in MMEJ/alt-NHEJ, and that the polymerase is also efficient in extending various ssDNA and dsDNA substrates.

Polθ, Polμ, and TdT Activities on ssDNA

Figures 4A, 4B:
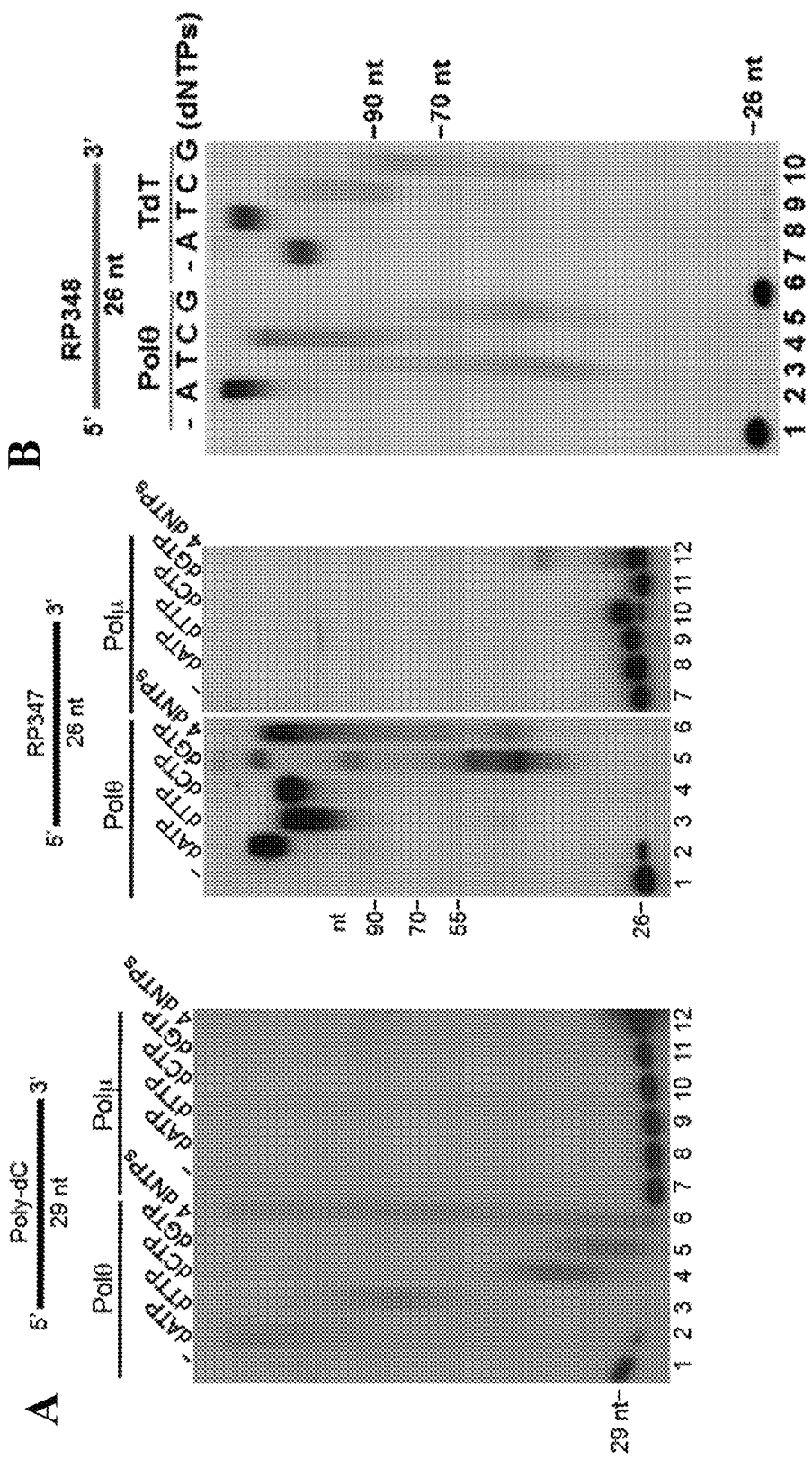
FIG. 4A through FIG. 4D, depicts results of experiments demonstrating a comparison of Polθ, Polµ, and TdT activities on ssDNA.

Previous studies have suggested that X-family Polμ, which promotes NHEJ, might exhibit template-independent terminal transferase activity in the presence of $Mn^{2+}$ (Dominguez et al., 2000, EMBO J 19:1731-42). However, a more recent report stated that Polμ lacks template-independent terminal transferase activity (MOLECULAR AND CELLULAR BIOLOGY, April 2003, p. 2309-2315). A direct compared was made between template-independent terminal transferase activities by Polθ and Polμ under identical conditions. The results show that Polμ lacks any observable template-independent terminal transferase activity on a poly-dC substrate (FIG. 4A, left). Pol terminal transferase activity is also very poor on a non-homopolymeric ssDNA compared to Polθ which adds hundreds of nucleotides under the same conditions (FIG. 4A, right). Hence, these data demonstrate that Polθ exhibits much more efficient terminal transferase activity than Polμ and provide an explanation of why longer insertions are observed at alt-NHEJ junctions compared to NHEJ junctions in cells.

Figures 4C, 4D:
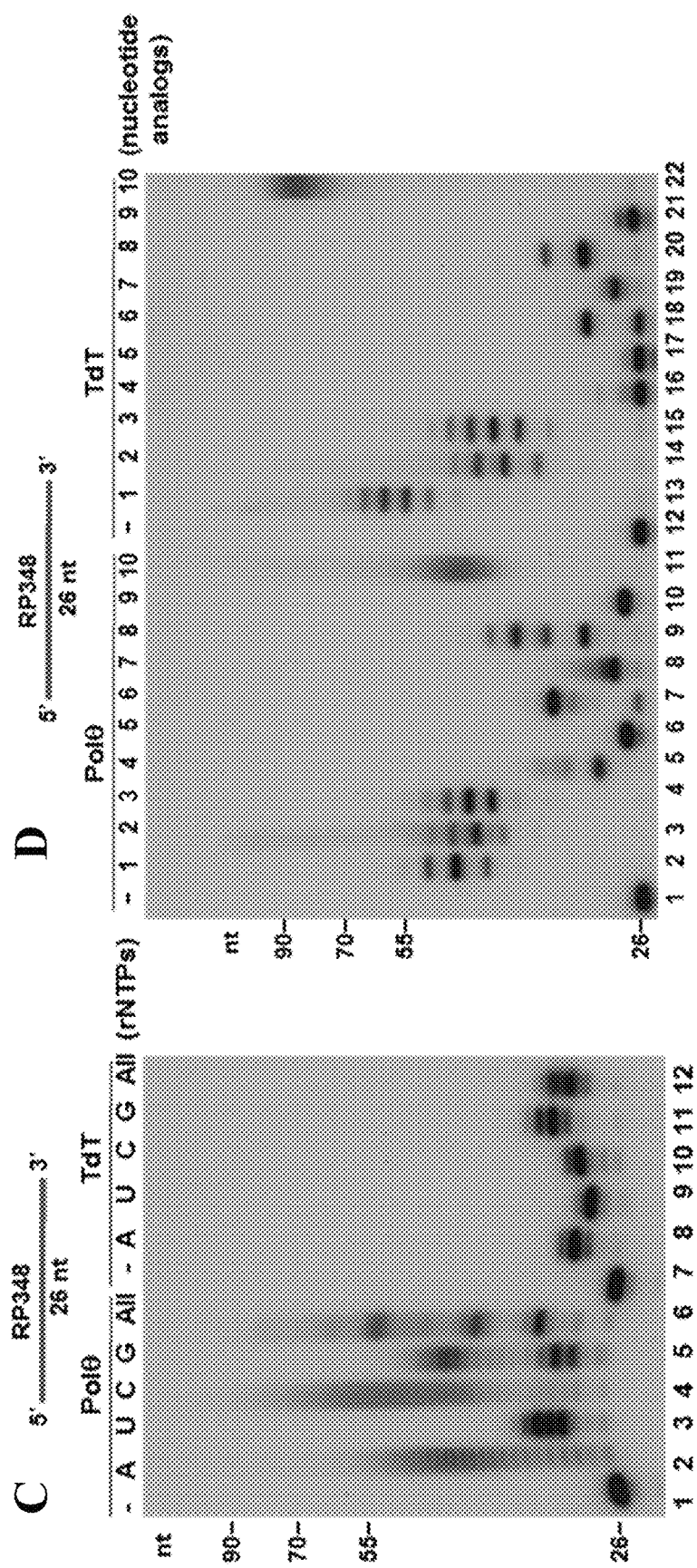
Figure 5:
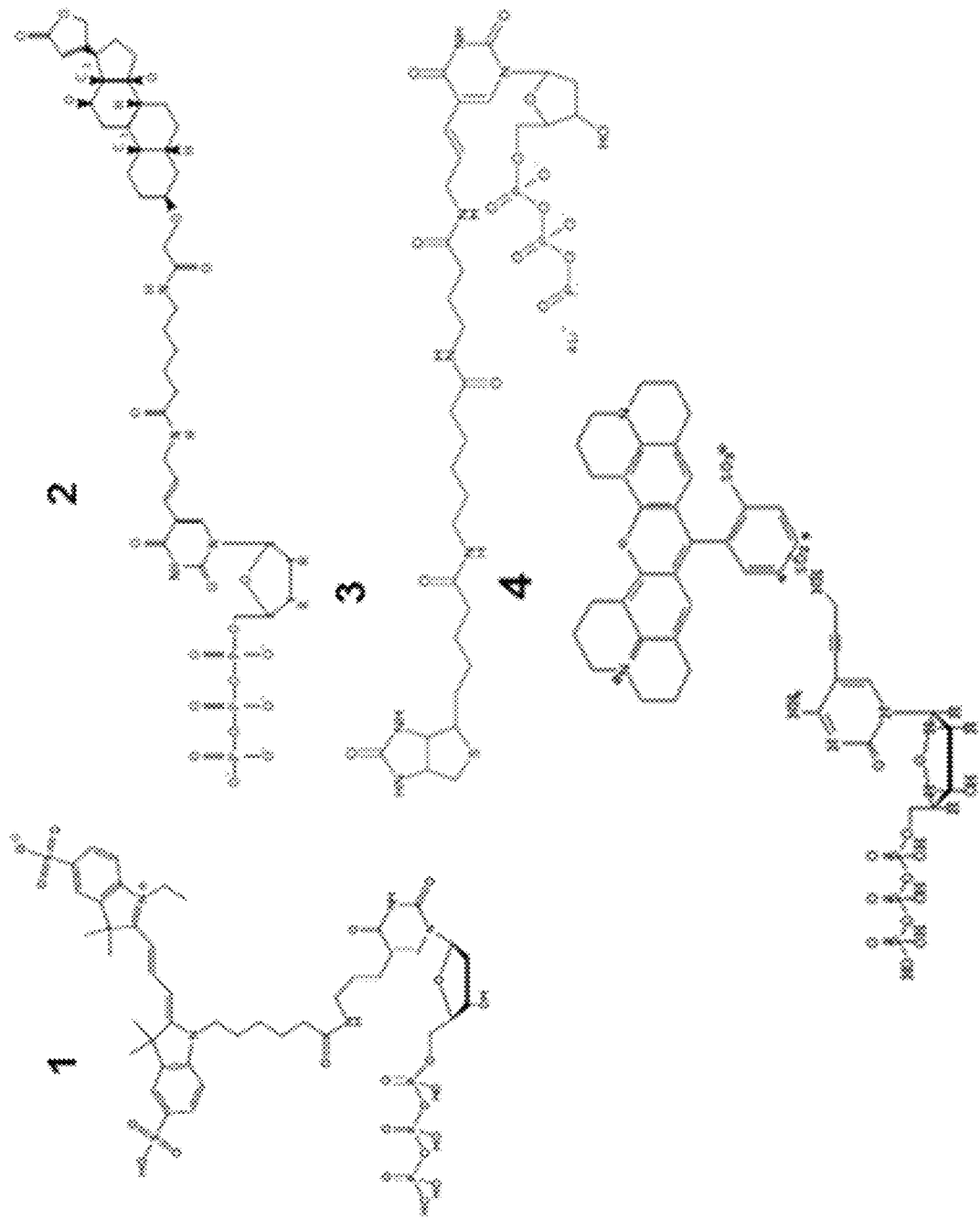
FIG. 5 is an image depicting the structures of modified nucleotides 1, cy3-dUTP; 2, Digoxigenin-11-dUTP; 3, Biotin-16AA-dUTP; 4, Texas Red-5-dCTP; 5, N6-(6-Azido)hexyl-ATP; 6, Cyanine 3-AA-UTP; 7, 4-Thio-UTP; 8, Biotin-16-AACTP; 9, Ganciclovir Triphosphate; and 10, 5-Hydroxymethyl-2'-deoxyuridine-5'-Triphosphate.
Figure 5:
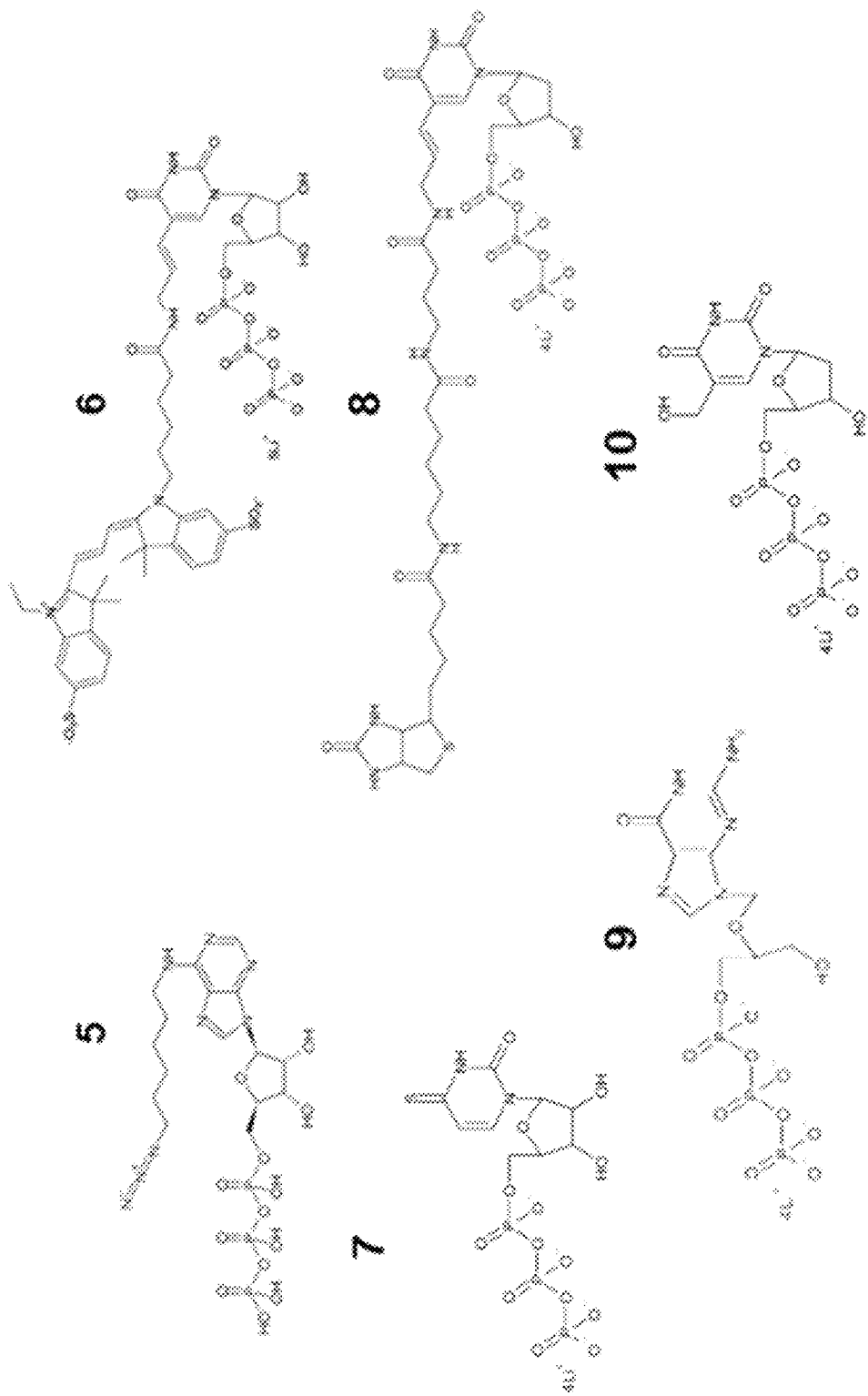

Importantly, terminal transferase activity is widely used to modify ssDNA ends for various types of applications including biotechnology, biomedical research, and synthetic biology. Currently, the only enzyme developed and marketed for these applications is terminal deoxynucleotidyl transferase (TdT) whose cellular function is to add non-templated nucleotides to V, D and J exon regions during antibody gene maturation (Moeta and Berdis, 2010, Biochim Biophys Acta 1804:1151-66). FIG. 4B compares the activities of Polθ and TdT. Remarkably, Polθ exhibits a similar ability to extend ssDNA as TdT assayed under conditions recommended by the supplier (New England Biolabs; FIG. 4B). The results also show that Polθ and TdT preferentially utilize dATP and dTTP, respectively, for this reaction (FIG. 4B). Many biotechnology and biomedical research applications require ssDNA substrates modified with fluorophores or other chemical groups, such as those that enable DNA attachment to solid surfaces or other types of molecules (see FIG. 5). Therefore the ability of Polθ to transfer deoxyribonucleotides and ribonucleotides conjugated with different functional groups to the 3' terminus of ssDNA was examined (see FIG. 5). Using the supplier's recommended buffer and temperature conditions for TdT, and identical concentrations of Polθ under the presently described optimal conditions for the polymerase, it was found that Polθ is significantly more effective in transferring ribonucleotides to ssDNA compared to TdT (FIG. 4C). Thus, although previous studies have shown that Polθ strongly discriminates against ribonucleotides (Hogg et al., 2012, Nucleic Acid Res 40:2611-22), this fidelity mechanism appears to be compromised during the presently described terminal transferase reaction. Again using the same conditions, it was unexpectedly found that Polθ more effectively transfers most (8 out of 10) modified deoxy-ribonucleotides and ribonucleotides to ssDNA than TdT (FIG. 4D). For example, in many cases Polθ transfers more modified nucleotides to ssDNA compared to TdT resulting in longer extension products (FIG. 4D, FIG. 5). In other cases, TdT completely fails to transfer certain modified nucleotides that Polθ efficiently adds to ssDNA (FIG. 4D). For example, Polθ efficiently transfers Texas Red dCTP, N6-dATP, and ganciclovir, whereas an identical concentration of TdT is unable to incorporate these modified nucleotides (FIG. 4D; FIG. 5). In general, many of these modified deoxyribonucleotides and ribonucleotides include long linkers attached to functional groups including biotin, digoxigenin, Cy3, and Texas Red (FIG. 5). Thus, these results show that Polθ can efficiently transfer ribonucleotides and deoxyribonucleotides containing large modifications on their base moieties (i.e. uracil, cytosine) and sugar modifications (i.e. ganciclovir mono-phosphate). Taken together, these data show that Polθ is more effective in transferring canonical ribonucleotides and modified ribonucleotide and deoxyribonucleotide analogs containing bulky groups compared to commercially available TdT. Considering that Polθ exhibits translesion synthesis activity, these results may be attributed to its natural ability to accommodate bulky nucleotides in its active site.

Figures 6A, 6B:
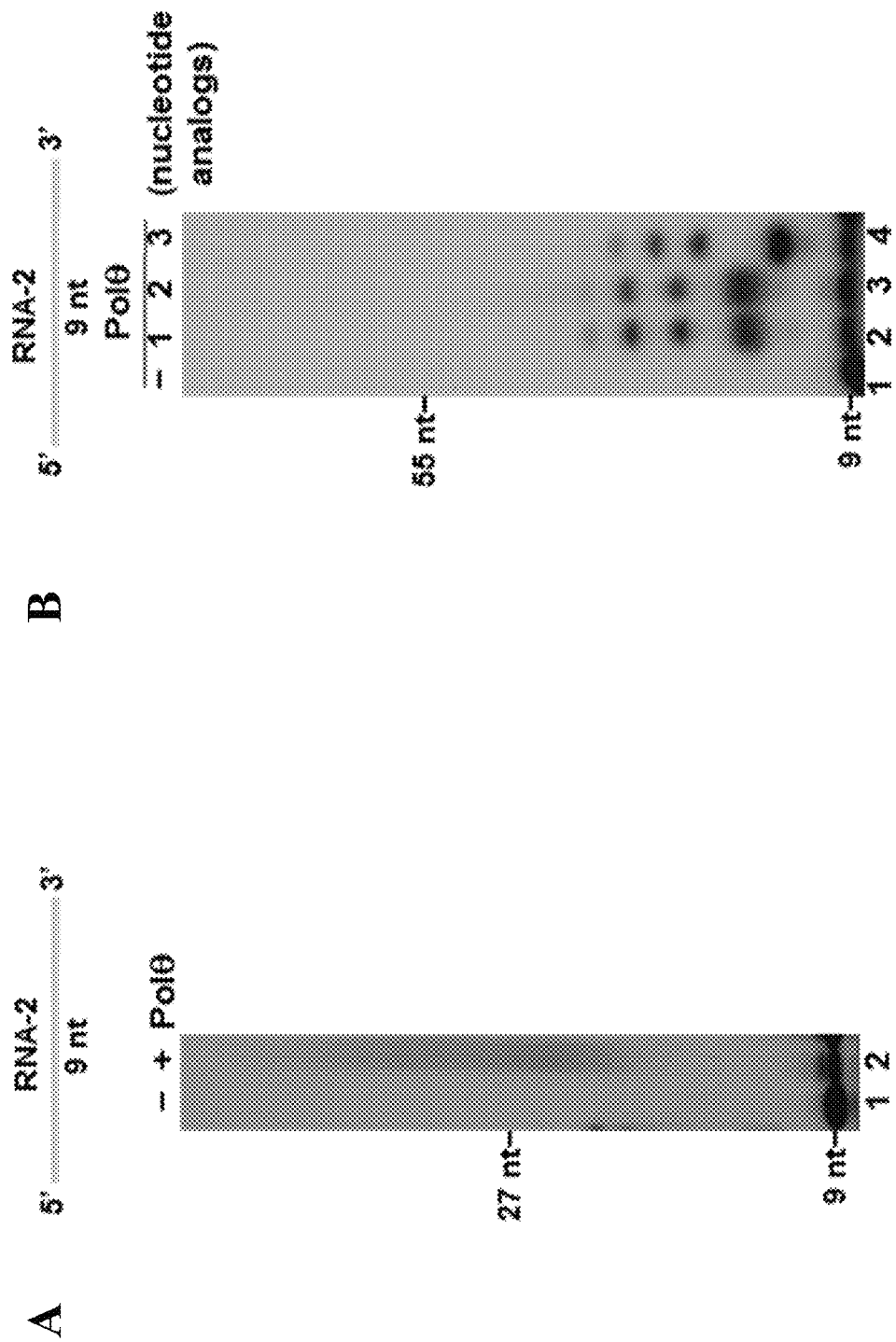
FIG. 6A and FIG. 6B, depicts results of experiments demonstrating that Polθ extends RNA with canonical and modified nucleotides.

Since RNA is increasingly being used for many types of applications in biotechnology and biomedical research, the ability of Polθ to modify the 3' terminus of RNA was further examined. It was observed that Polθ can transfer deoxyribonucleotides to the 3' terminus of RNA. Moreover, Polθ is capable of transferring modified nucleotides to RNA (FIG. 6B; FIG. 5). Hence, these results demonstrate that Polθ terminal transferase activity is not limited to DNA.

Polθ for Modifying Nucleic Acid Substrates

Polθ is an unusual A-family polymerase that is highly error-prone and promiscuous due to the presence of three insertion motifs in its otherwise conserved polymerase domain (Kent et al., 2015, Nat Struct Mol Biol 22:230-7; Hogg et al., 2011, J Mol Biol 405:642-52; Hogg et al., 2012, Nucleic Acid Res 40:2611-22; Arana et al., 2008, Nucleic Acid Res 36:3847-56; Zahn et al., 2015, Nat Struct Mol Biol 22:304-11). Recent studies have discovered that this enzyme is essential for MMEJ/alt-NHEJ in mammalian cells, which promotes chromosome rearrangements and resistance to DNA damaging agents, including those used for chemotherapy (Yousefzadeh et al., 2014, PLoS Genet 10:e1004654; Mateos-Gomez et al., 2015, Nature 518:254-7). Importantly, these previous cellular studies have shown the presence of non-templated (random) nucleotide insertions at DNA repair junctions generated by alt-NHEJ which were dependent on Polθ (Yousefzadeh et al., 2014, PLoS Genet 10:e1004654). Hence, these reports have indicated that Polθ generates random nucleotide insertions during alt-NHEJ, presumably via a template-independent terminal transferase activity. Yet, until now Polθ template-independent terminal transferase activity has not been demonstrated in vitro.

The data presented herein demonstrate that Polθ exhibits robust template-independent terminal transferase activity that is activated by the metal $Mn^{2+}$. Considering that differential binding of divalent cations within the active site of Polθ slightly alters its local conformation (Zahn et al., 2015, Nat Struct Mol Biol 22:304-11), $Mn^{2+}$ binding likely facilitates an active site conformation more favorable for non-templated DNA synthesis. Since Polθ non-templated nucleotide insertions are associated with alt-NHEJ in cells, these findings indicate that $Mn^{2+}$ is a co-factor of Polθ in vivo. For example, although $Mn^{2+}$ is present at significantly lower concentrations than $Mg^{2+}$ in cells (Martin et al., 2013, Nucleic Acid Res 41:2428-36), the data presented herein show that only a small amount of $Mn^{2+}$ is needed to stimulate Polθ template-independent terminal transferase activity when $Mg^{2+}$ is abundant (FIG. 1A). Thus, the relatively low cellular concentration of Mn (<1 mM) is likely to activate Polθ template-independent terminal transferase activity. Lastly, given that Polθ is more effective in transferring ribonucleotides and many modified nucleotide analogs containing large functional groups to the 3' terminus of ssDNA than identical concentrations of commercially available TdT assayed under the supplier's recommended optimal conditions, it is anticipated that Polθ will be more useful for modifying DNA as well as RNA substrates for biotechnology, biomedical research and synthetic biology applications. Moreover, since Polθ does not require toxic reaction components like TdT, such as $Co^{2+}$ salts or salts of cadodylic acid, Polθ terminal transferase assays are a safer option for research and biotechnology applications.

Example 2: Peptide and Nucleic Acid Sequences

Presented herein are the peptide sequences and the calculated nucleic acid sequences for the peptides. The amino acid sequences were calculated using EMBOSS Backtranambig—a program that reads a protein sequence and writes the nucleic acid sequence it could have come from. It does this by using nucleotide ambiguity codes that represent all possible codons for each amino acid (Table 1).

```
Polθ1792-2590
Amino acid sequence:
                                          (SEQ ID NO: 1)
GFKDNSPISDTSFSLQLSQDGLQLTPASSSSESLSIIDVASDQNLFQTFI

KEWRCKKRFSISLACEKIRSLTSSKTATIGSRFKQASSPQEIPIRDDGFP

IKGCDDTLVVGLAVCWGGRDAYYFSLQKEQKHSEISASLVPPSLDPSLTL

KDRMWYLQSCLRKESDKECSVVIYDFIQSYKILLLSCGISLEQSYEDPKV

ACWLLDPDSQEPTLHSIVTSFLPHELPLLEGMETSQGIQSLGLNAGSEHS

GRYRASVESILIFNSMNQLNSLLQKENLQDVFRKVEMPSQYCLALLELNG

IGFSTAECESQKHIMQAKLDAIETQAYQLAGHSFSFTSSDDIAEVLFLEL

KLPPNREMKNQGSKKTLGSTRRGIDNGRKLRLGRQFSTSKDVLNKLKALH

PLPGLILEWRRITNAITKVVFPLQREKCLNPFLGMERIYPVSQSHTATGR

ITFTEPNIQNVPRDFEIKMPTLVGESPPSQAVGKGLLPMGRGKYKKGFSV

NPRCQAQMEERAADRGMPFSISMRHAFVPFPGGSILAADYSQLELRILAH

LSHDRRLIQVLNTGADVFRSIAAEWKMIEPESVGDDLRQQAKQICYGIIY

GMGAKSLGEQMGIKENDAACYIDSFKSRYTGINQFMTETVKNCKRDGFVQ

TILGRRRYLPGIKDNNPYRKAHAERQAINTIVQGSAADIVKIATVNIQKQ

LETFHSTFKSHGHREGMLQSDQTGLSRKRKLQGMFCPIRGGFFILQLHDE

LLYEVAEEDVVQVAQIVKNEMESAVKLSVKLKVKVKIGASWGELKDFDV.

Nucleic acid sequence:
                                          (SEQ ID NO: 2)
GGNTTYAARGAYAAYWSNCCNATHWSNGAYACNWSNTTYWSNYTNCARYT

NWSNCARGAYGGNYTNCARYTNACNCCNGCNWSNWSNWSNWSNGARWSNY

TNWSNATHATHGAYGTNGCNWSNGAYCARAAYYTNTTYCARACNTTYATH

AARGARTGGMGNTGYAARAARMGNTTYWSNATHWSNYTNGCNTGYGARAA

RATHMGNWSNYTNACNWSNWSNAARACNGCNACNATHGGNWSNMGNTTYA

ARCARGCNWSNWSNCCNCARGARATHCCNATHMGNGAYGAYGGNTTYCCN

ATHAARGGNTGYGAYGAYACNYTNGTNGTNGGNYTNGCNGTNTGYTGGGG

NGGNMGNGAYGCNTAYTAYTTYWSNYTNCARAARGARCARAARCAYWSNG

ARATHWSNGCNWSNYTNGTNCCNCCNWSNYTNGAYCCNWSNYTNACNYTN

AARGAYMGNATGTGGTAYYTNCARWSNTGYYTNMGNAARGARWSNGAYAA

RGARTGYWSNGTNGTNATHTAYGAYTTYATHCARWSNTAYAARATHYTNY

TNYTNWSNTGYGGNATHWSNYTNGARCARWSNTAYGARGAYCCNAARGTN

GCNTGYTGGYTNYTNGAYCCNGAYWSNCARGARCCNACNYTNCAYWSNAT

HGTNACNWSNTTYYTNCCNCAYGARYTNCCNYTNYTNGARGGNATGGARA

CNWSNCARGGNATHCARWSNYTNGGNYTNAAYGCNGGNWSNGARCAYWSN

GGNMGNTAYMGNGCNWSNGTNGARWSNATHYTNATHTTYAAYWSNATGAA

YCARYTNAAYWSNYTNYTNCARAARGARAAYYTNCARGAYGTNTTYMGNA

ARGTNGARATGCCNWSNCARTAYTGYYTNGCNYTNYTNGARYTNAAYGGN

ATHGGNTTYWSNACNGCNGARTGYGARWSNCARAARCAYATHATGCARGC

NAARYTNGAYGCNATHGARACNCARGCNTAYCARYTNGCNGGNCAYWSNT

TYWSNTTYACNWSNWSNGAYGAYATHGCNGARGTNYTNTTYYTNGARYTN

AARYTNCCNCCNAAYMGNGARATGAARAAYCARGGNWSNAARAARACNYT

NGGNWSNACNMGNMGNGGNATHGAYAAYGGNMGNAARYTNMGNYTNGGNM

GNCARTTYWSNACNWSNAARGAYGTNYTNAAYAARYTNAARGCNYTNCAY

CCNYTNCCNGGNYTNATHYTNGARTGGMGNMGNATHACNAAYGCNATHAC

NAARGTNGTNTTYCCNYTNCARMGNGARAARTGYYTNAAYCCNTTYYTNG

GNATGGARMGNATHTAYCCNGTNWSNCARWSNCAYACNGCNACNGGNMGN

ATHACNTTYACNGARCCNAAYATHCARAAYGTNCCNMGNGAYTTYGARAT

HAARATGCCNACNYTNGTNGGNGARWSNCCNCCNWSNCARGCNGTNGGNA

ARGGNYTNYTNCCNATGGGNMGNGGNAARTAYAARAARGGNTTYWSNGTN

AAYCCNMGNTGYCARGCNCARATGGARGARMGNGCNGCNGAYMGNGGNAT

GCCNTTYWSNATHWSNATGMGNCAYGCNTTYGTNCCNTTYCCNGGNGGNW

SNATHYTNGCNGCNGAYTAYWSNCARYTNGARYTNMGNATHYTNGCNCAY

YTNWSNCAYGAYMGNMGNYTNATHCARGTNYTNAAYACNGGNGCNGAYGT

NTTYMGNWSNATHGCNGCNGARTGGAARATGATHGARCCNGARWSNGTNG

GNGAYGAYYTNMGNCARCARGCNAARCARATHTGYTAYGGNATHATHTAY

GGNATGGGNGCNAARWSNYTNGGNGARCARATGGGNATHAARGARAAYGA

YGCNGCNTGYTAYATHGAYWSNTTYAARWSNMGNTAYACNGGNATHAAYC

ARTTYATGACNGARACNGTNAARAAYTGYAARMGNGAYGGNTTYGTNCAR

ACNATHYTNGGNMGNMGNMGNTAYYTNCCNGGNATHAARGAYAAYAAYCC

NTAYMGNAARGCNCAYGCNGARMGNCARGCNATHAAYACNATHGTNCARG

GNWSNGCNGCNGAYATHGTNAARATHGCNACNGTNAAYATHCARAARCAR

YTNGARACNTTYCAYWSNACNTTYAARWSNCAYGGNCAYMGNGARGGNAT

GYTNCARWSNGAYCARACNGGNYTNWSNMGNAARMGNAARYTNCARGGNA

TGTTYTGYCCNATHMGNGGNGGNTTYTTYATHYTNCARYTNCAYGAYGAR
```

-continued

YTNYTNTAYGARGTNGCNGARGARGAYGTNGTNCARGTNGCNCARATHGT

NAARAAYGARATGGARWSNGCNGTNAARYTNWSNGTNAARYTNAARGTNA

ARGTNAARATHGGNGCNWSNTGGGGNGARYTNAARGAYTTYGAYGTN.

TABLE 1

Nucleic acid code to generate computed sequences of Polθ$_{1792-2590}$

| Code | Meaning | Etymology | Complement | Opposite |
|---|---|---|---|---|
| A | A | Adenosine | T | B |
| T/U | T or U | Thymidine/Uridine | A | V |
| G | G | Guanine | C | H |
| C | C | Cytidine | G | D |
| K | G or T | Keto | M | M |
| M | A or C | Amino | K | K |
| R | A or G | Purine | Y | Y |
| Y | C or T | Pyrimidine | R | R |
| S | C or G | Strong | S | W |
| W | A or T | Weak | W | S |
| B | C or G or T | not A (B comes after A) | V | A |
| V | A or C or G | not T/U (V comes after U) | B | T/U |
| H | A or C or T | not G (H comes after G) | D | G |
| D | A or G or T | not C (D comes after C) | H | C |
| X/N | G or A or T or C | any | N | • |
| • | not G or A or T or C | | • | N |
| — | gap of indeterminate length | | | |

Example 3: Polymerase θ is a Robust Terminal Transferase that Oscillates Between Three Different Mechanisms During End-Joining This study, sought to elucidate how Polθ generates insertion mutations during alt-EJ which contribute to genome instability. Described herein is that manganese ($Mn^{2+}$) activates Polθ template-independent terminal transferase activity. Additionally, it is described that Polθ generates random combinations of templated and nontemplated insertion mutations during alt-EJ by oscillating between three different modes of terminal transferase activity: non-templated extension, templated extension in cis, and templated extension in trans. Finally, Polθ terminal transferase activity is characterized and it is surprisingly found that this activity is more proficient than terminal deoxynucleotidyl transferase (TdT). Together, these data identify an unprecedented switching mechanism employed by Polθ to generate genetic diversity during alt-EJ and characterize Polθ as among the most proficient terminal transferases in nature.

The materials and methods employed in these experiments are now described.

Polθ Terminal Transferase Activity 500 nM Polθ was incubated with 50 nM of the indicated 5' 32P-labeled DNA for 120 min at 42° C. (or other indicated time intervals and temp) in the presence of 0.5 mM of indicated dNTPs in a 10 μl volume of buffer A (20 mM TrisHCl pH 8.2, 10% glycerol, 0.01% NP-40, 0.1 mg/ml BSA) with indicated divalent cations; optimal Pol terminal transferase activity was performed with 5 mM MnCl2. Reactions were terminated by the addition of 20 mM EDTA and 45% formamide and DNA was resolved by electrophoresis in urea polyacrylamide gels then visualized by autoradiography. Polμ terminal transferase reactions were performed using the same conditions as Polθ. 50 nM Polθ was used in experiments employing ssDNA traps. 150-fold excess of unlabeled ssDNA trap was added to reactions at indicated time points where indicated. Polθ terminal transferase activity in solid-phase. 50 nM RP347B was immobilized to magnetic streptavidin beads (Dynabeads® M-270, Invitrogen) in buffer A supplemented with 100 mM NaCl. Excess unbound DNA was then removed by washing beads 3× with buffer A with 100 mM NaCl. Next, the bead-DNA mixture was washed and resuspended in buffer A containing 10 mM MgCl2 and 1 mM MnCl. 500 nM Polθ was then added for 10 min to allow for ssDNA binding. Excess unbound Polθ was then removed by washing the beads 4× with 200 buffer A supplemented with 10 mM MgCl2 and 1 mM MnCl$_2$. Beads were resuspended in buffer A supplemented with 10 mM MgCl2 and 1 mM MnCl$_2$, then 0.5 mM dNTPs were added at 420° C. After 15 s, either dH$_2$O or 7.5 μM RP427 was added and the reaction was terminated after 120 min by addition of EDTA. The beads were thoroughly washed to remove excess ssDNA trap. The beads were then resuspended in dH$_2$O followed by boiling for 1-2 min. The supernatant was collected, then another cycle of boiling and supernatant collection was performed. The DNA from the supernatant was purified using Zymo DNA Clean and ConcentratorTm-5 kit. Purified DNA was then ligated to RP430P overnight at room temp using T4 RNA ligase (New Englan Biolabs). RNA ligase was denatured at 65° C., then the DNA was purified using Zymo DNA Clean and ConcentratorTm-5 kit. The ligated DNA was then amplified via PCR using GoTaq® Green (Promega) and primers RP347 and RP431. PCR products were purified using QIAquick PCR purification kit (Qiagen). Pure PCR products were then cloned into E. coli plasmid vectors using TOPO® TA cloning (Invitrogen). Individual plasmids containing PCR products were amplified in E. coli, isolated, and then sequenced.

Polθ Mediated Alt-EJ In Vitro.

Equimolar concentrations (100 nM) of pssDNA substrates RP429/RP430-P and RP434-P/RP408 were mixed with 50 nM Polθ and 88.5 nM Lig3 in buffer A supplemented with 1 mM MnCl2, 10 mM MgCl2 and 1 mM ATP. Next, 10 μM dNTPs were added for 120 min at 37° C. in a total volume of 100 μl. Reactions were terminated by incubation at 80° C. for 20 min. (Negative control reactions included: omission of Lig3, and; omission of Polθ and Lig3). DNA was purified using QIAquick® Nucleotide Removal kit (QIAGEN) then amplified using PCR Master Mix (Promega) and end-joining specific primers RP431 and RP435. PCR products were purified using GeneJET PCR Purification Kit (ThermoScientific) then cloned into the pCR™2.1-TOPO™ vector (Invitrogen). DNA was transformed into E. coli DH5α cells, and individual plasmids from single colonies were purified and sequenced. Polθ mediated alt-EJ in FIG. 3—figure supplement 3 was performed as described above, however, 1 mM MgCl2, 50 μM MnCl$_2$ and 100 μM dNTPs were used. Where indicated, 150-fold excess (15 μM) of ssDNA trap (RP347) was added to the reaction at the indicated time point. Polθ mediated alt-EJ in cells. Polθ mediated alt-EJ involving chromosomal translocation was performed as previously described (Mateos-Gomez et al., 2015). Briefly, mouse Embryonic Stem (ES) cells were transfected with 3 g of Cas9-gRNA (Rosa26; H3f3b)(Mateos-Gomez et al., 2015). After transfection, 5×104 cells were seeded per well in a 96-well plate, and lysed 3 days later in 40 lysis buffer (10 mM Tris pH 8.0, 0.45% Nonidet P-40, 0.45% Tween 20). The lysate was incubated with 200 μg/ml of Proteinase K for 2 hours at 55° C. Translocation detection was performed using nested PCR. The primers used in the first PCR reaction include Tr6-11-Fwd:5'-GCGGGAGAAATGGA-TATGAA-3' (SEQ ID NO: 3); Tr6-11-Rev: 5'-TTGACGCCTTCCTTCTTCTG-3'(SEQ ID NO: 4), and Tr11-6-Fwd: 5'-AACCTTTGAAAAAGCCCACA-3'(SEQ ID NO: 5) and Tr11-6-Rev:5'-GCACGTTTCCGACTT-GAGTT-3'(SEQ ID NO: 6), for Der(6) and Der (11) respectively. For the second round of PCR amplification, the following primers were used: Tr6-11NFwd: 5'-GGCGGAT-CACAAGCAATAAT-3'(SEQ ID NO: 7); Tr6-11NRev: 5'-CTGCCATTCCAGAGATTGGT-3'(SEQ ID NO: 8) and Tr11-6NFwd:5'-AGCCACAGTGCTCACATCAC-3'(SEQ ID NO: 9) and Tr11-6NRev:5'TCCCAAAGTCGCTCT-GAGTT-3'(SEQ ID NO: 10). Amplified products corresponding to translocation events were subject to Sanger sequencing to determine the junction sequences.

TdT Terminal Transferase Activity

TdT terminal transferase reactions were performed on indicated 5' 32Plabeled DNA using conditions recommended by New England Biolabs: 50 mM potassium acetate, 20 mM Tris acetate, 10 mM magnesium acetate, pH 7.9, with 0.25 mM cobalt and incubated at 37° C. Incubation times and DNA concentrations were identical as experiments with Polθ. TdT was either used at concentrations recommended by New England Biolabs (0.2 units/l) or equimolar concentrations as Polθ as indicated in text. DNA products were resolved as indicated above.

Polθ Extension of RP347 and Preparation of DNA for Sequencing.

Polθ (500 nM) was incubated with 50 nM RP347 ssDNA along with 0.5 mM dNTPs in 100 μl of buffer A supplemented with either 5 mM $MnCl_2$ or 1 mM MnCl2 and 10 mM MgCl2 for 120 min at 42° C. Reactions were terminated by the addition of 25 μl of 5× non-denaturing stop buffer (0.5 M Tris-HCl, pH 7.5, 10 mg/ml proteinase K, 80 mM EDTA, and 1.5% SDS). This was followed by phenol-chlorphorm extraction, ethanol precipitation, then ligation to 5'-phosphorylated RP359-P ssDNA using T4 RNA ligase (NEB). DNA products were ethanol precipitated then dissolved in water. Next, PCR amplification of ligation products was performed using primers RP347 and RP359C and Taq Master Mix (Promega). PCR products were purified using GeneJET PCR Purification Kit (ThermoScientific) then cloned into the pCR™2.1-TOPO™ vector (Invitrogen). DNA was transformed into E. coli DH5α cells, and individual plasmids from single colonies were purified and sequenced.

Polθ-$Mg^{2+}$ Primer-Template Extension

Pol-$Mg^{2+}$ primer-extension was performed as described (Kent, 2015) with either 10 mM $MgCl_2$ or 5 mM $MnCl_2$ and indicated dNTPs and time intervals. Primer-extension in solidphase was performed as follows. A 2:1 ratio of template (RP409) to biotinylated primer (RP25B) was annealed then immobilized to magnetic streptavidin beads (Dynabeads® M-270, Invitrogen) pre-washed with buffer A supplemented with 100 mM NaCl. Excess unbound DNA was then removed by washing beads 3× with 200 μl of buffer A with 100 mM NaCl. Next, the bead-DNA mixture was washed and resuspended in buffer A containing 5 mM MnCl and 0.5 mM dNTPs. 500 M Polθ was then added for 120 min at 42° C. The reaction was then terminated by the addition of 20 mM EDTA followed by boiling for 1-2 min. The supernatant was collected, then another cycle of boiling and supernatant collection was performed. The DNA from the supernatant was purified using Zymo DNA Clean and ConcentratorTm-5 kit. Purified DNA was then ligated to RP430P overnight at room temp using T4 RNA ligase (New Englan Biolabs). RNA ligase was denatured at 65° C., then the DNA was purified using Zymo DNA Clean and ConcentratorTm-5 kit. The ligated DNA was then amplified via PCR using GoTaq® Green (Promega) and primers RP25 and RP431. PCR products were purified using QIAquick PCR purification kit (Qiagen). Pure PCR products were then cloned into E. coli plasmid vectors using TOPO® TA cloning (Invitrogen). Individual plasmids containing PCR products were amplified in E. coli, isolated, then sequenced. Where indicated primer-extension was performed with either a 1:1 ratio of PolθWT or PolθRR to primer-template (50 nM), or a 1:25 ratio of PolθWT or PolθRR to primer-template (50 nM). A 150-fold excess of ssDNA trap (7.5 μM RP316) was added 1 min after initiation of primer-extension where indicated.

De Novo Nucleic Acid Synthesis.

500 nM Polθ was incubated with the indicated nucleotides at the following concentrations (500 nM ATP,UTP,GTP, dATP,dTTP,dGTP; 97 nM dCTP, [α-32P]-6000Ci/mmol 20mCi/ml (Perkin Elmer)) for the indicated time intervals at 42° C. in buffer A supplemented with 5 mM MnCl. Nucleic acid products were resolved in denaturing polyacrylamide gels and visualized by autoradiography. PolθWT and mutant proteins PolθL2 and PolθRR were purified as described (Kent, 2015). Site-directed mutagenesis was performed using QuickChange II Site-Directed Mutagenesis Kit (Agilent Technologies). TdT was purchased from New England Biolabs (NEB). Polμ and Lig3 were purchased from Enzymax. DNA. pssDNA, dsDNA and primer-templates were assembled by mixing equimolar concentrations of ssDNA substrates together in deionized water, then heating to 95-100° C. followed by slow cooling to room temp. ssDNA was 5' 32P-labeled using 32P-7-ATP (Perkin Elmer) and T4 polynucleotide kinase (NEB). DNA (Integrated DNA technologies (IDT)) and RNA (Dharmacon) oligonucleotides (5'-3').

```
RP25:
                                      (SEQ ID NO: 11)
CACAGATTCTGGCAGGCTGCAGATCGC

RP25B:
                                      (SEQ ID NO: 12)
Biotin-CACAGATTCTGGCAGGCTGCAGATCGC RP347:
                                      (SEQ ID NO: 13)
CACTGTGAGCTTAGGGTTAGAGATAC RP348:
                                      (SEQ ID NO: 14)
CACTGTGAGCTTAGGGTTAGAGCCGG RP63:
                                      (SEQ ID NO: 15)
CGAAATAGACAGATCGCTGAGGATAGGTGCCTCACTG RP63C:
                                      (SEQ ID NO: 16)
CAGTGAGGCACCTATCCTCAGCGATCTGTCTATTTCG RP271:
                                      (SEQ ID NO: 17)
CATCTTTTACTTCCACCAGCGTTTCTGGG RP271C:
                                      (SEQ ID NO: 18)
CCCAGAAACGCTGGTGGAAGTAAAAGATG RP359:
                                      (SEQ ID NO: 19)
GTGGATGAATTACACATGCTGGGAGACTC
```

-continued

RP359C:
(SEQ ID NO: 20)
GAGTCTCCCAGCATGTGTAATTCATCCAC

RP266:
(SEQ ID NO: 27)
TTTTTTTTTTTTTTTTTGCGATCTGCAGCCTGCCAGAATCTGTG

RP331:
(SEQ ID NO: 21)
ACTGTGAGCTTAGGGTTAGGGTTAGGGTTAGGGTTAG

RP340:
(SEQ ID NO: 28)
CACTGTGAGCTTAGGGTTAGAGATCG

RNA-2:
(SEQ ID NO: 29)
AUCGAGAGG

RP343-P:
(SEQ ID NO: 30)
/5Phos/CTAAGCTCACAGTG

RP429:
(SEQ ID NO: 22)
GGAGGTTAGGCACTGTGAGCTTAGGGTTAGAGATAC

RP430-P:
(SEQ ID NO: 23)
/5Phos/CTAAGCTCACAGTGCCTAACCTCC

RP434-P:
(SEQ ID NO: 24)
/5Phos/GAGCACGTCCAGGCGATCTGCAGCCTG

RP408:
(SEQ ID NO: 25)
GAGCACGTCCAGGCGATCTGCAGCCTGCCAGAATCTGTG

RP427:
(SEQ ID NO: 31)
CGCCACCTCTGACTTGAGCG

RP409:
(SEQ ID NO: 32)
GAGCACGTCCACGCGATCTGCAGCCTGCCAGAATCTGTG

RP347B:
(SEQ ID NO: 26)
Biotin-CACTGTGAGCTTAGGGTTAGAGATAC pssDNA substrates:
RP347/RP343-P, RP348/RP343-P, RP340/RP343-P,
RP429/RP430-P, RP434-P/RP408.

Telomeric ssDNA, RP331. Primer-templates,
RP25/RP266, RP25/409, RP25B/409.

Nucleotide Analogs 1, cy3-dUTP (Santa Cruz Biotech.); 2, Digoxigenin-11-dUTP (Sigma); 3, Biotin-16AAdUTP (TriLink Biotech.); 4, Texas Red-5-dCTP (PerkinElmer); 5, N6-(6-Azido)hexyl-ATP (Jena Bioscience); 6, Cyanine 3-AA-UTP (TriLink Biotech.); 7, 4-Thio-UTP (TriLink Biotech.); 8, Biotin-16-AACTP (TriLink Biotech.); 9, Ganciclovir Triphosphate (TriLink Biotech.); 10, 5-Hydroxymethyl-2'-deoxyuridine-5'-Triphosphate (TriLink Biotech.).

The results of the experiments are now described.

Polθ Template-Independent Activity Requires Manganese

Figures 7A, 7B, 7C:
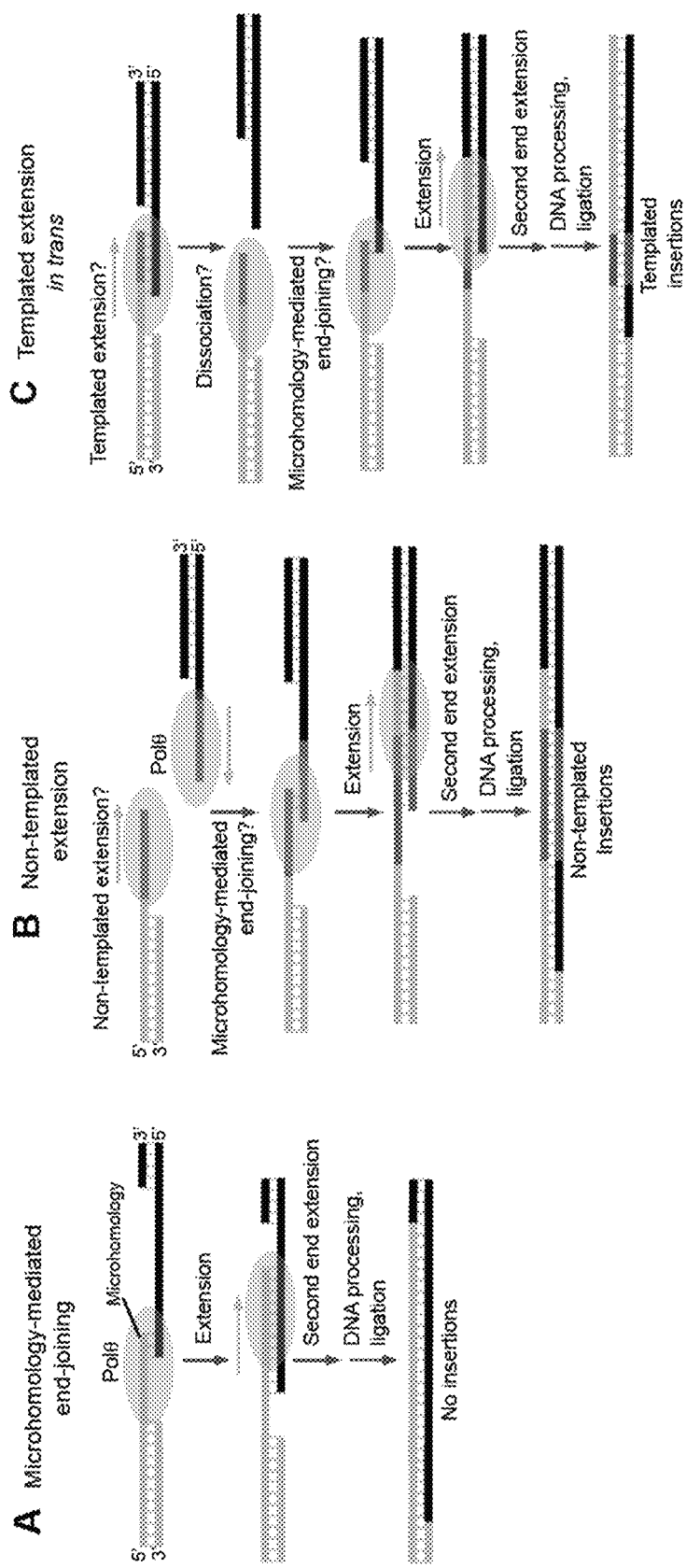
FIG. 7A through FIG. 7G, depicts results of experiments demonstrating that Polθ exhibits robust template-independent terminal transferase activity in the presence of manganese.
Figures 7D, 7E, 7F, 7G:
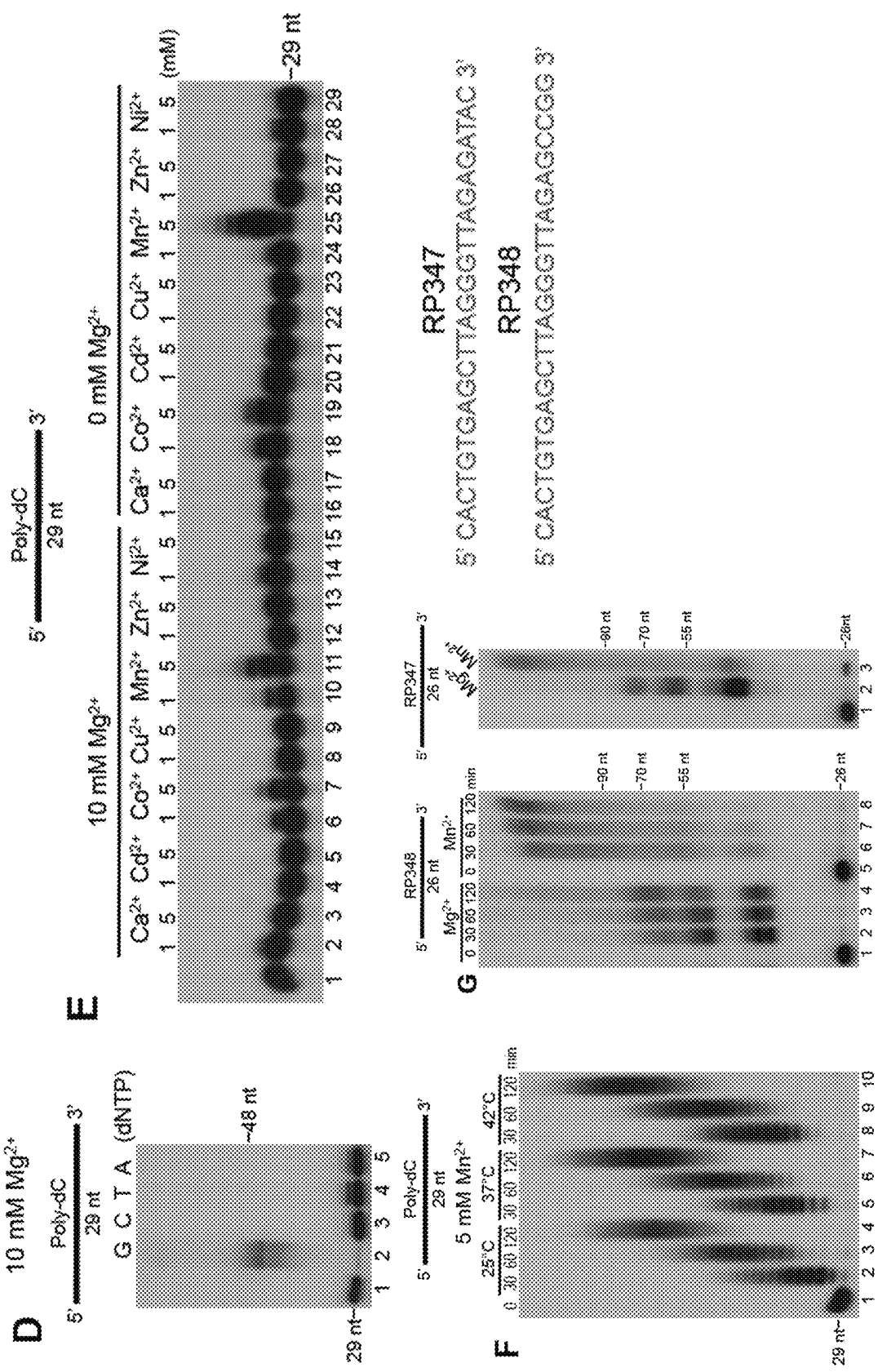

A current paradox in the understanding of alt-EJ is that Polθ promotes non-templated (random) nucleotide insertions at DNA repair junctions in vivo, but lacks template-independent terminal transferase activity in vitro. For example, similar to previous studies (Hogg et al., 2012; Kent, 2015), Polθ fails to extend a homopolymeric ssDNA containing deoxycytidine-monophosphates (poly-dC) in the absence of the complementary deoxyguanosine-triphosphate (dGTP) under standard buffer conditions with magnesium ($Mg^{2+}$) (FIG. 7D). This shows that efficient ssDNA extension by Polθ requires the complementary nucleotide, which demonstrates that the template bases facilitate the nucleotidyl transferase reactions by pairing with the incoming nucleotide. Recent studies suggest that this template-dependent activity is due to 'snap-back' replication whereby the polymerase uses the template in cis (Kent, 2015). A separate biochemical study also indicated that Polθ lacks template-independent activity (Yousefzadeh et al., 2014). Thus, it remains unclear how Polθ facilitates random nucleotide insertions during alt-EJ which contribute to genome instability (FIG. 7B).

Figures 8A, 8B:
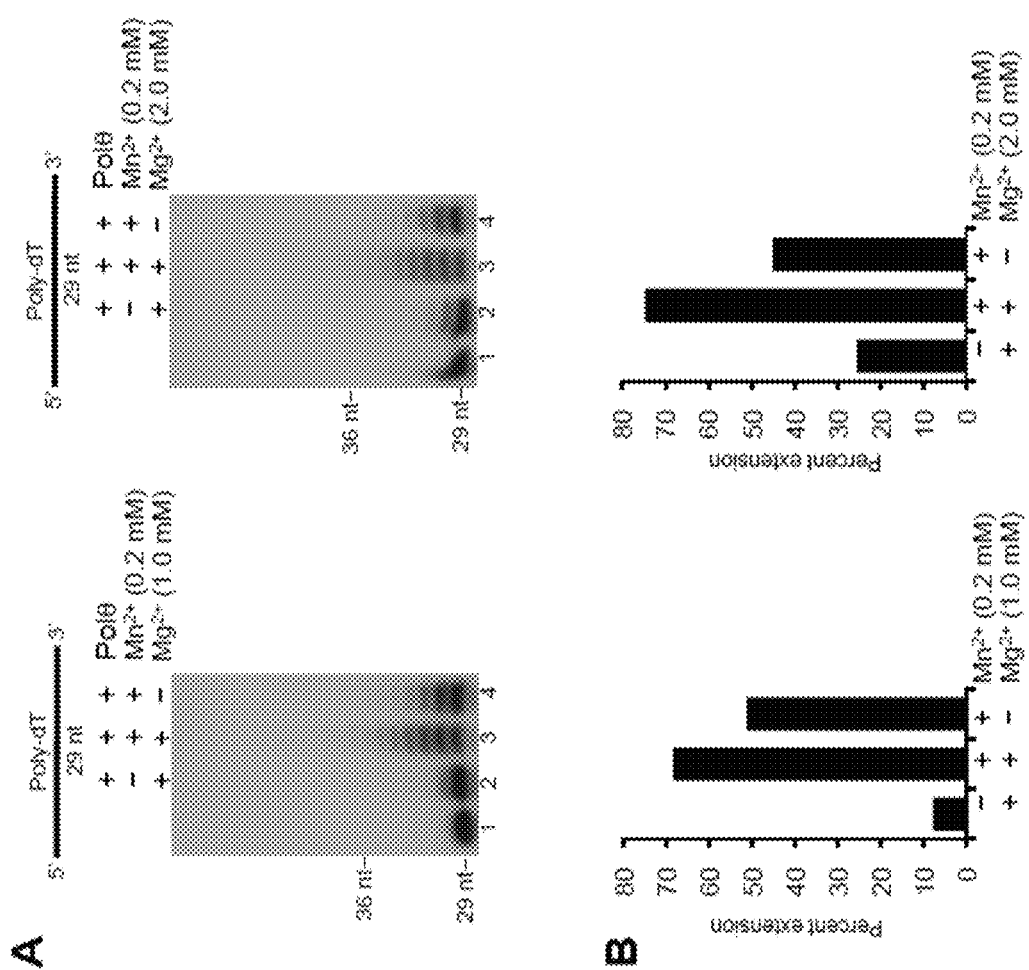
FIG. 8A and FIG. 8B, depicts results of experiments demonstrating that Polθ template-independent activity is stimulated by physiological concentrations of $Mn^{2+}$ and $Mg^{2+}$.

Considering that divalent cations other than $Mg^{2+}$ are present in cells, they may account for the discrepancy between the ability of Polθ to perform template-independent DNA synthesis in vivo but not in vitro. Therefore various divalent cations were tested in a reaction including Polθ, poly-dC ssDNA and deoxythymidinetriphosphate (dTTP), in the presence and absence of $Mg^{2+}$ (FIG. 7E). The results showed that $Mn^{2+}$, and to a lesser extent C2+, activates Polθ extension of poly-dC with dTTP (FIG. 7E). For example, in the absence of $Mn^{2+}$ in FIG. 7D, Pol extended only a small fraction of substrates with dTTP (lane 4). In contrast, the addition of $Mn^{2+}$ under the same reaction conditions promoted extension of the same substrate by Polθ even when $Mg^{2+}$ was abundant (FIG. 7E). Since thymidine cannot base pair with cytidine, these data demonstrate that $Mn^{2+}$ activates Polµ template-independent terminal transferase activity (i.e. non-templated DNA synthesis). Since Polθ DNA synthesis activity is fully supported by $Mn^{2+}$ (FIG. 7E, lane 25), this indicates that $Mn^{2+}$ binds to the same positions as $Mg^{2+}$ within the polymerase active site which is necessary for the nucleotidyl transferase reaction. Consistent with this, recent structural studies show that other metals such as calcium can substitute for $Mg^{2+}$ in the polymerase active site (Zahn et al., 2015). Furthermore, several lines of evidence show that $Mn^{2+}$ can act as a co-factor for DNA polymerases and RNA polymerases and reduces the fidelity of these enzymes (Andrade et al., 2009; Dominguez et al., 2000; Walmacq et al., 2009). Hence, the data show that $Mn^{2+}$ acts as a co-factor for Polθ which promotes template-independent activity and likely reduces the fidelity of the polymerase. Importantly, this template-independent activity was also stimulated 3-8 fold by relatively low concentrations of $Mn^{2+}$ (0.2 mM) and $Mg^{2+}$ (1-2 mM) which are found in cells (FIG. 8) (MacDermott, 1990; Schmitz et al., 2003; Visser et al., 2014). Biochemical studies have also shown that $Mn^{2+}$ is a necessary co-factor for the yeast Mre11-Rad50-Xrs2 (MRX) nuclease complex and its mammalian counterpart, MRN, which is essential for generating 3' overhangs during alt-EJ, presumably by acting with CtIP (Lee-Theilen et al., 2011; Trujillo et al., 1998; Zhang and Jasin, 2011). Thus, these and other lines of evidence strongly indicate a physiological role for $Mn^{2+}$ as a co-factor for DNA repair enzymes (Andrade et al., 2009; Cannavo and Cejka, 2014; Dominguez et al., 2000; Trujillo et al., 1998).

Figures 9A, 9B, 9C, 9D, 9E:
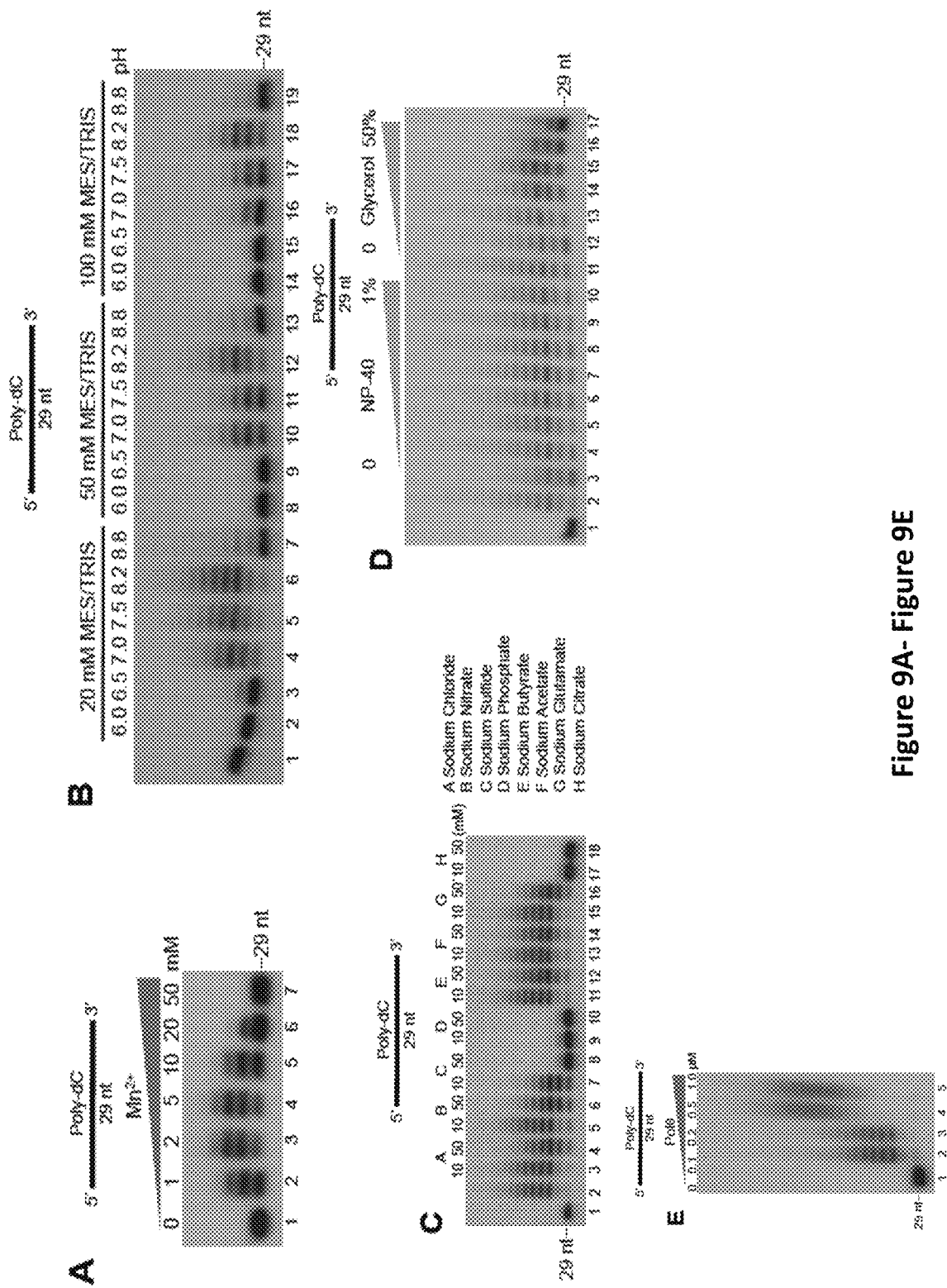
FIG. 9A through FIG. 9E, depicts results of experiments demonstrating optimization of Pol-$Mn^{2+}$ template-independent terminal transferase activity.
Figures 10A, 10B:
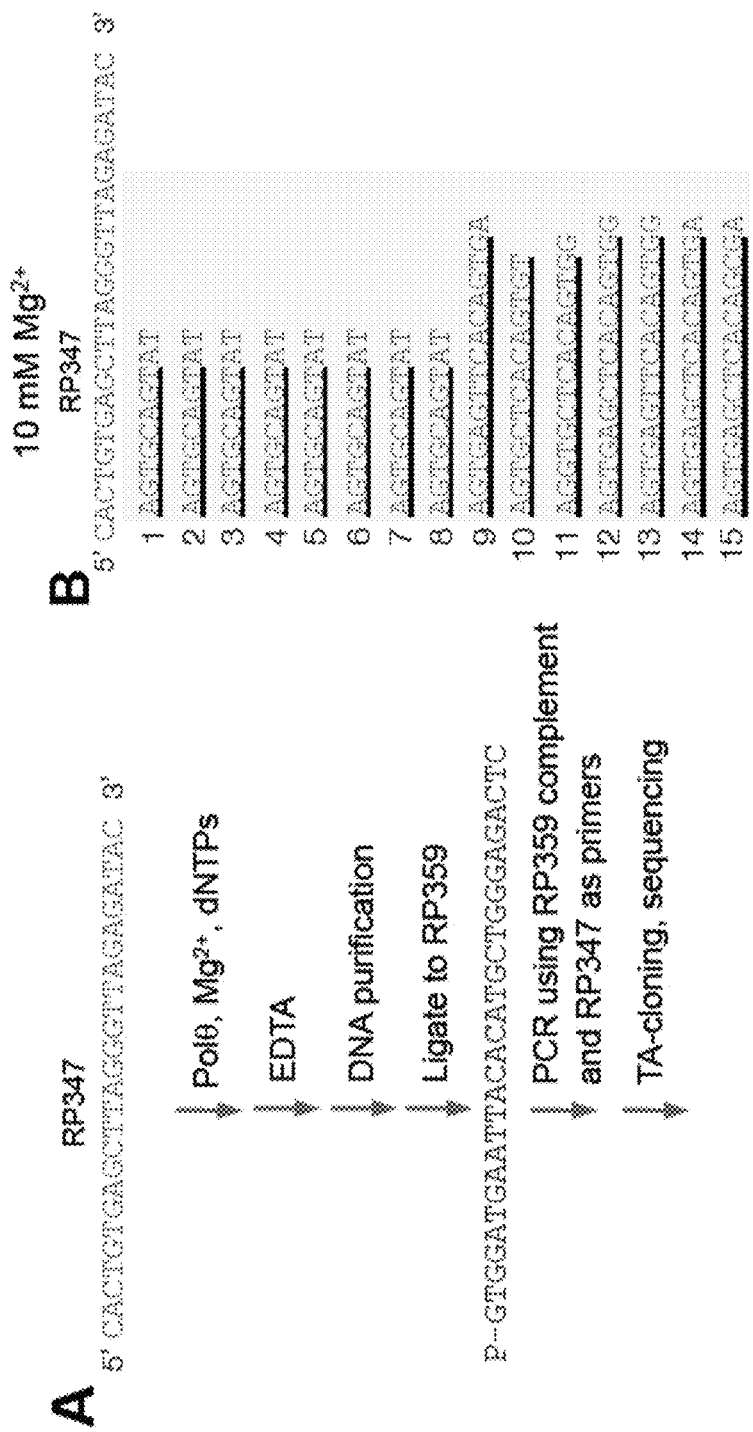
FIG. 10A through FIG. 10D, depicts results of experiments demonstrating the sequence analysis of Polθ-$Mg^{2+}$ template-dependent terminal transferase activity.
Figure 10C:
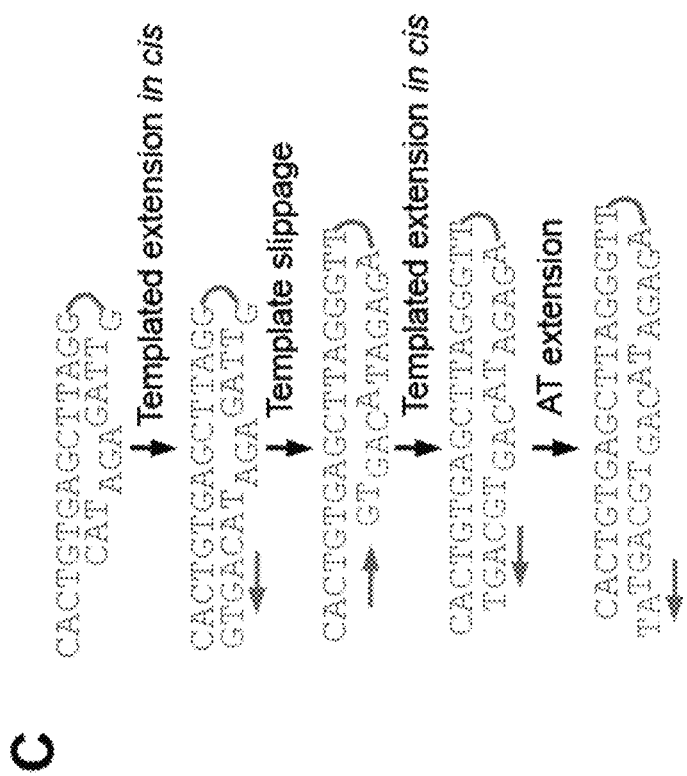
Figure 10D:
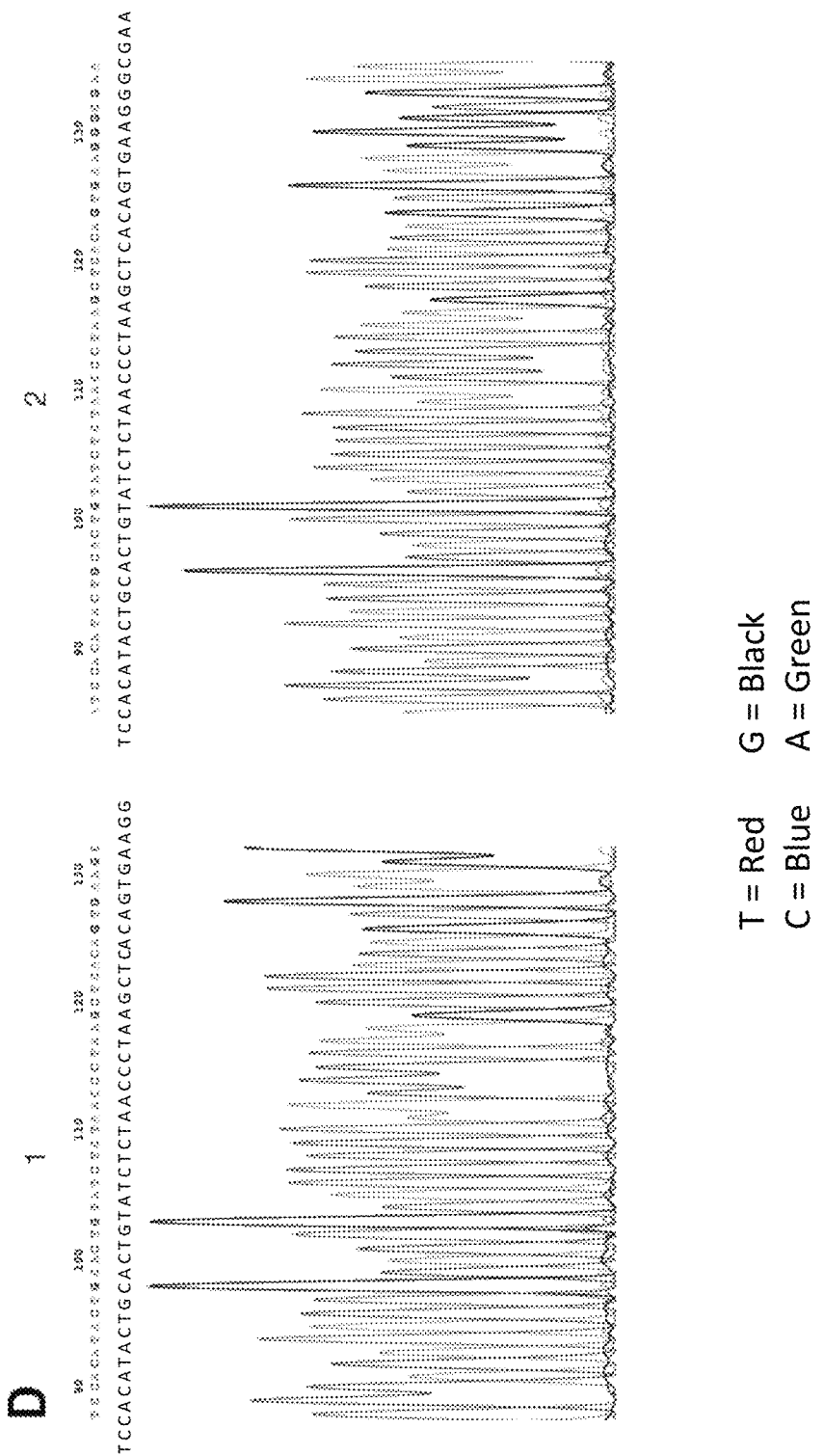
Figure 10D:
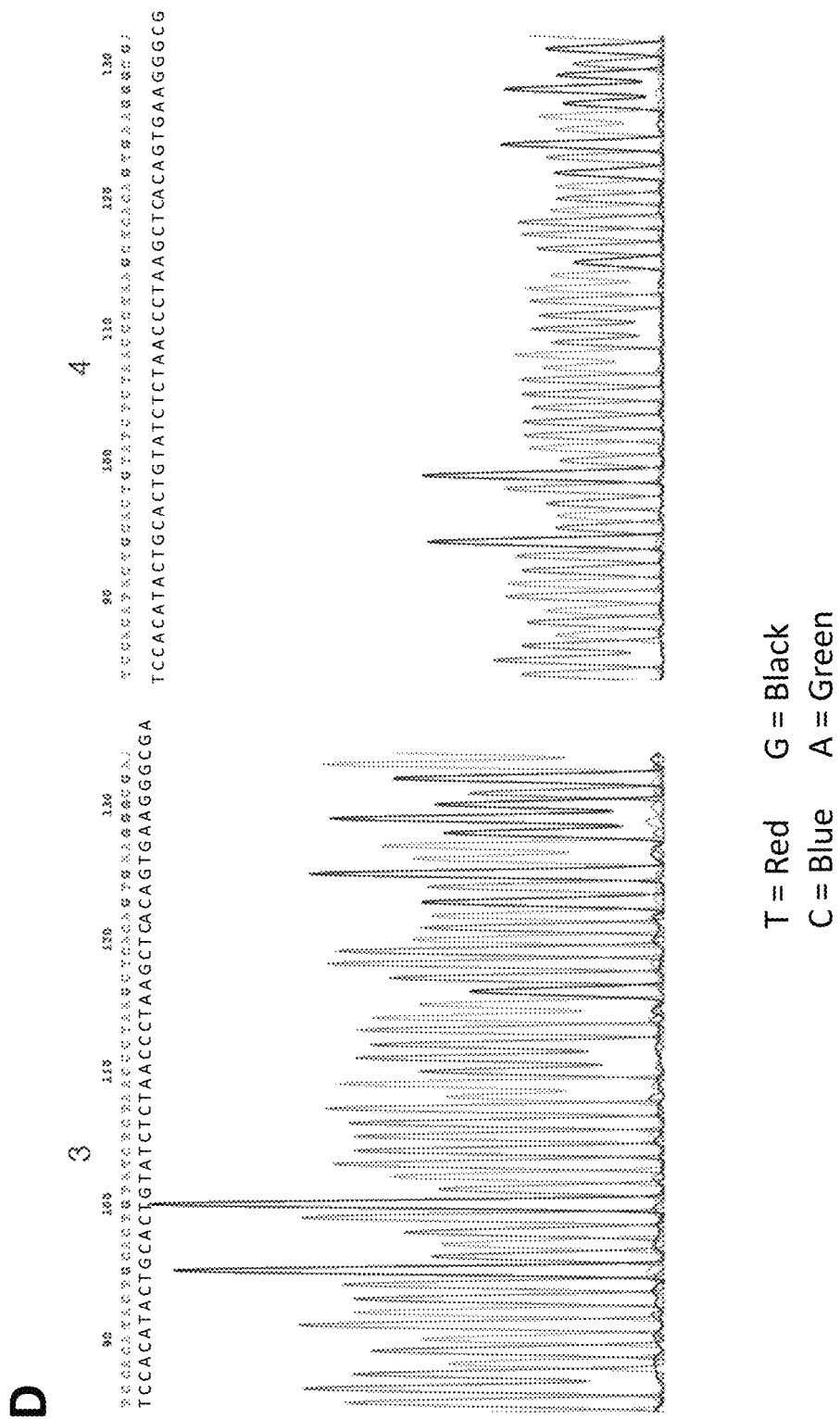
Figure 10D:
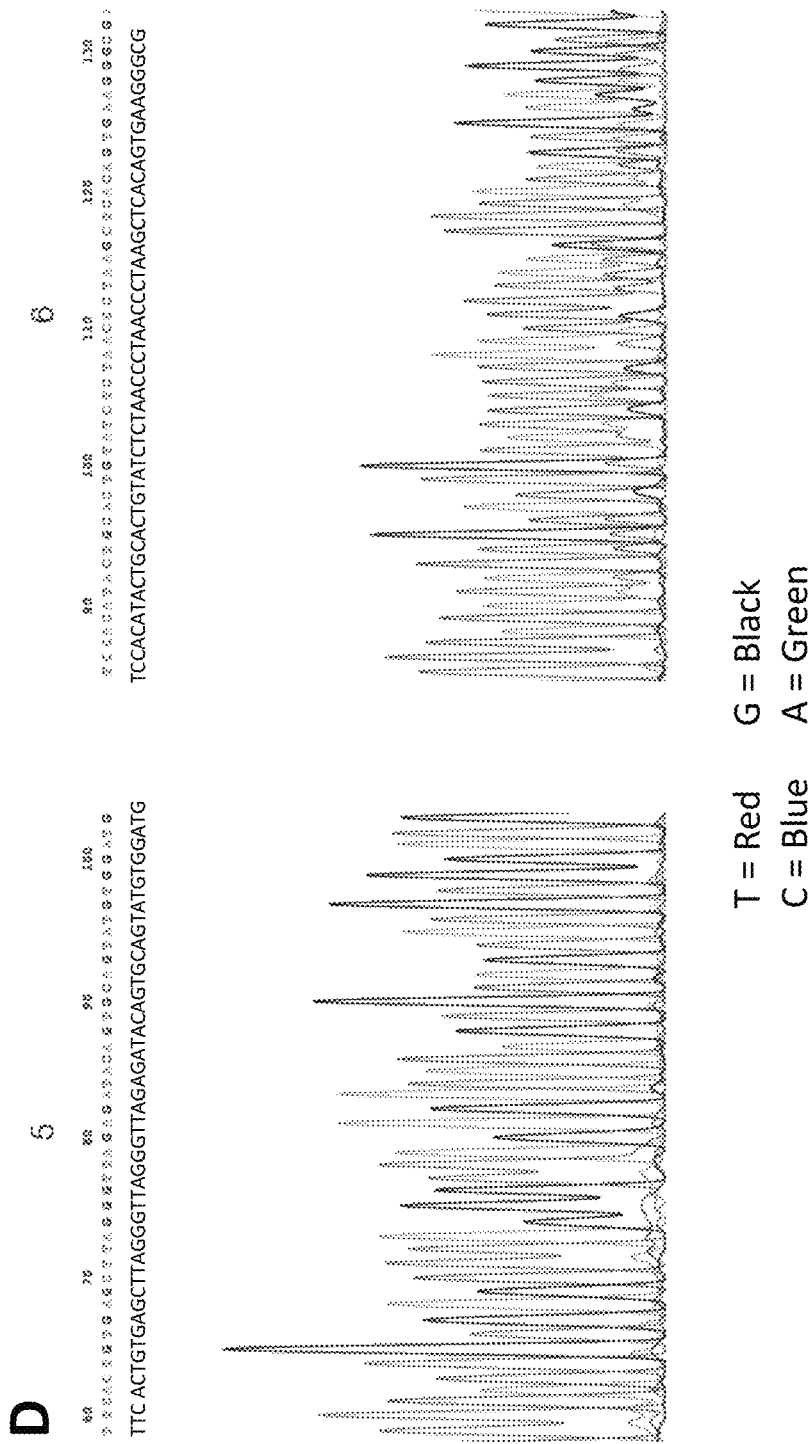

Optimal conditions were identified for Polθ-$Mn^{2+}$ template-independent terminal transferase activity in FIG. 9. Using these optimal conditions at different temperatures, it was found that Polθ-$Mn^{2+}$ exhibits robust template-independent terminal transferase activity (FIG. 7F). This suggests $Mn^{2+}$ promotes the ability of Polθ to generate random nucleotide insertions during alt-EJ in cells. It was further found that $Mn^{2+}$ greatly stimulates Polθ terminal transferase activity on non-homopolymeric ssDNA substrates (FIG. 7G, left and right). In contrast, in the presence of $Mg^{2+}$ Polθ became mostly arrested after transferring ~10-20 nucleotides (nt), but also generated some larger discrete products (FIG. 7G, left and right). These data along with those presented in FIG. 7D indicate that $Mg^{2+}$ promotes template-dependent activity which directs the polymerase to repeatedly synthesize a few discrete products as observed for both substrates (FIG. 7G, left and right). Consistent with this, Polθ-$Mg^{2+}$ consistently generated similar DNA sequences from the RP347 ssDNA template, which is likely due to snap-back replication (FIG. 10). $Mn^{2+}$ on the other hand facilitates template-independent activity which enables Polθ to generate random products of different lengths as indicated by a smear (FIG. 7G, left and right).

Polθ Oscillates Between Three Different Modes of Terminal Transferase Activity

Figures 11C, 11D, 11E:
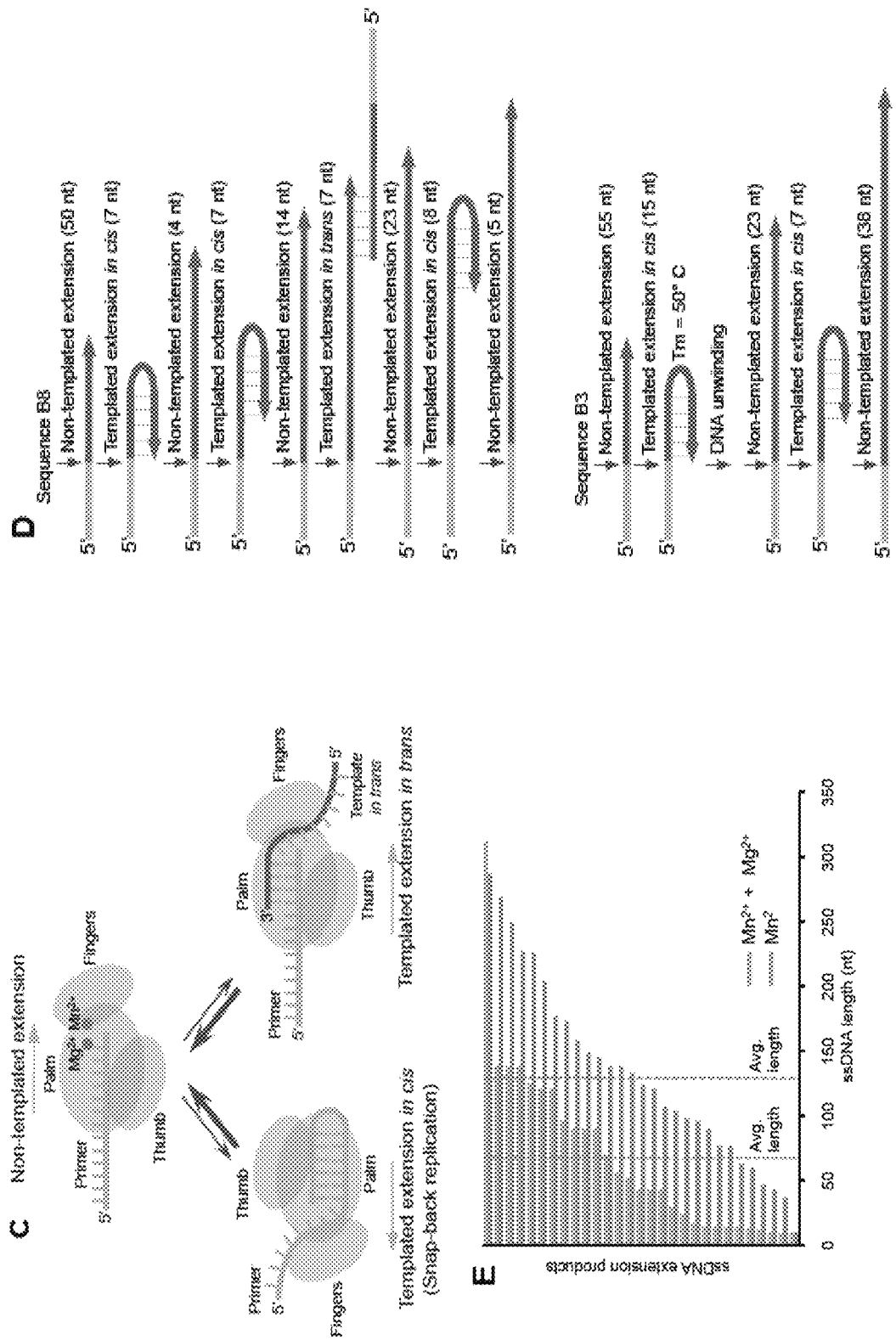

To gain more insight into these mechanisms of Polθ terminal transferase activity, the sequences of ssDNA extension products generated by Polθ-$Mn^{2+}$ in the absence of $Mg^{2+}$ and with a 10-fold excess of $Mg^{2+}$ which models cellular conditions were analyzed. As expected, most of the DNA sequence generated by Polθ-$Mn^{2+}$ in the absence of $Mg^{2+}$ was random and therefore due to template-independent activity (FIG. 11A). This is consistent with the appearance of a smear rather than a few discrete bands as observed with Polθ-$Mg^{2+}$ (FIG. 7G). Intriguingly, some of the sequences contained short regions that were either identical or complementary to the initial ssDNA (FIG. 11A, black underlines). Other sequence regions within individual molecules were complementary to one another but not to the original ssDNA template (FIG. 11A, grey and colored lines). Next, DNA sequences generated by Polθ in the presence of a 10-fold excess of $Mg^{2+}$ relative to $Mn^{2+}$ were analyzed, which more closely resembles physiological conditions (FIG. 11). Again, random sequence, complementary sequences within individual products (grey and colored lines), and short sequence tracts identical or complementary to the initial template (black underlines) were observed. Interestingly, Polθ generated more complementary sequences with an excess of $Mg^{2+}$ (compare FIG. 11A and FIG. 11). Furthermore, the average length of ssDNA extension products was shorter with an excess of $Mg^{2+}$ (FIG. 11E), which is consistent with the results in FIG. 7G.

Figure 12:
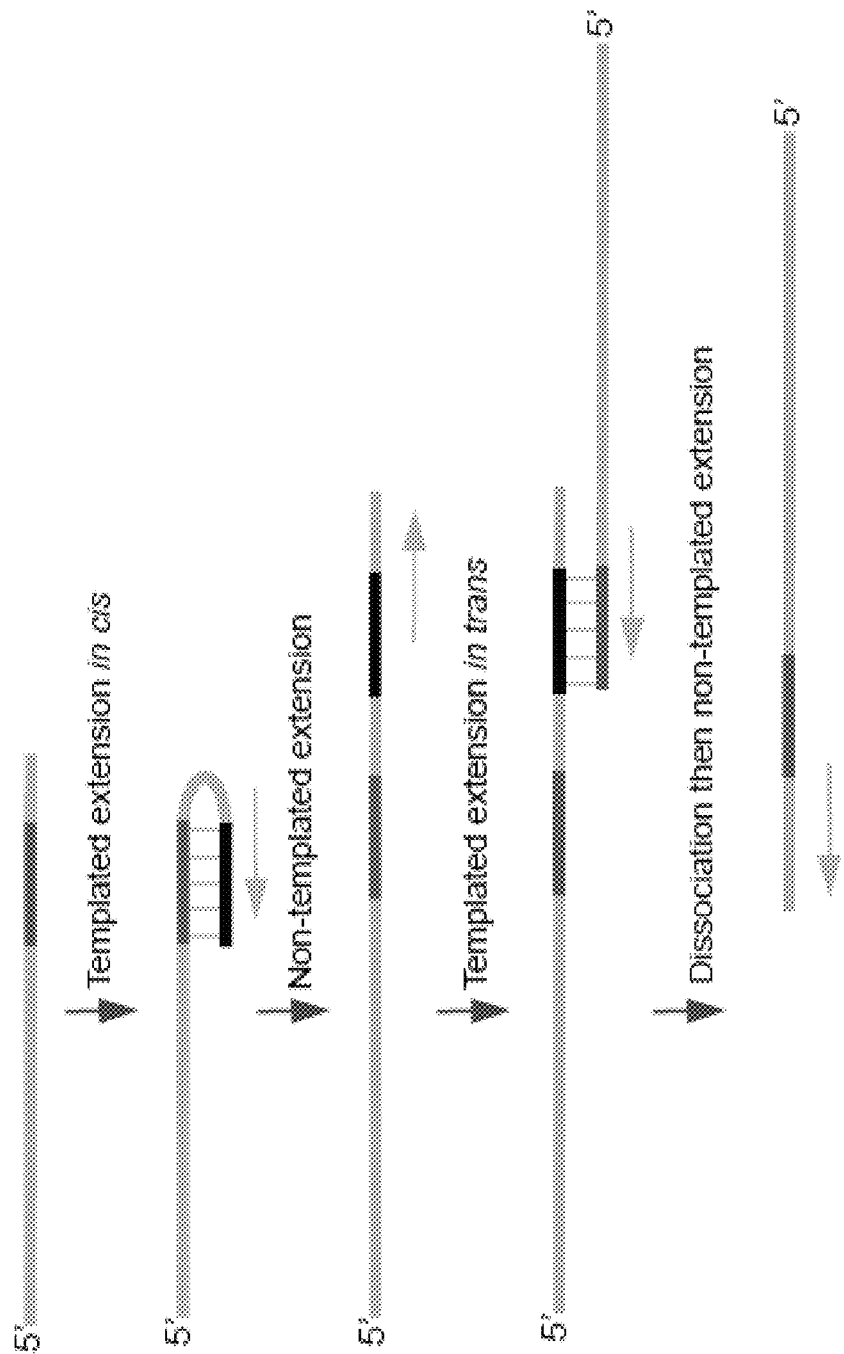
FIG. 12 depicts a model of how Polθ generates sequence tracts identical to the initial template in the presence of $Mn^{2+}$. Red, original sequence copied; black, complement of red sequence. The black complementary sequence may also be generated via templated extension in trans.

Together, these data demonstrate that Polθ exhibits three distinct modes of terminal transferase activity when $Mn^{2+}$ is present even at 10-fold lower concentrations than $Mg^{2+}$ (FIG. 11C). In the first and predominant mode, Polθ performs template-independent terminal transferase activity (FIG. 11C, top). In the second mode, Polθ performs transient template-dependent extension in cis, also called snap-back replication (FIG. 11C, bottom left). This mechanism accounts for the appearance of complementary sequences within individual extension products (FIGS. 11A and 11B; grey and colored lines). In the third mode, Polθ performs transient template dependent extension in trans (FIG. 11C, bottom right). This accounts for sequence tracts that are identical or complementary to the initial ssDNA substrate (FIGS. 11A and 11B; black underlines); templated extension in cis can also promote sequence complementary to the initial template (FIG. 11C). Identical sequence tracts are most likely due to copying in trans of complementary sequence tracts initially formed by templated extension in cis or in trans (FIG. 12). Further in vitro and in vivo evidence for these three mechanisms of terminal transferase activity is presented in FIGS. 13 and 14, respectively.

Intriguingly, many of the extension products were generated by more than one mode of terminal transferase activity (FIG. 11), which demonstrates that the polymerase oscillates between these mechanisms (FIG. 11C). Product sequences were utilized to specifically trace this enzymatic switching phenomenon at near base resolution (FIG. 11D). For example, sequence 8 from FIG. 11B demonstrates that Polθ first performs 50 consecutive random nucleotide transfer events, then switches to a transient snap-back replication mode (templated extension in cis). Next, Polθ switches to random mode then after transferring 4 nt switches back to snap-back mode followed by another switch back to random synthesis. Next, Polθ switches to the templated extension in trans mode where it copies 7 nt, then switches back to random mode for an additional 23 nt. Finally, Polθ switches back to snap-back mode, then after transferring 8 nt it ends the reaction by randomly incorporating an additional 5 nt. Sequence 3 from FIG. 11B shows similar oscillation between these different mechanisms (FIG. 11D, bottom). Here, Polθ performs 55 consecutive random nucleotide transfer events then switches to snap-back mode where it incorporates another 15 nt. Since the melting temperature of this 15 bp duplex is predicted to be 50° C. and the reaction was performed at 42° C., Polθ appears to be capable of unwinding duplexes formed during snap-back replication. Polθ then performs three additional switching events, ultimately generating in a 138 nt product composed of a combination of random and templated sequence.

Under these conditions, Polθ shows a preference for template-independent terminal transferase activity (FIG. 11C), which is more prevalent when $Mg^{2+}$ is omitted (compare FIGS. 11A and 11B). Thus, the ratio of $Mn^{2+}$ to $Mg^{2+}$ modulates the balance between these different mechanisms. For example, higher concentrations of $Mn^{2+}$ promote template-independent transfer events, whereas lower concentrations of $Mn^{2+}$ reduce random transferase activity while increasing template-dependent activity due to snap-back replication (compare FIGS. 11A and 11B). Higher concentrations of $Mn^{2+}$ also promote longer extension products, which correlates with the polymerase's preference for template-independent activity under these identical conditions (FIG. 11E; FIG. 7G).

Figure 15A:
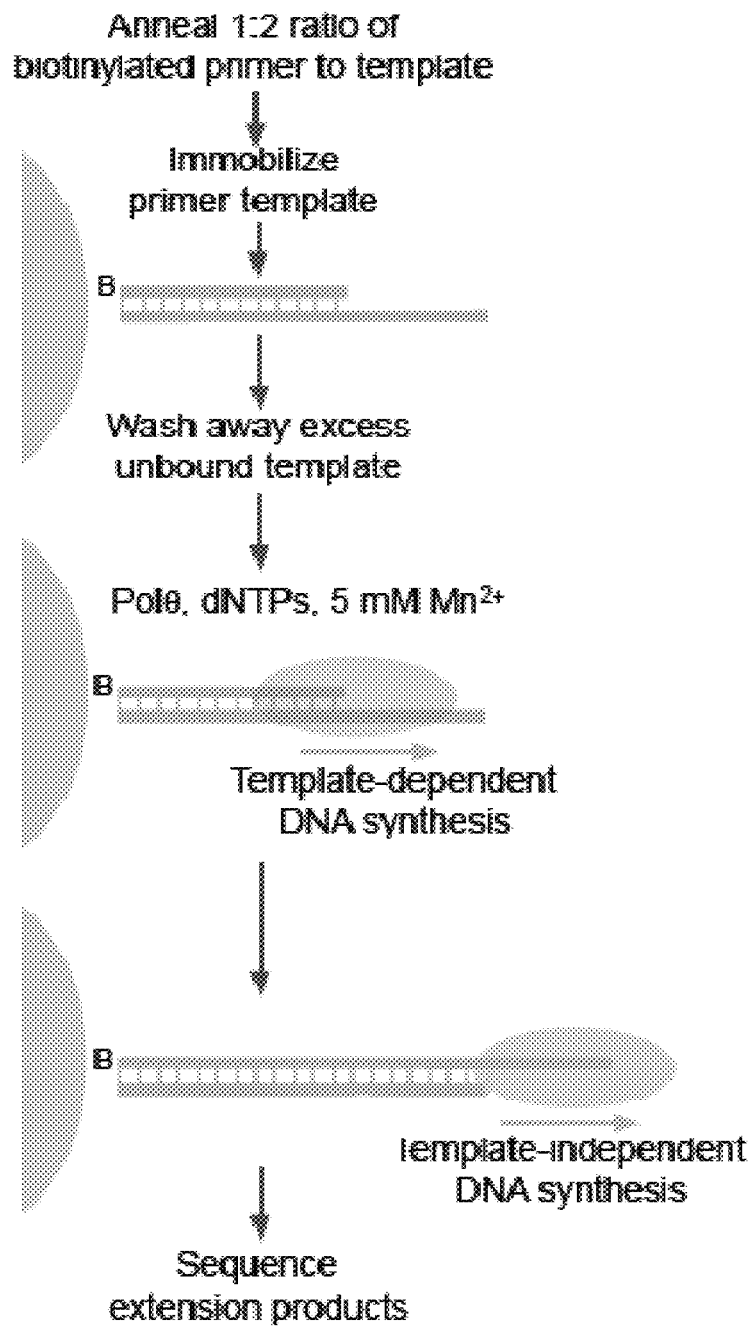
FIG. 15A through FIG. 15D, depicts results of control experiments for Polθ-Mn$^{2+}$ template-independent activity.
Figure 15B:
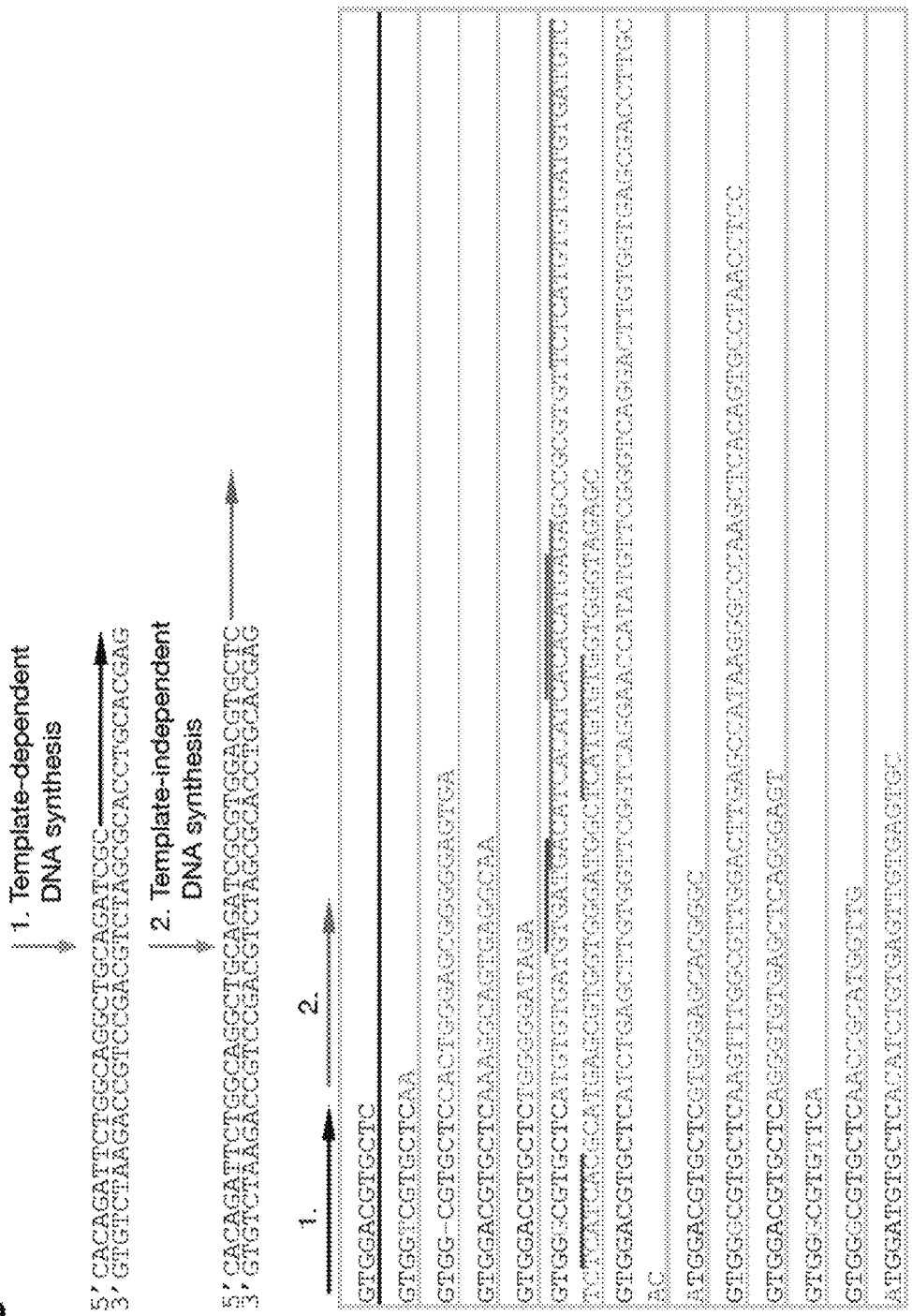
Figures 15C, 15D:
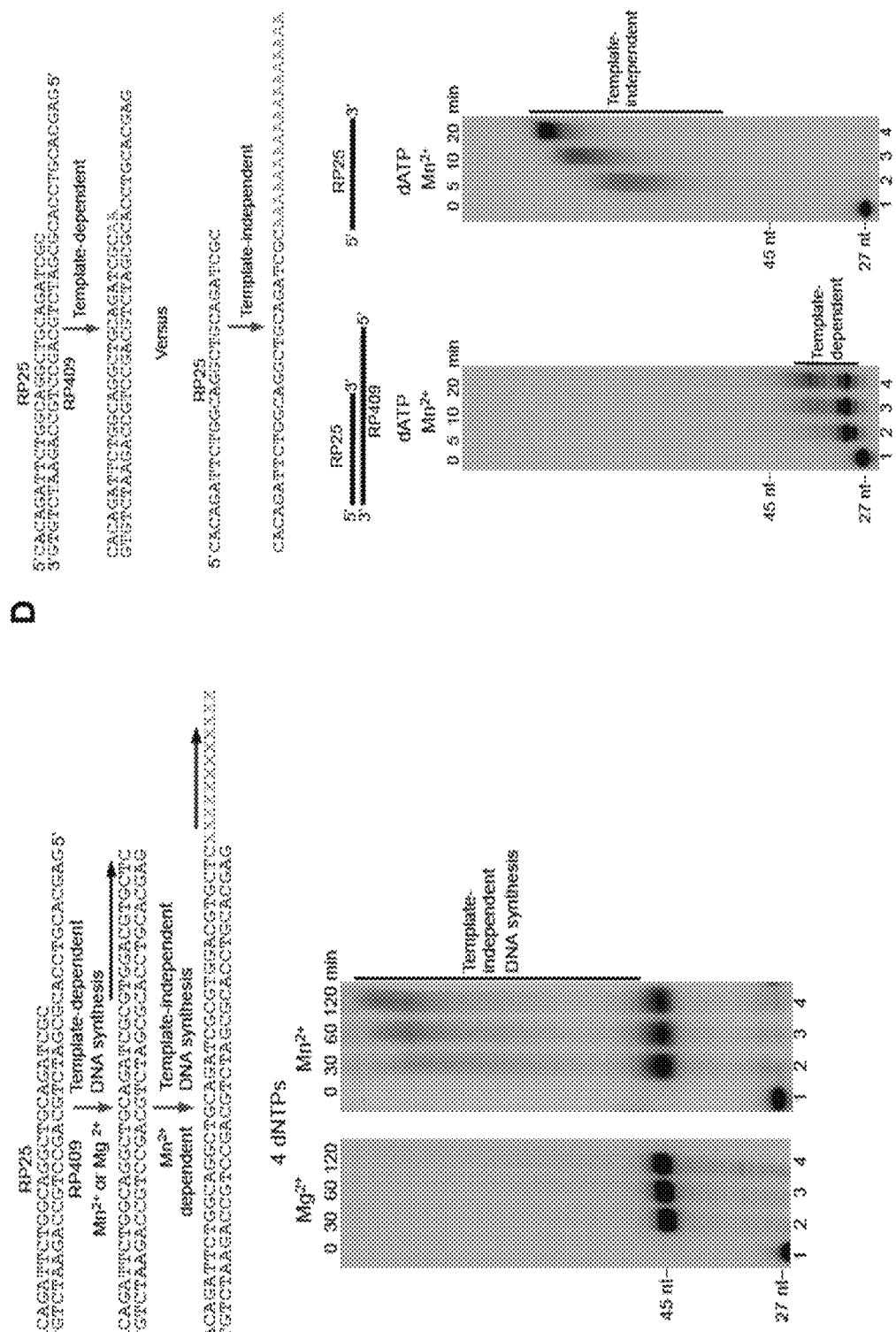
Figure 16:
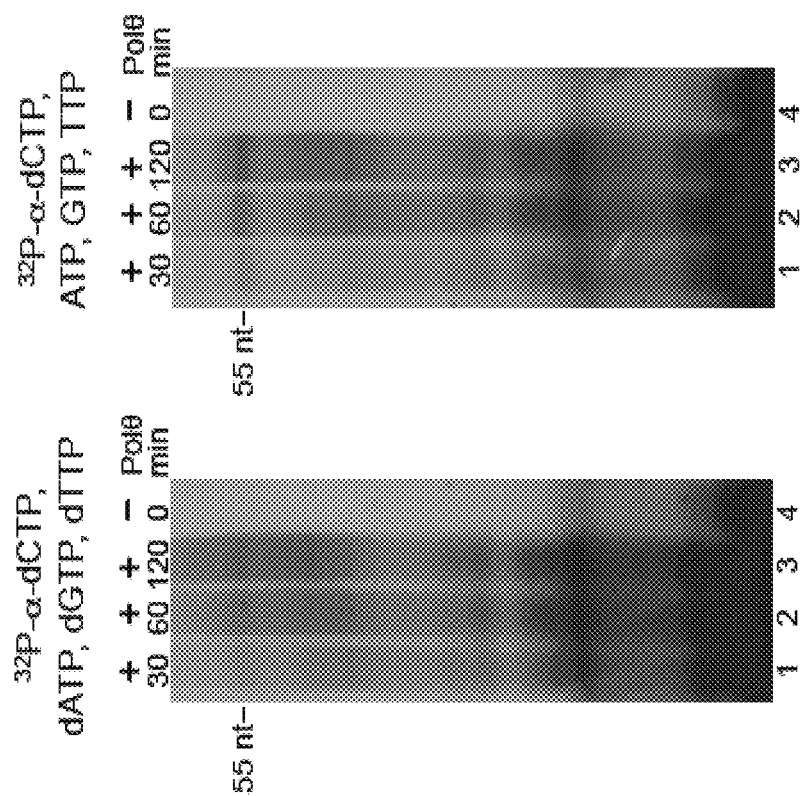
FIG. 16 depicts results of experiments demonstrating that Pol-Mn$^{2+}$ exhibits de novo DNA and RNA synthesis activities. Depicted are denaturing gels showing de novo nucleic-acid synthesis by Polθ in the presence of 5 mM Mn$^{2+}$ and indicated nucleotides.

To be certain Polθ-$Mn^{2+}$ performs template-independent activity rather than highly error-prone template dependent activity which may be perceived as template-independent, multiple additional controls were performed. First, template-dependent and independent activities were analyzed in the same reaction performed in solid-phase (FIG. 15). Here, a biotinylated primer-template was immobilized to streptavidin beads, then excess template strand was removed by thorough washing. Primer extension in the presence of $Mn^{2+}$ was then performed and extension products were sequenced. The results show that the initial template-dependent activity is performed with relatively high fidelity (FIG. 15B). For example, misincorporation and frameshift error rates of $5.6 \times 10^{-2}$ and $6.9 \times 10^{-3}$, respectively, were observed on this short template. On the other hand, once Polθ reaches the end of the template mostly random sequence was generated, demonstrating template-independent activity (FIG. 15B). Consistent with this Polθ is able to continue DNA synthesis far beyond the end of the template exclusively in the presence of $Mn^{2+}$ (FIG. 15C). The rate of misincorporation and mismatch extension by Polθ-$Mn^{2+}$ on a primer-template in the presence of a single nucleotide (dATP) is dramatically slower than its activity under identical conditions without the template strand present (FIG. 15D). Thus, these data demonstrate that Pol-$Mn^{2+}$ terminal transferase activity is not the result of misincorporation or mismatch extension. As an additional control for template independent activity, it was tested whether Polθ-Mn$^{2+}$ performs de novo synthesis in the absence of DNA. Remarkably, Polθ-Mn$^{2+}$ exhibits de novo DNA and RNA synthesis which unequivocally demonstrates its ability to synthesize nucleic-acids in a template-independent manner (FIG. 16).

Figures 17A, 17B:
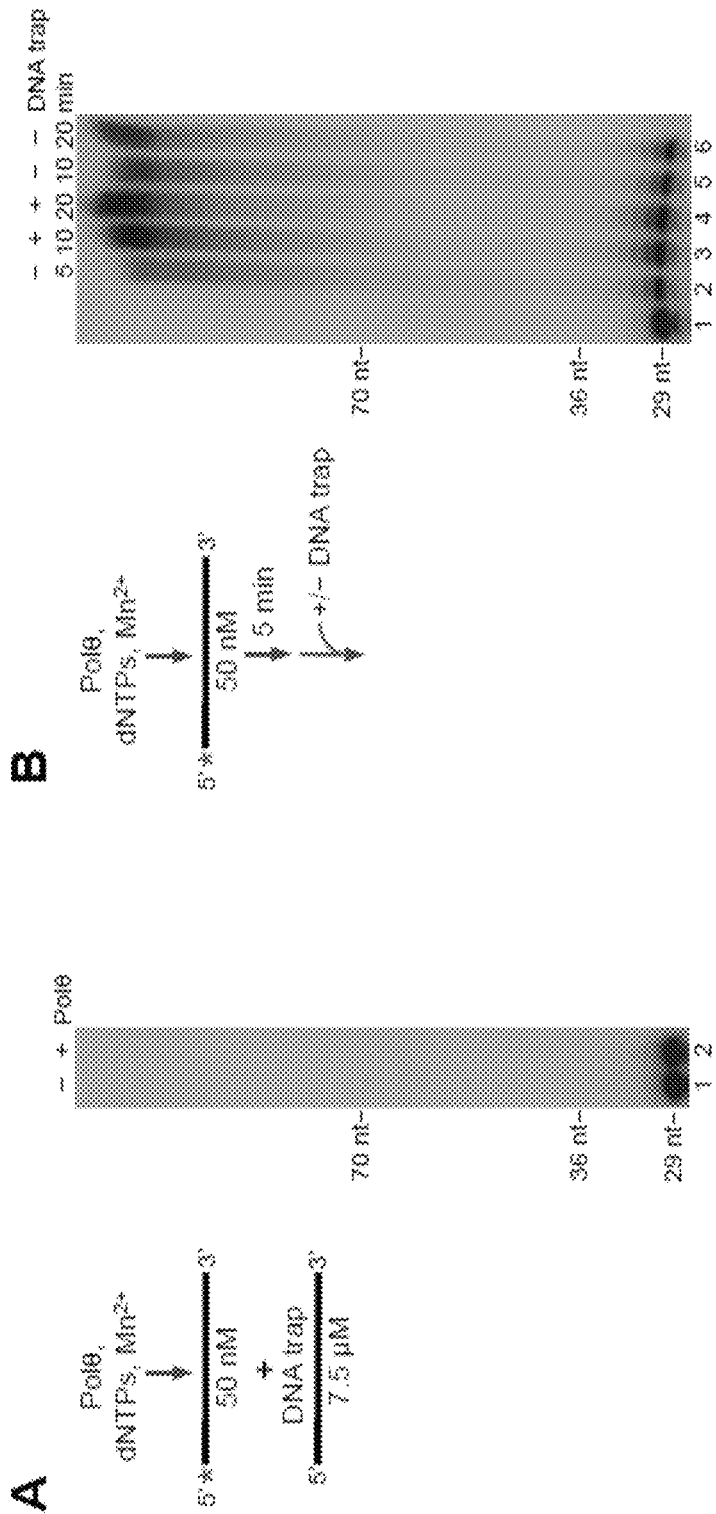
FIG. 17A and FIG. 17B, depicts results of experiments demonstrating that Polθ-Mn$^{2+}$ exhibits processive terminal transferase activity.

Next, it was examined whether Polθ-Mn$^{2+}$ acts processively during ssDNA extension and whether the polymerase can switch between the three different modes of terminal transferase activity without dissociating from the initial ssDNA template. The processivity of Polθ-Mn$^{2+}$ was tested on ssDNA by allowing the polymerase to extend the ssDNA for an initial 5 min followed by the addition of a 150-fold excess of unlabeled ssDNA which sequesters the polymerase if it dissociates from the initial radio-labeled ssDNA during the reaction (FIG. 17B). Remarkably, addition of the ssDNA trap had no effect on Polθ-Mn$^{2+}$ terminal transferase activity, demonstrating that the polymerase performs ssDNA extension with high processivity. As a control, 150-fold excess of unlabeled ssDNA effectively sequesters the polymerase from solution (FIG. 17A). Since Polθ-Mn$^{2+}$ exhibits three different modes of terminal transferase activity under the same conditions (FIG. 11A), these results indicate the polymerase switches between these distinct activities without dissociating from the initial ssDNA.

Figures 18A, 18B:
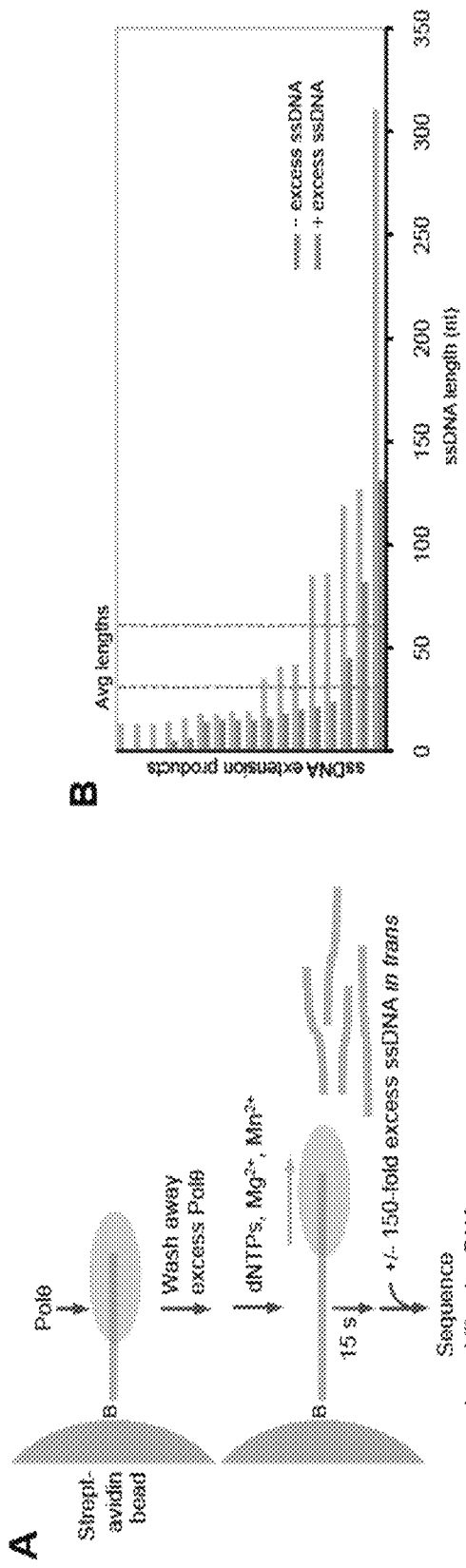
FIG. 18A through FIG. 18D, depicts results of experiments demonstrating that Polθ-Mn$^{2+}$ oscillates between different terminal transferase activities in the presence of a DNA trap.
Figure 18C:
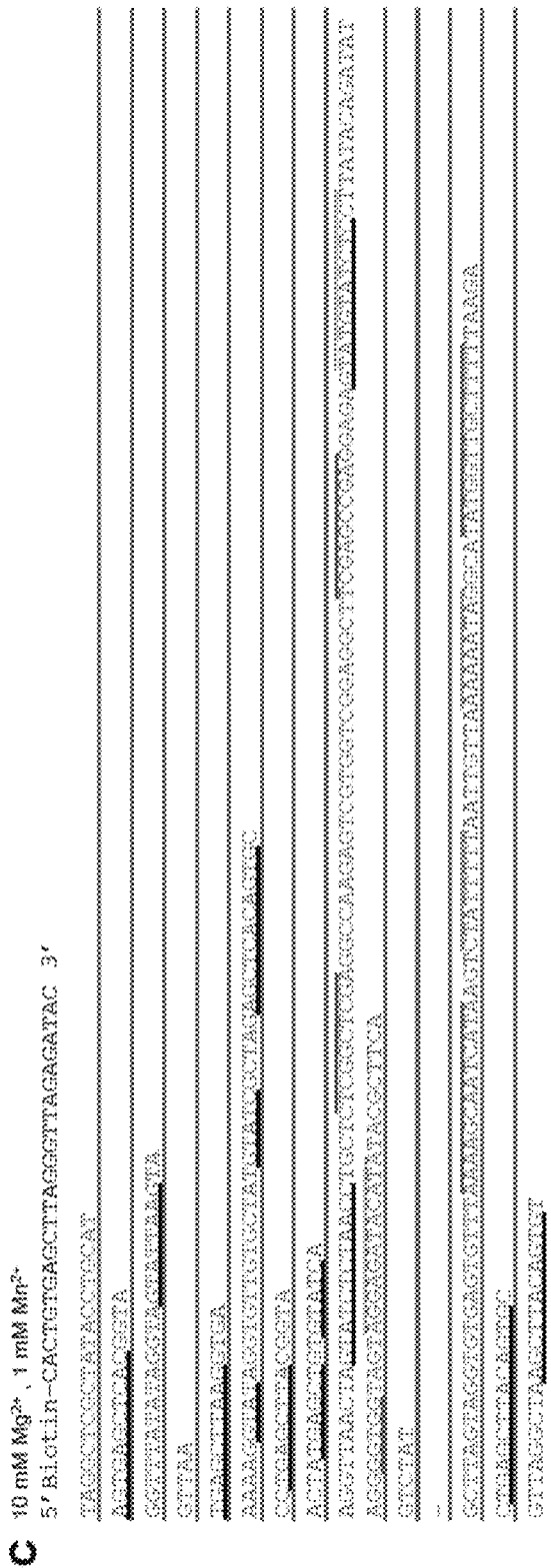
Figure 18D:
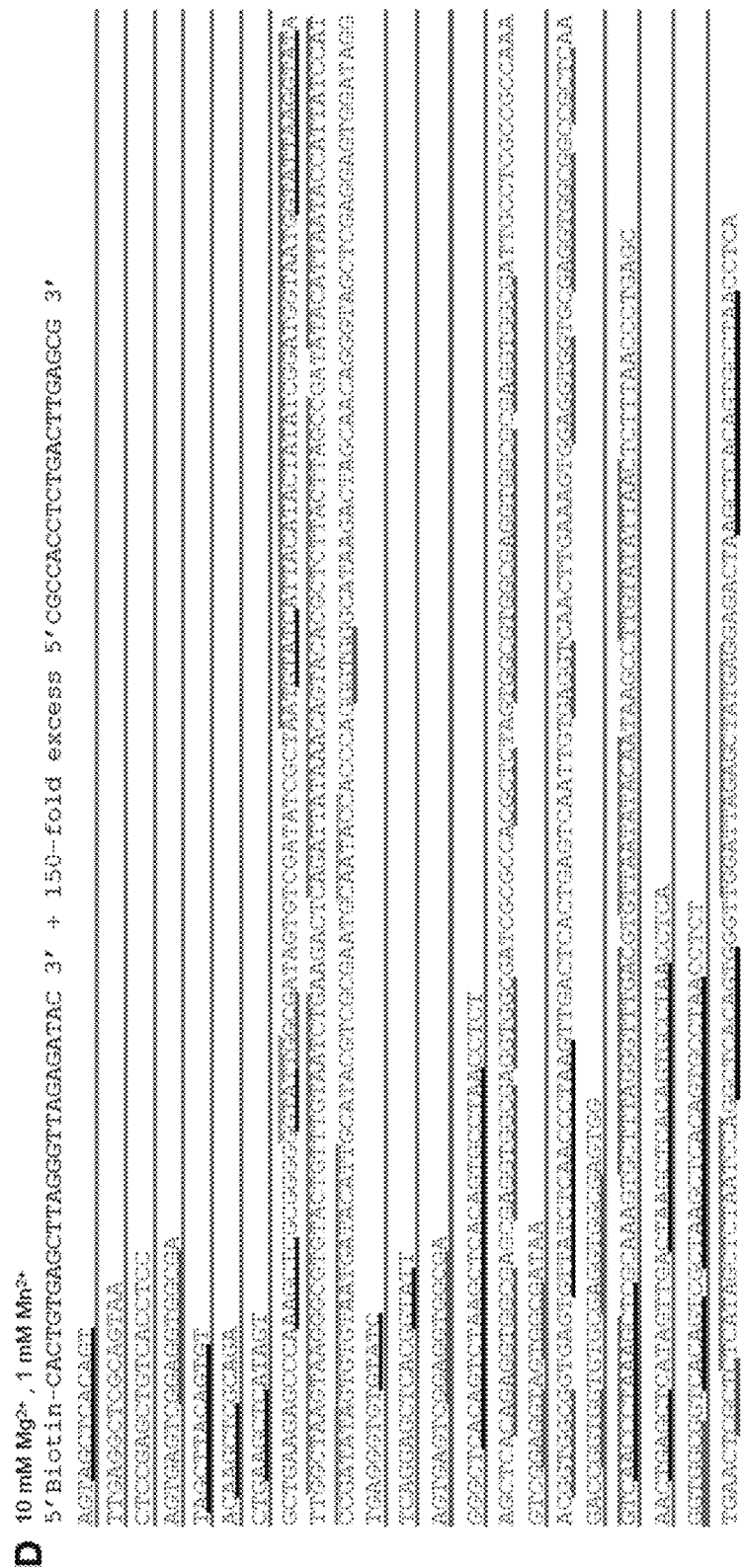

To further test the processivity of this switching mechanism ssDNA extension was performed in the presence and absence of a ssDNA trap in solid-phase which enabled removal of excess unbound polymerase from solution (FIG. 18). For example, Polθ was first allowed to bind ssDNA immobilized to streptavidin beads. Then, excess unbound Polθ was removed by thorough washing of the beads. Next, the reaction was initiated by the addition of dNTPs in buffer containing 10 mM Mn$^{2+}$ and 1 mM Mn$^{2+}$. After 15 seconds, a 150-fold excess of ssDNA trap was added, whereas the negative control reaction contained no trap. Following completion of the reactions, the immobilized ssDNA was isolated and sequenced. Consistent with the results obtained in FIG. 17, the ssDNA trap did not suppress Polθ terminal transferase activity. In fact, the data indicate that the addition of excess ssDNA increases the length of ssDNA extension products generated by Polθ in solid-phase (FIGS. 18B, 18C and 18D). This suggests that use of a template in trans enables Polθ terminal transferase activity rather than suppressing it. Consistent with this, sequence analysis shows that Polθ frequently utilizes the ssDNA trap as a template in trans (FIG. 18D). The polymerase also performs template independent and snap-back replication activities when the ssDNA trap is present (FIG. 18D). Since Polθ is highly processive during ssDNA extension (FIG. 17), these data provide strong support for a model whereby a single polymerase oscillates between the three different modes of terminal transferase activity without dissociating from the initial ssDNA template. Importantly, using intracellular concentrations of Mg$^{2+}$ (1 mM) and Mn$^{2+}$ (50 μM), Polθ remains effective in extending ssDNA and utilizes a combination of templated and non-templated mechanisms during this activity (FIG. 19).

Figure 13A:
FIG. 13A through FIG. 13D, depicts results of experiments demonstrating that Polθ oscillates between three different modes of terminal transferase activity during alternative end-joining in vitro.
Figure 20A:
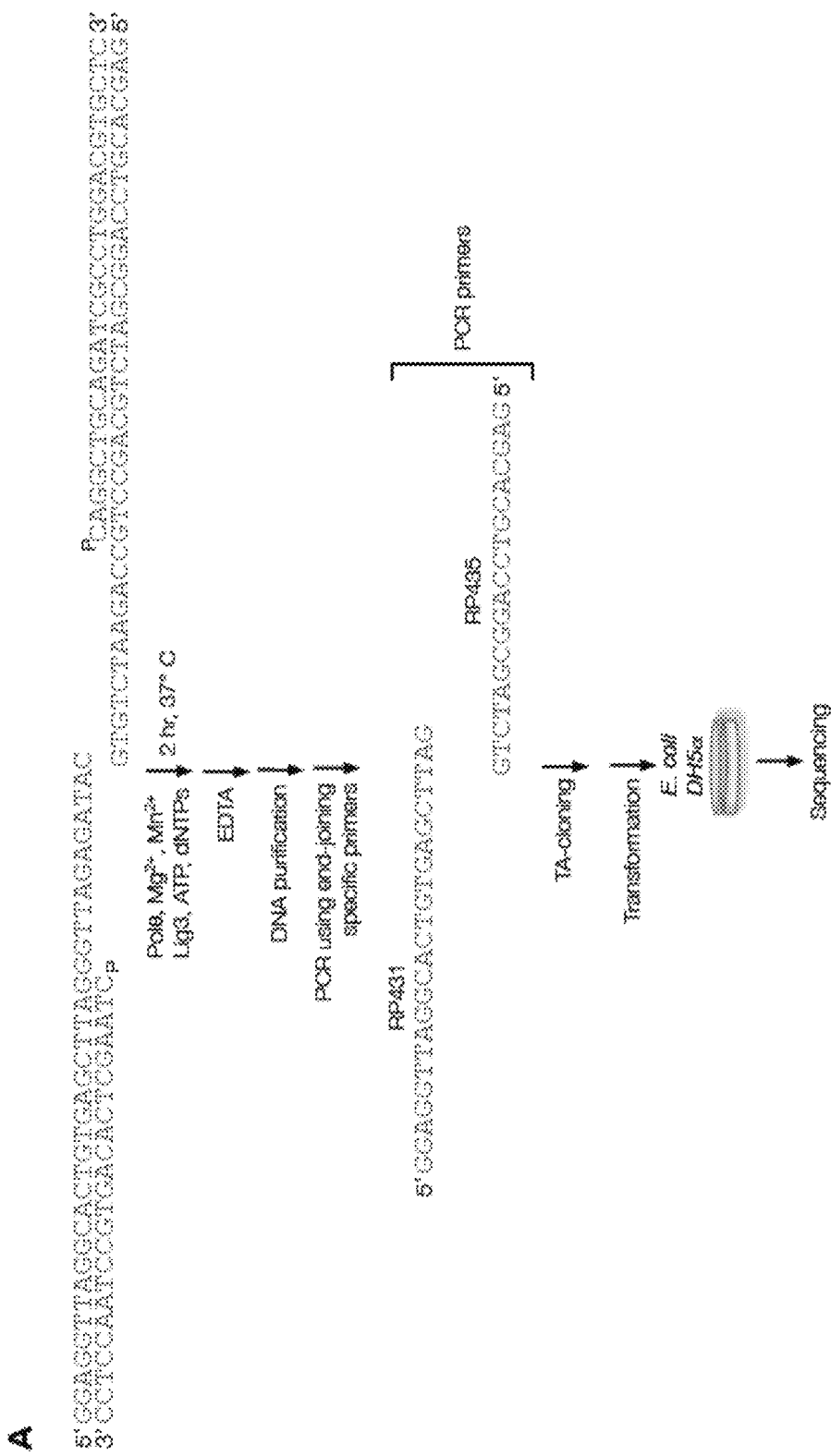
FIG. 20A through FIG. 20C, depicts results of experiments demonstrating Polθ mediated alt-EJ in vitro.
Figures 20B, 20C:
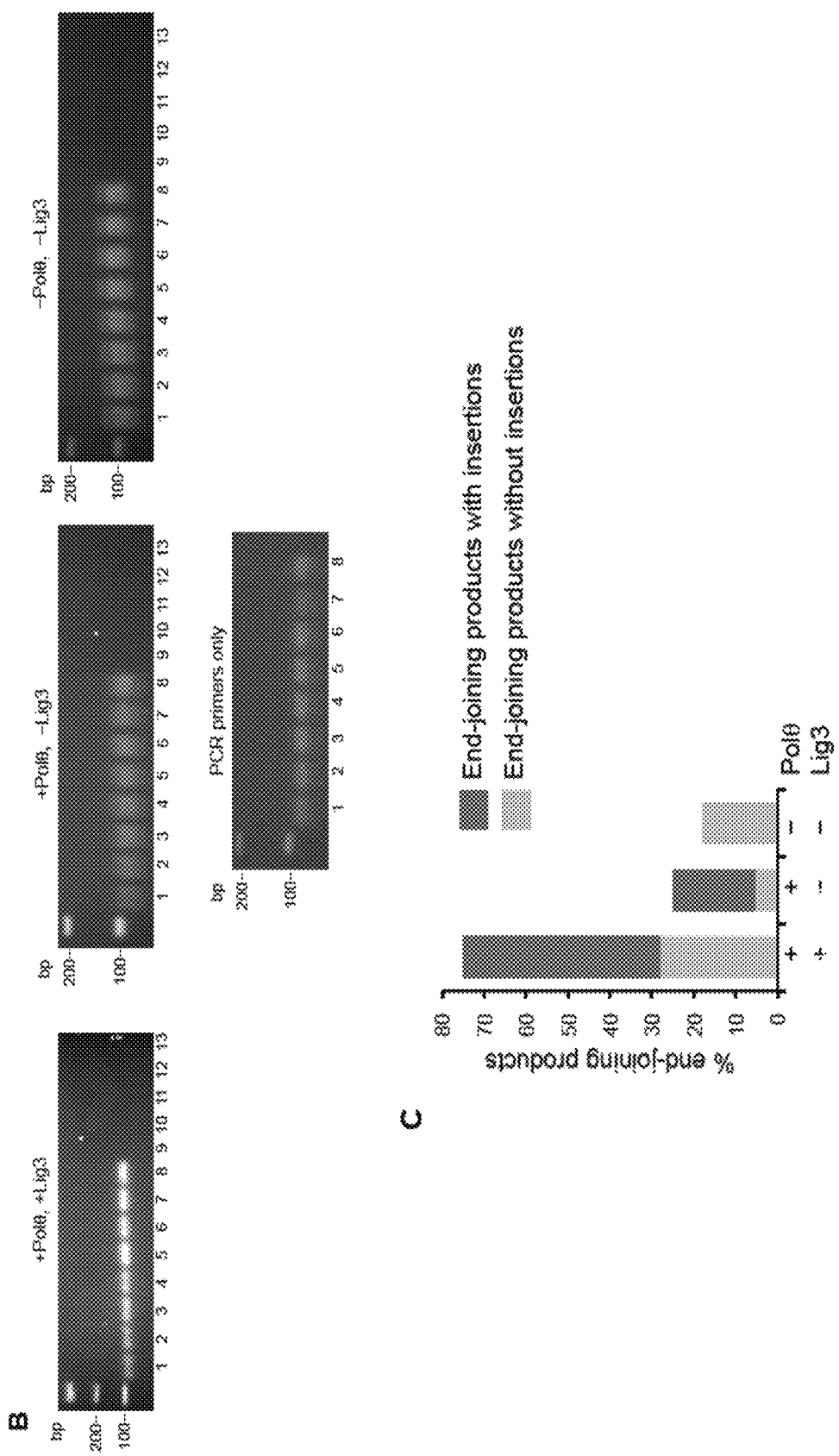

Polθ Oscillates Between Three Modes of Terminal Transferase Activity During Alt-EJ Next, Polθ terminal transferase activity was examined in the context of alt-EJ. Although cellular studies have shown that Polθ expression is required for the appearance of non-templated and templated insertions at alt-EJ repair junctions, it remains unknown whether additional factors or co-factors facilitate these insertion events. For example, Polθ has been shown to promote what appears to be random nucleotide insertion tracts at alt-EJ repair junctions in mice and flies (FIG. 1B)(Chan et al., 2010; Mateos-Gomez et al., 2015). Evidence in flies, mice and worms also indicates that Polθ promotes templated nucleotide insertions, which are proposed to be due to a template copy mechanism in trans (FIG. 7C) (Chan et al., 2010; Koole et al., 2014). To determine whether Polθ is solely responsible for these insertions, and whether the three mechanisms of terminal transferase activity identified herein facilitate these insertions, a minimal alt-EJ system in vitro were reconstituted. Here, two DNA substrates containing a 3' overhang, herein referred to as partial ssDNA (pssDNA), and a single base pair of microhomology (G:C) at their 3' termini were incubated with Polθ, Lig3, ATP, and dNTPs in buffer containing a high ratio of Mg$^{2+}$ to Mn$^{2+}$ which models cellular conditions (FIG. 13A, top). Although Polθ can perform MMEJ without Lig3 by promoting templated extension in trans (FIG. 7A) (Kent, 2015), the pssDNA substrates in the current assay lack sufficient microhomology for MMEJ, but contain a 5' phosphate on their short strands which can support ligation of the opposing 3' overhang that is extended by the polymerase (FIG. 13A, top). Control experiments show that the addition of Polθ and Lig3 is required for efficient alt-EJ, and that insertions depend on Polθ (FIG. 20C). These results are expected since Lig3 is required for most alt-EJ in cells and therefore likely functions with Polθ which facilitates insertions (Audebert et al., 2004; Simsek et al., 2011). Following termination of the reaction by EDTA, DNA was purified then end-joining products were amplified by PCR and individually sequenced from cloning vectors (FIGS. 20A and 20B).

Figures 13B, 13C, 13D:
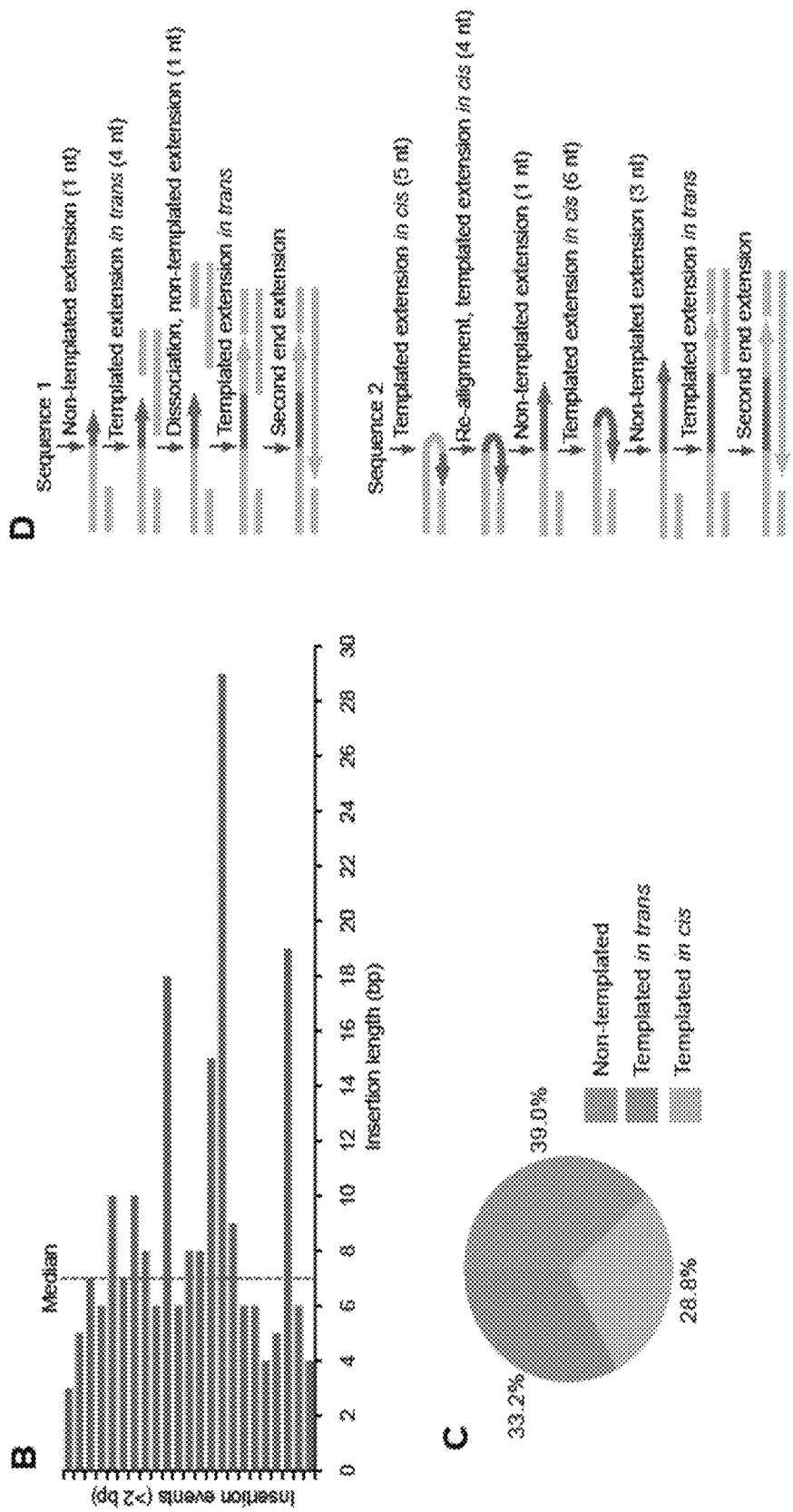

To gain significant insight into the mechanisms of Polθ terminal transferase activity during alt-EJ, tracts greater than 2 nt in length were analyzed which reveal information regarding template dependency. Remarkably, Polθ generated both random and templated nucleotide insertions at repair junctions (FIG. 13A), which is similar to the results obtained in FIG. 11. In the case of templated insertions, sequence tracts that appear to be due to both templated extension in cis (snap-back replication; red underlines) and in trans (grey underlines) were observed. A median insertion length of 7 bp was observed (FIG. 13B), and cumulative analysis of individual nucleotide insertion events reveals a roughly equal proportion of insertions due to the three modes of terminal transferase activity identified in FIG. 11, for example non-templated extension, templated extension in cis, and templated extension in trans (FIG. 13C). Polθ switching activity was modeled based on the sequence generated, in this case during alt-EJ (FIG. 13D). Consistent with the mechanism identified in FIG. 11, sequence traces strongly suggest spontaneous and rapid switching between the three different terminal transferase activities (FIG. 13D).

Figure 21A:
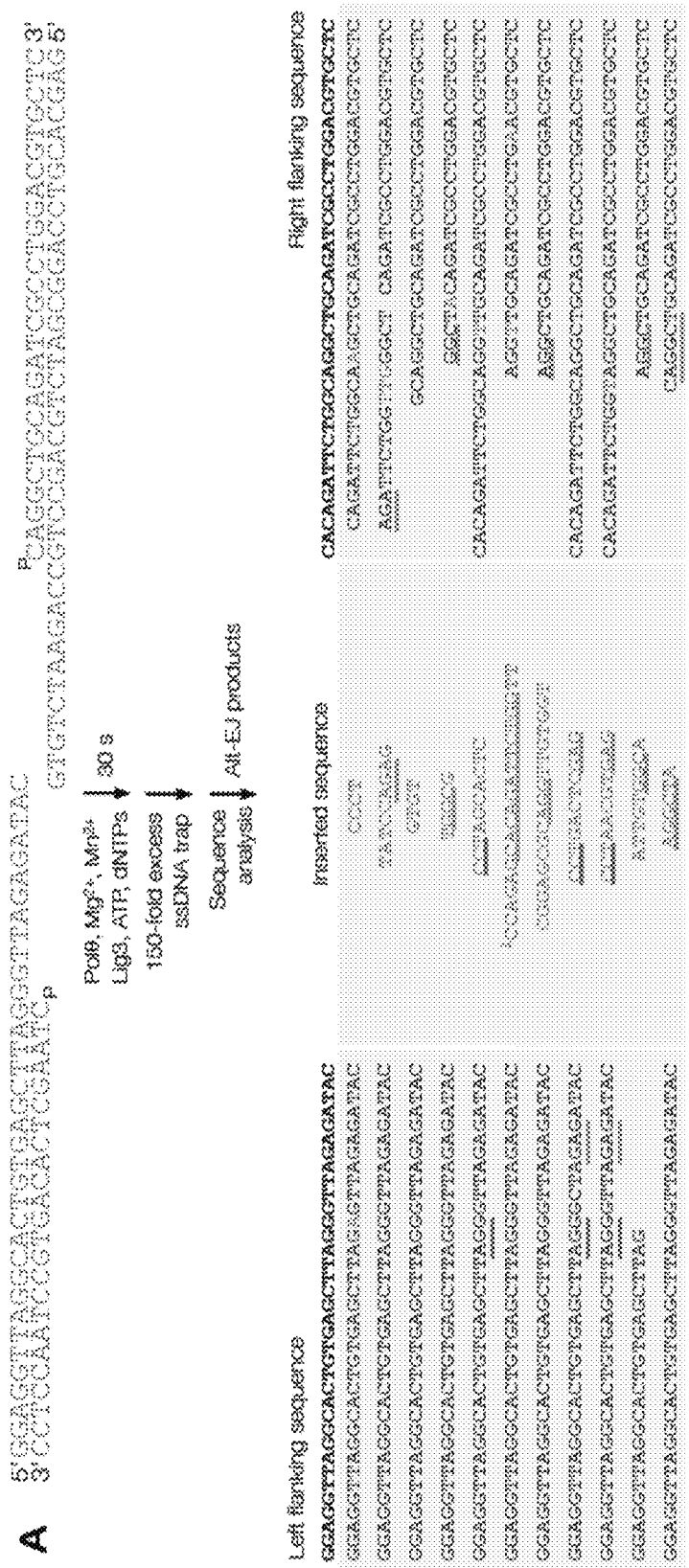
FIG. 21A and FIG. 21B, depicts results of experiments demonstrating that Polθ acts processively during alt-EJ in vitro.
Figure 21B:
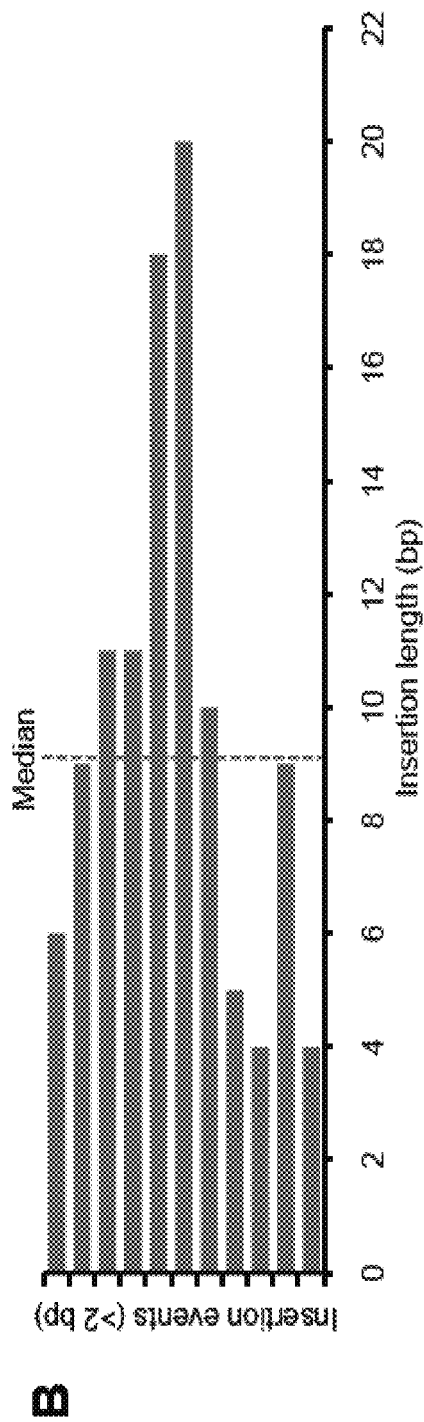
Figures 22A, 22B, 22C:
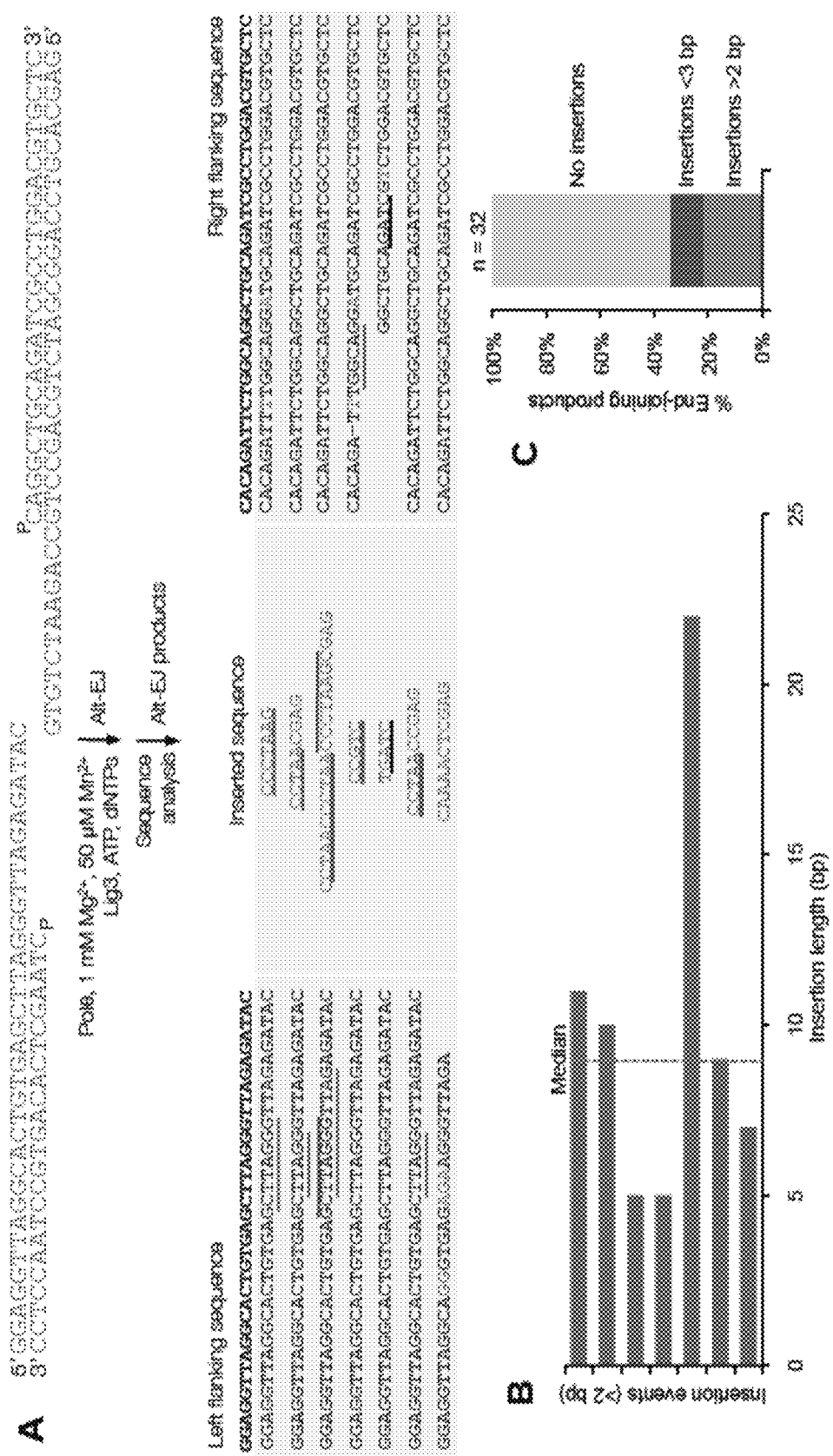
FIG. 22A through FIG. 22C, depicts results of experiments demonstrating that Polθ generates insertions during alt-EJ in the presence of low concentrations of Mg$^{2+}$ and Mn$^{2+}$.

It was next examined whether the polymerase acts processively to generate insertions during alt-EJ. To test this, the alt-EJ reaction in vitro was repeated with the addition of a 150-fold excess of ssDNA trap 15 seconds after the reaction was initiated. The results show that Polθ generates similar insertion tract lengths in the presence and absence of the ssDNA trap (compare FIG. 13 and FIG. 21). Thus, these data also indicate that Polθ acts processively during alt-EJ which provides further support for a model whereby a single polymerase oscillates between the different terminal transferase activities prior to dissociating from the initial substrate. Importantly, further alt-EJ experiments show that Polθ generates similar size insertions by a combination of templated and non-templated mechanisms in the presence of 1 mM $Mg^{2+}$ and 50 μM $Mn^{2+}$ which model intracellular concentrations (FIG. 22).

Figure 14A:
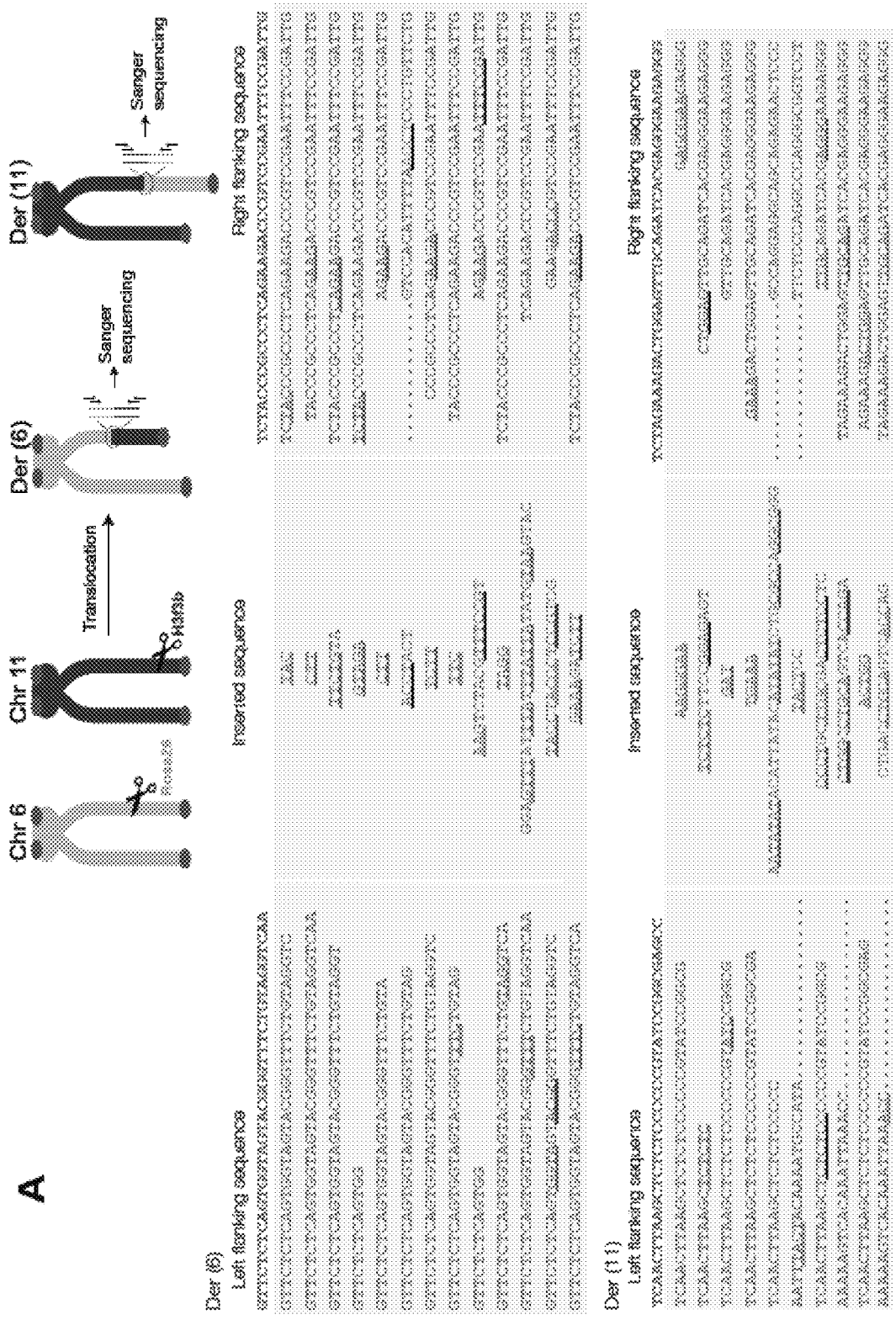
FIG. 14A through FIG. 14D, depicts results of experiments demonstrating that Polθ oscillates between three different modes of terminal transferase activity during alternative end-joining in vivo.
Figures 14B, 14C, 14D:
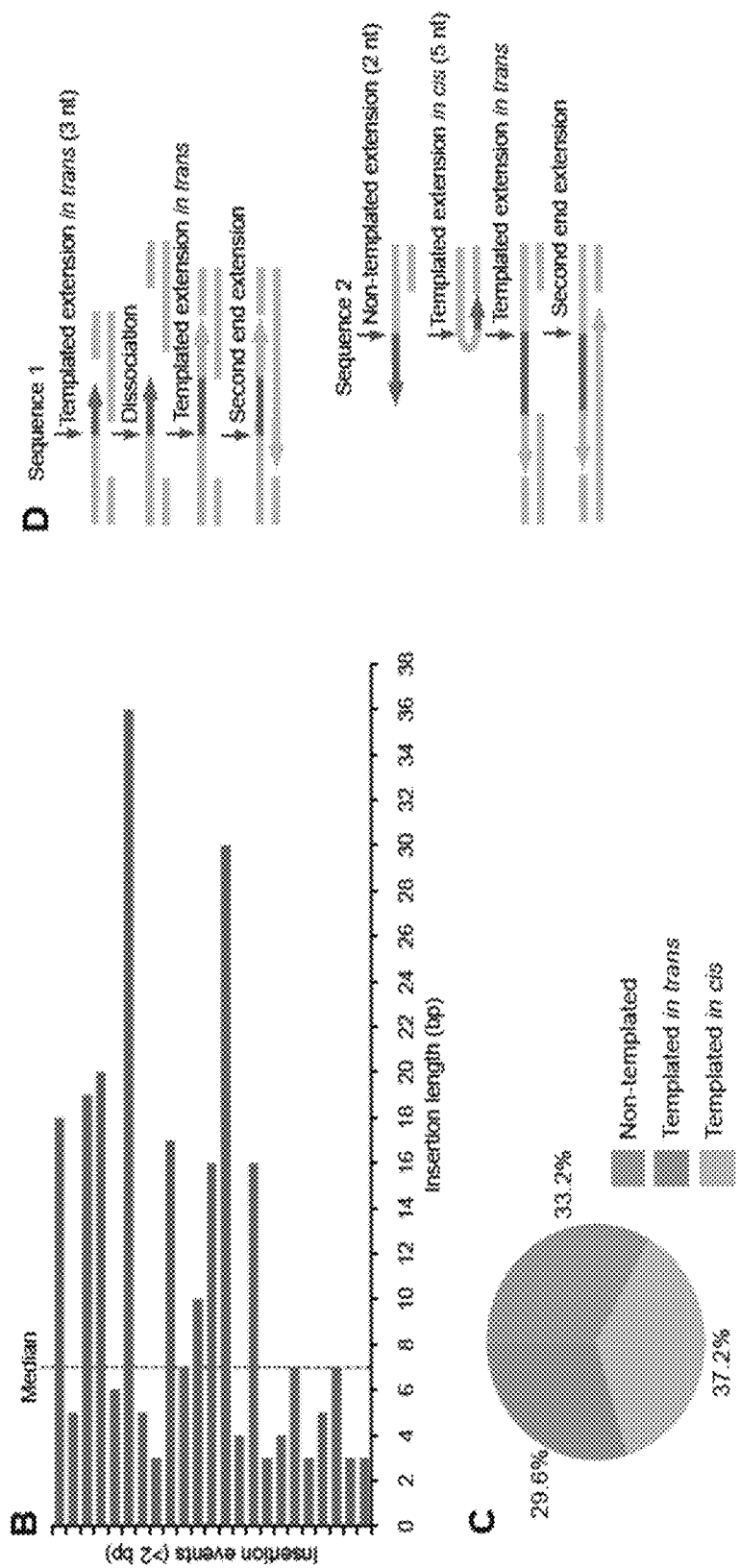
Figure 23:
FIG. 23 depicts results of experiments demonstrating large insertions copied from remote donor locations. Scheme for Polθ mediated alt-EJ of site-specific DSBs in mouse embryonic stem cells (top). Insertion sequences of alt-EJ products generated by Polθ in cells (bottom three panels). Probable remote donor sites listed at right based on sequence similarity. The large templated insertions copied from remote donor locations are likely due to strand invasion into duplex DNA followed by D-loop extension and dissociation.
Figure 24A:
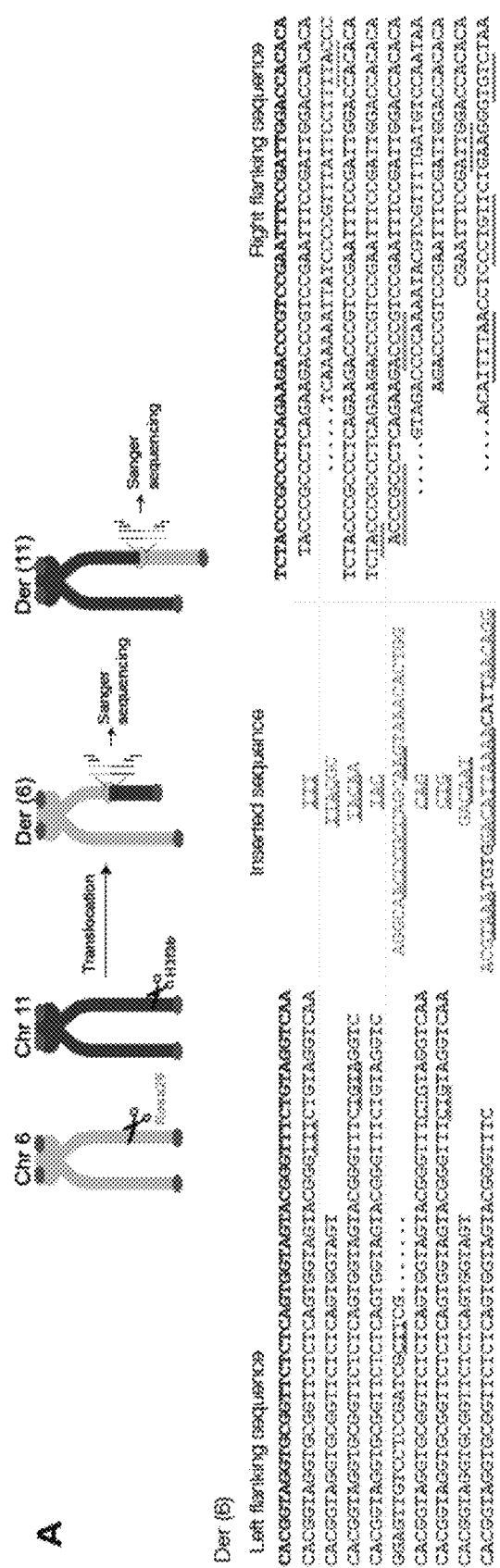
FIG. 24A and FIG. 24B, depicts results of experiments demonstrating additional sequence analysis of alternative end-joining products generated in vivo.
Figure 24B:
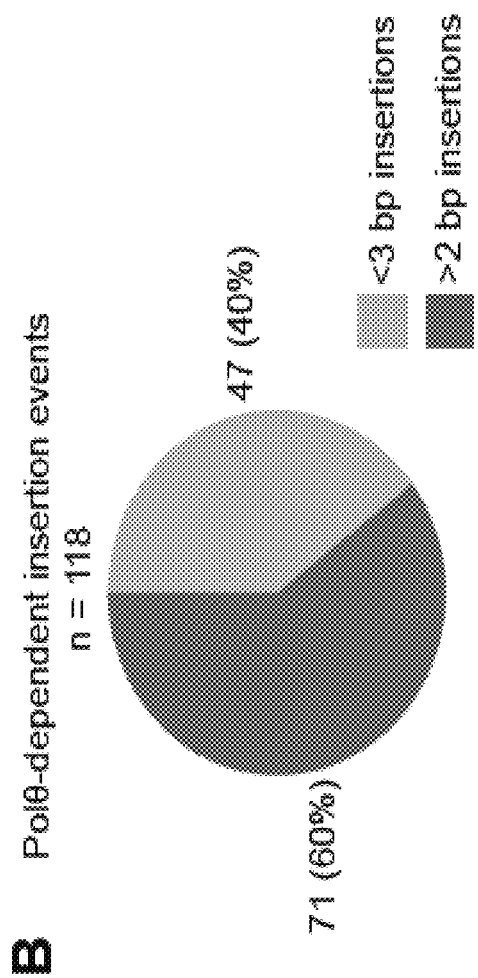

To test whether Polθ uses this switching mechanism to generate insertions during alt-EJ in cells, insertion tracts synthesized by Polθ during alt-EJ in vivo was analyzed (FIG. 14). Here, Polθ dependent alt-EJ in mouse embryonic stem cells promotes translocations between sequence specific DSBs generated in chromosomal DNA by the CRISPR/Cas9 system, as shown in previous studies (FIG. 14A, top) (Mateos-Gomez et al., 2015). To distinguish between the different Polθ mediated activities during chromosomal translocation, junctions of events resulting from the cleavage of chromosomes 6 and 11, and subsequent formation of Der (6) and (11) were carefully analyzed. Similar to FIG. 13, junctions containing insertions >2 bp in length were analyzed. Remarkably, in the cellular alt-EJ system insertion tracts were observed that appear to be due to all three modes of Polθ terminal transferase activity (FIG. 14A). For example, similar to the results obtained in the in vitro alt-EJ system (FIG. 13), cumulative analysis of individual nucleotide insertion events produced in vivo demonstrates that Polθ generates a roughly equal proportion of insertion events due to the three different modes of terminal transferase activity (FIGS. 14A, 14B, and 14C). Templated extension in trans accounts for short sequence duplications (black and grey underlines), whereas templated extension in cis (snap-back replication) accounts for the appearance of short complementary sequence tracts (red and blue underlines) (FIG. 14A). Individual nucleotide insertion events due to non-templated extension appear to be slightly lower in the in vivo system (33.2%) compared to the in vitro system (39%), which is likely due to a lower proportion of $Mn^{2+}$ to $Mg^{2+}$ in cells. Consistent with this, events due to templated extension in cis (snap-back replication) appear slightly higher in the in vivo system (37.2%) compared to the in vitro system (28.8%). It is noted that DNA deletions were observed in both systems, albeit more frequently in cells which is likely due to nuclease activity. Deletions in the in vitro system likely result from Polθ mediated end-joining at internal sites within the 3' overhang, as shown previously (Kent, 2015). This mechanism may also contribute to deletions observed in vivo. Regardless of the specific mechanisms underlying deletion formation in each system, the insertion tracts observed in vitro and in vivo appear similar in nature in regards to template dependency (compare FIGS. 13C and 14C). Furthermore, the median insertion tract length (7 bp) generated by Polθ in vitro and in vivo was identical (compare FIGS. 13B and 14B). Thus, these data demonstrate that the reconstituted alt-EJ system closely resembles the mechanism of alt-EJ in cells. It is noted that some large (>30 bp) insertions copied from remote chromosome sites and the CRISPR/Cas9 vector were also observed in the in vivo system (FIG. 23). However, these insertions are likely due to a different mechanism such as strand invasion into duplex DNA. Additional analysis of end-joining products generated in vivo demonstrates that Polθ preferentially produces insertions >2 bp in length, and occasionally generates relatively long insertions (i.e. >25 bp) (FIG. 24). Importantly, sequences of end-joining products generated in vivo support the same mechanism of Polθ switching observed in vitro (FIG. 14D). Altogether, the results presented in FIGS. 13 and 14 along with previous studies showing the requirement for Polθ in forming insertions indicate that Polθ is the main enzyme involved in generating insertions during alt-EJ. These results also indicate that Polθ oscillates between three different modes of terminal transferase activity to generate insertion mutations, and that $Mn^{2+}$ likely acts as a co-factor for Polθ in vivo.

Figures 25A, 25B, 25C:
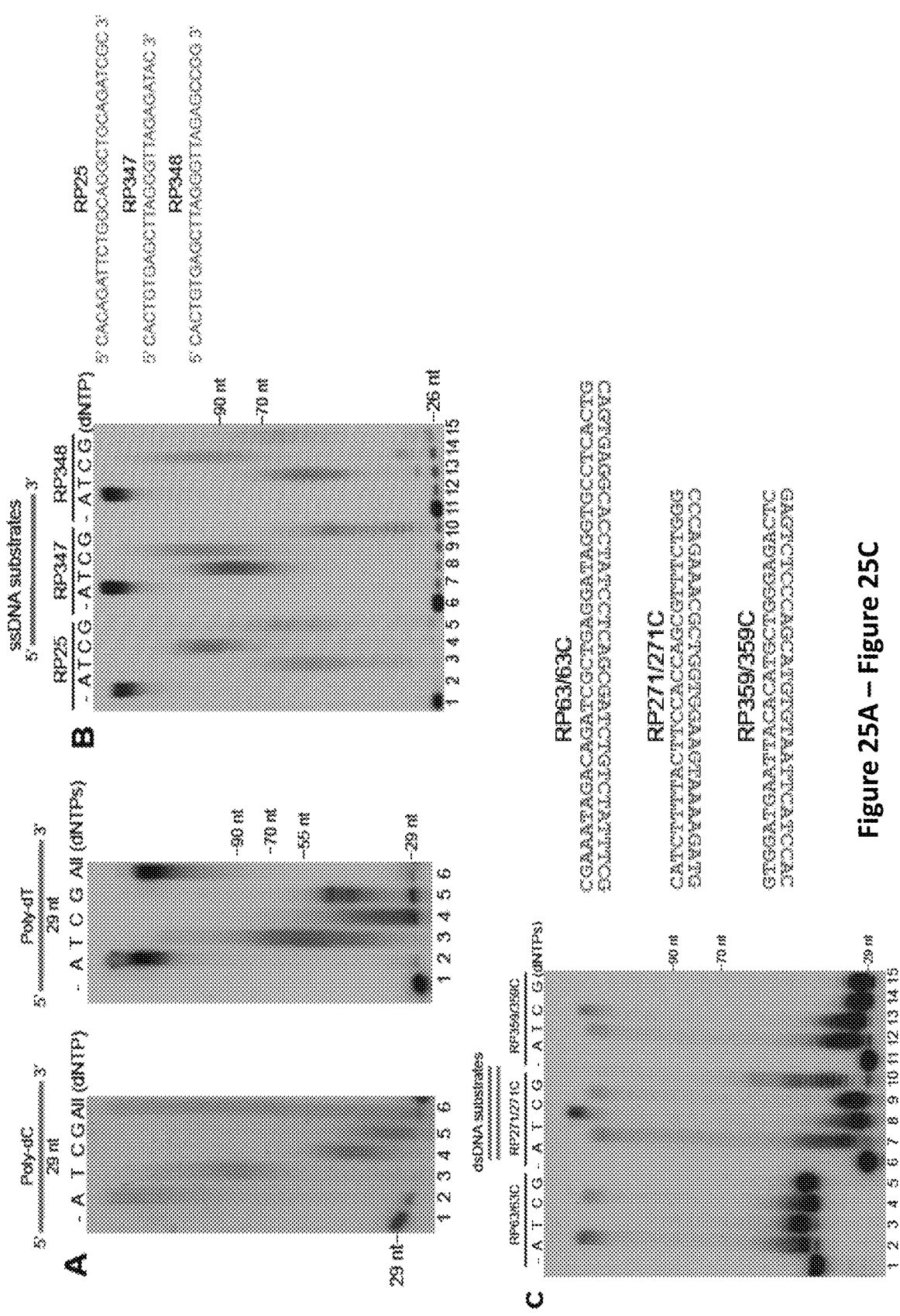
FIG. 25A through FIG. 25F, depicts results of experiments demonstrating Polθ exhibits preferential terminal transferase activity on pssDNA.
Figures 26A, 26B:
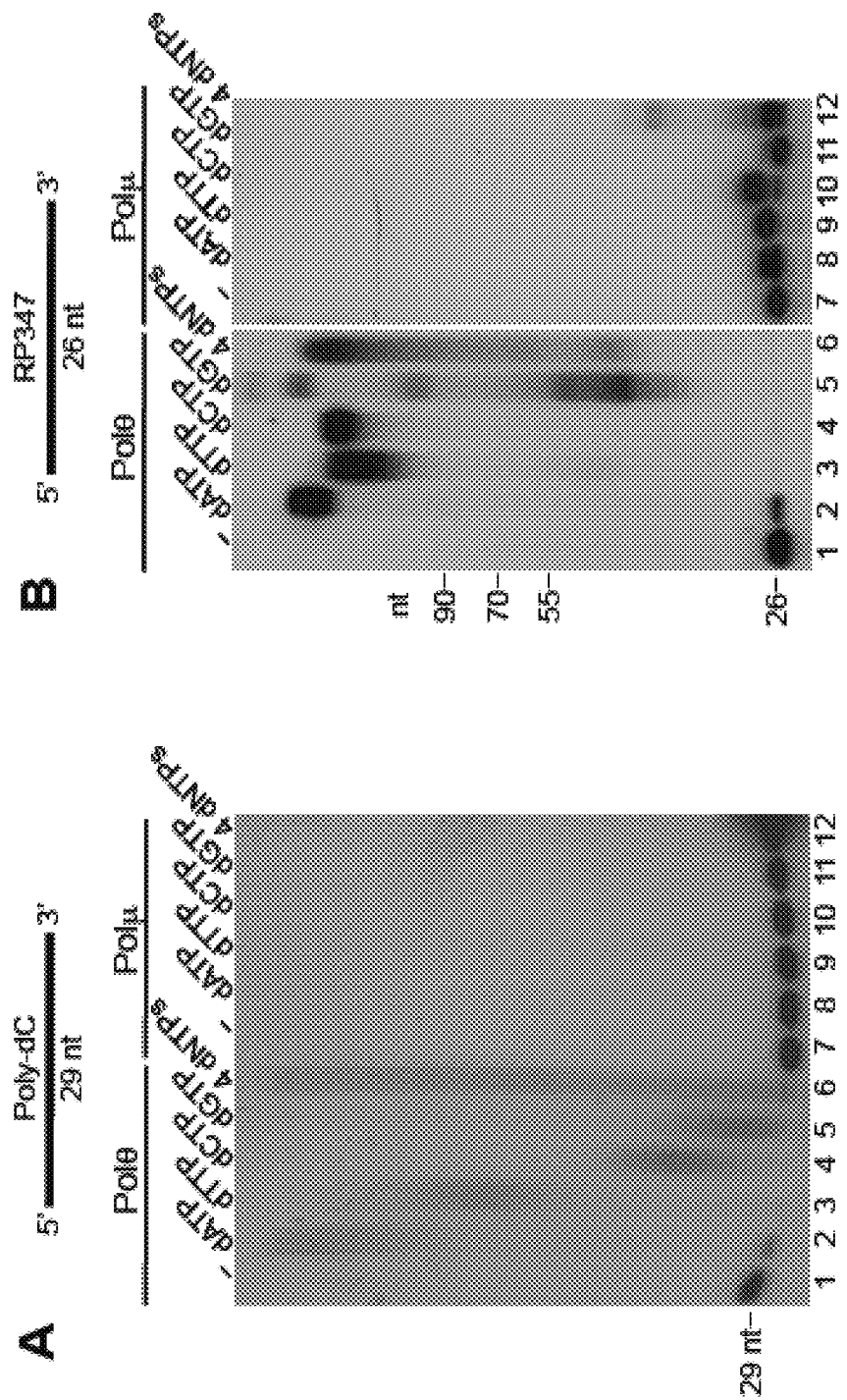
FIG. 26A and FIG. 26B, depicts results of experiments demonstrating a comparison of Polθ and Polμ terminal transferase activities with $Mn^{2+}$.

Polθ Exhibits Preferential Terminal Transferase Activity on DNA with 3' Overhangs Next, Polθ-$Mn^{2+}$ terminal transferase activity on a variety of DNA substrates was characterized. For example, Polθ-$Mn^{2+}$ was tested on homopolymeric ssDNA composed of either deoxythymidinemonophosphates (poly-dT) or deoxycytidine-monophosphates (poly-dC), and ssDNA containing variable sequences. The polymerase preferentially extended all of the substrates by more than 100 nt in the presence of deoxyadenosine-triphosphate (dATP), regardless of the sequence context (FIGS. 25A and 25B). Polymerases are known to preferentially incorporate deoxyadenosine-monophosphate (dAMP) when template base coding is not available, which is referred to as the A-rule. For example, polymerases preferentially incorporate a single dAMP opposite an abasic site or at the end of a template. Thus, the observed preferential incorporation of dAMP by Polθ-$Mn^{2+}$ is consistent with the A-rule and template-independent activity. Polθ also extended ssDNA in the presence of dTTP, dCTP, and dGTP, however, the lengths of these products were shorter than with dATP (FIGS. 25A and 25B). For example, in the case of non-homopolymeric ssDNA, Polθ-$Mn^{2+}$ transferred ~30-70 nt in the presence of dTTP, dCTP, or dGTP (FIG. 25B), which demonstrates that Polθ-$Mn^{2+}$ terminal transferase activity is relatively efficient even in the absence of the preferred dATP. Notably, the non-homologous endjoining (NHEJ) X-family polymerase, Polμ, exhibited minimal terminal transferase activity compared to Polθ under identical conditions (FIG. 26). Previous studies similarly demonstrated limited terminal transferase activity by Polμ which is most closely related to TdT (Andrade et al., 2009). Thus, to date the data presented insofar indicate that, aside from TdT, Polθ possesses the most robust terminal transferase activity for the polymerase enzyme class.

Figures 25D, 25E, 25F:
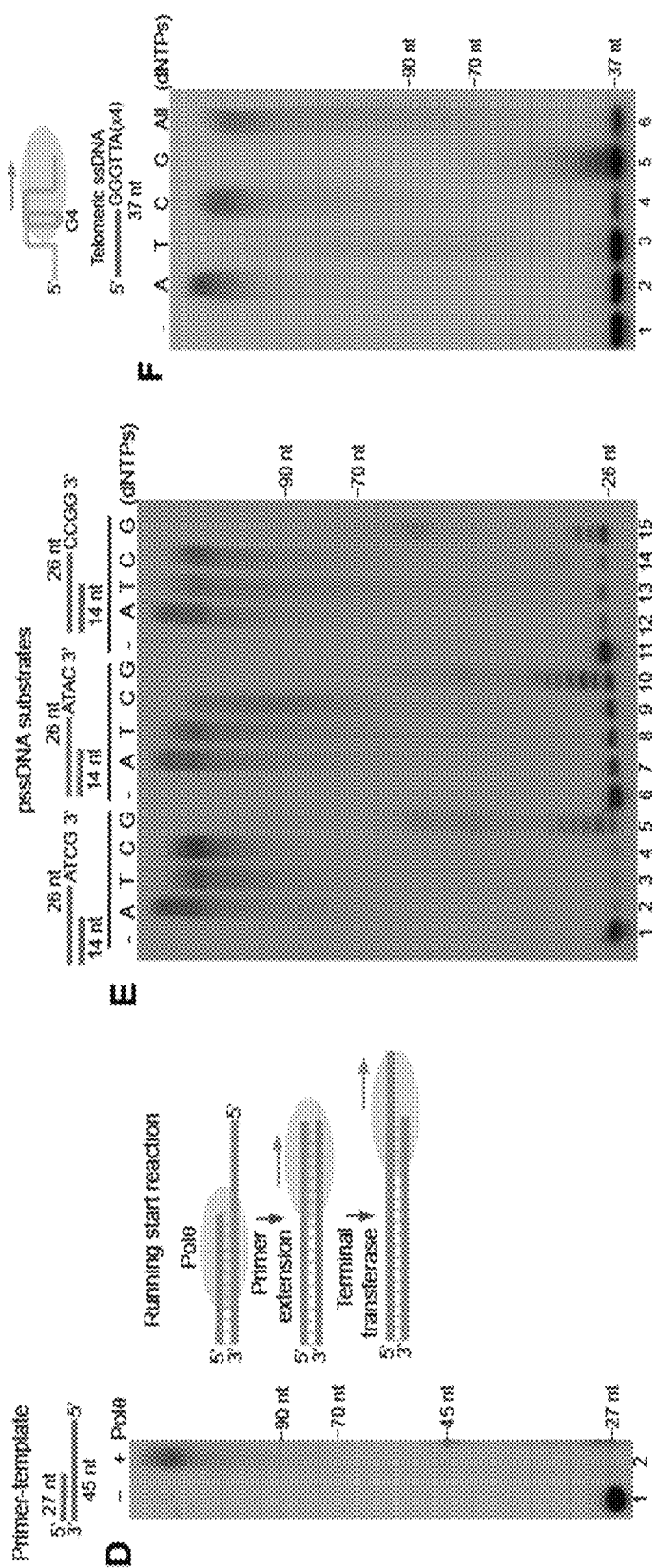

Next, the ability of Polθ-$Mn^{2+}$ to extend blunt-ended double-strand DNA (dsDNA) was examined. The results show that Polθ efficiently extends duplex DNA, however, this is limited to only 1-2 nucleotides which may be due to a lower affinity of the polymerase for blunt-ended DNA (FIG. 25C). Interestingly, Polθ efficiently extended a primer-template far beyond the downstream end of the template (FIG. 25D, left). Thus, the polymerase performs efficient long-range extension of dsDNA when given a running start (FIG. 25D, right schematic).

Considering that Polθ is thought to act on DSBs partially resected by MRN and CtIP during MMEJ/alt-EJ (Kent, 2015), its terminal transferase activity on pssDNA was examined. Remarkably, Polθ-$Mn^{2+}$ exhibited the most efficient terminal transferase activity on pssDNA (FIG. 25E). For example, the polymerase extended the pssDNA substrates to longer lengths with dTTP and dCTP, whereas dGTP was still limiting (compare FIG. 25E with FIG. 25B).

Consistent with its role in promoting alt-EJ of telomeres in cells deficient in telomere protection and NHEJ factors (Mateos-Gomez et al., 2015), Polθ exhibits efficient terminal transferase activity on ssDNA modeled after telomeres which are known to contain stable G-quadruplex (G4) secondary structures (FIG. 25F). Here again, extension in the presence of dGTP was suppressed. Considering that consecutive dGMP incorporation events limit Polθ terminal transferase activity, it is presumed that the multiple guanosines present in telomere repeats cause a similar inhibitory effect. All other nucleotides were efficiently transferred to the telomeric ssDNA substrate (FIG. 25F). Taken together, the results in FIG. 5 show that Polθ exhibits the most robust terminal transferase activity on pssDNA which is consistent with its role in MMEJ/alt-EJ, and that the polymerase is also efficient in extending various ssDNA substrates and dsDNA when given a running start.

Figure 27A:
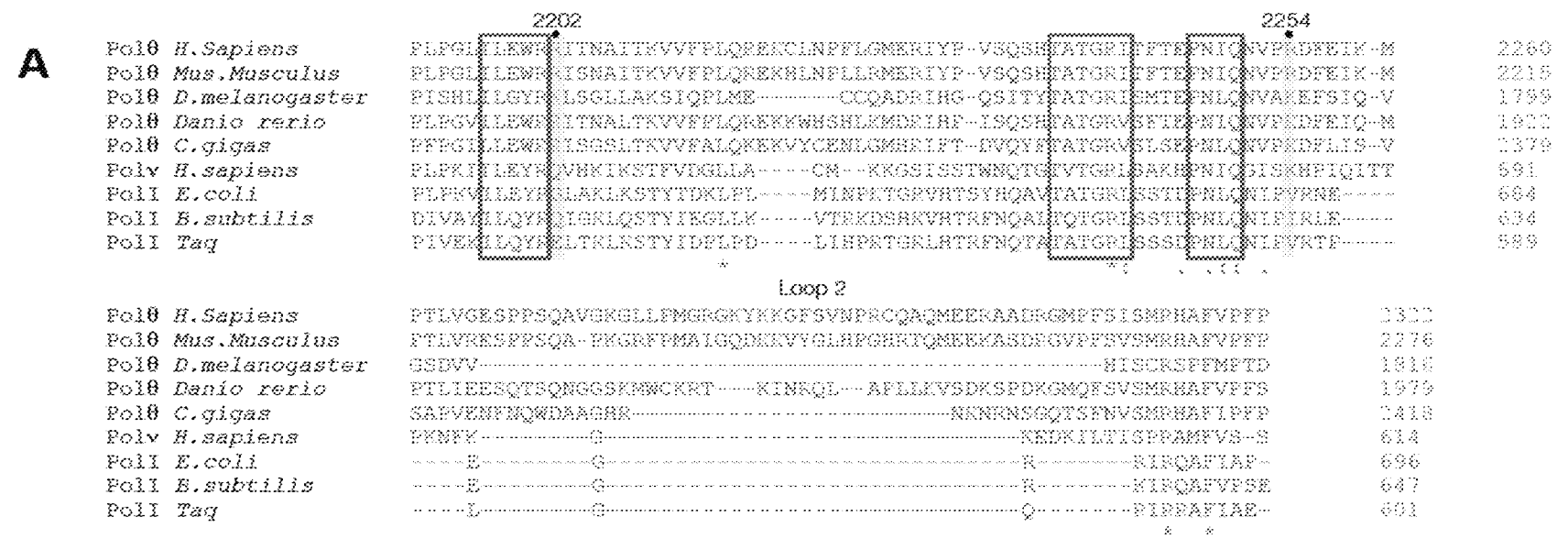
Figures 27B, 27C:
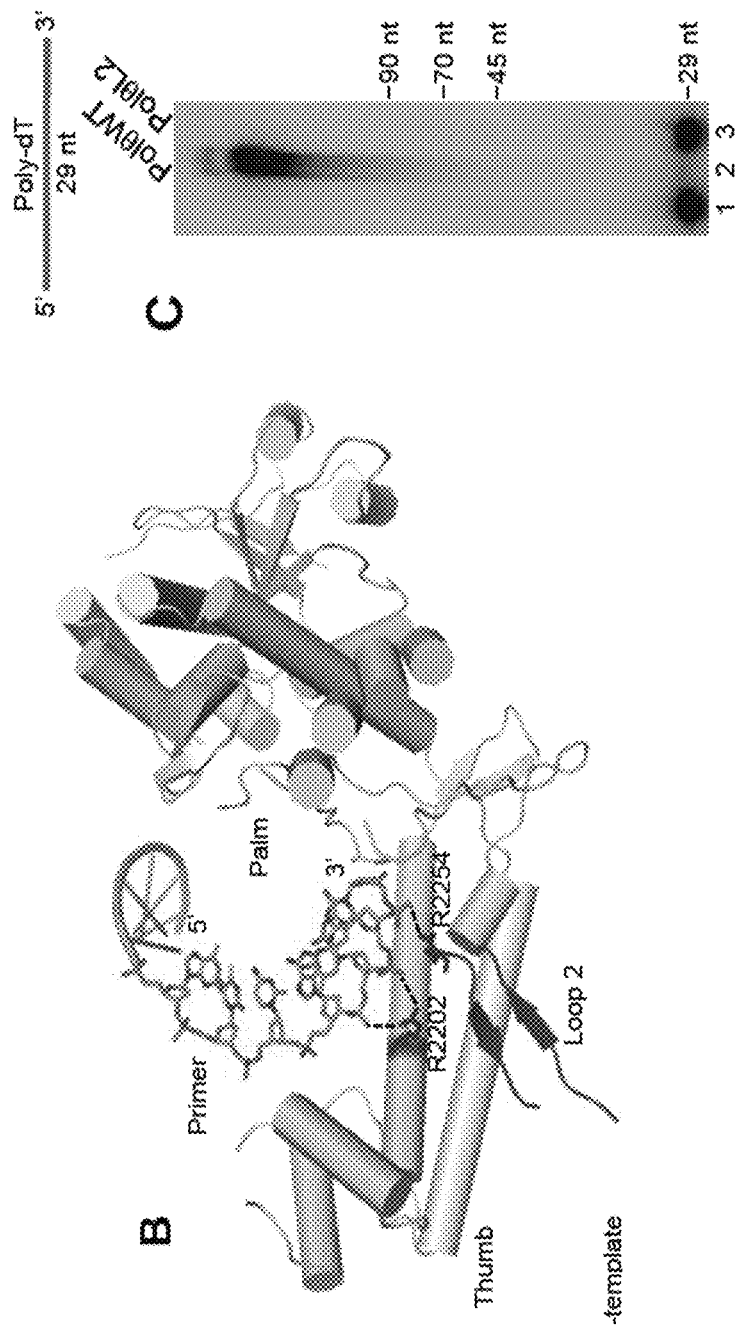
FIG. 27B depicts the structure of Polθ with ssDNA primer (PDB code 4X0P) (Zahn et al., 2015). Residues R2202 and R2254 are indicated in blue. Dotted blue lines indicate ionic interactions. Loop 2 is indicated in dark red. Thumb and palm subdomains are indicated.
FIG. 27C depicts a denaturing gel showing PolθWT and PolθL2 extension of ssDNA with 5 mM $Mn^{2+}$ and all four dNTPs.
Figures 27D, 27E, 27F, 27G:
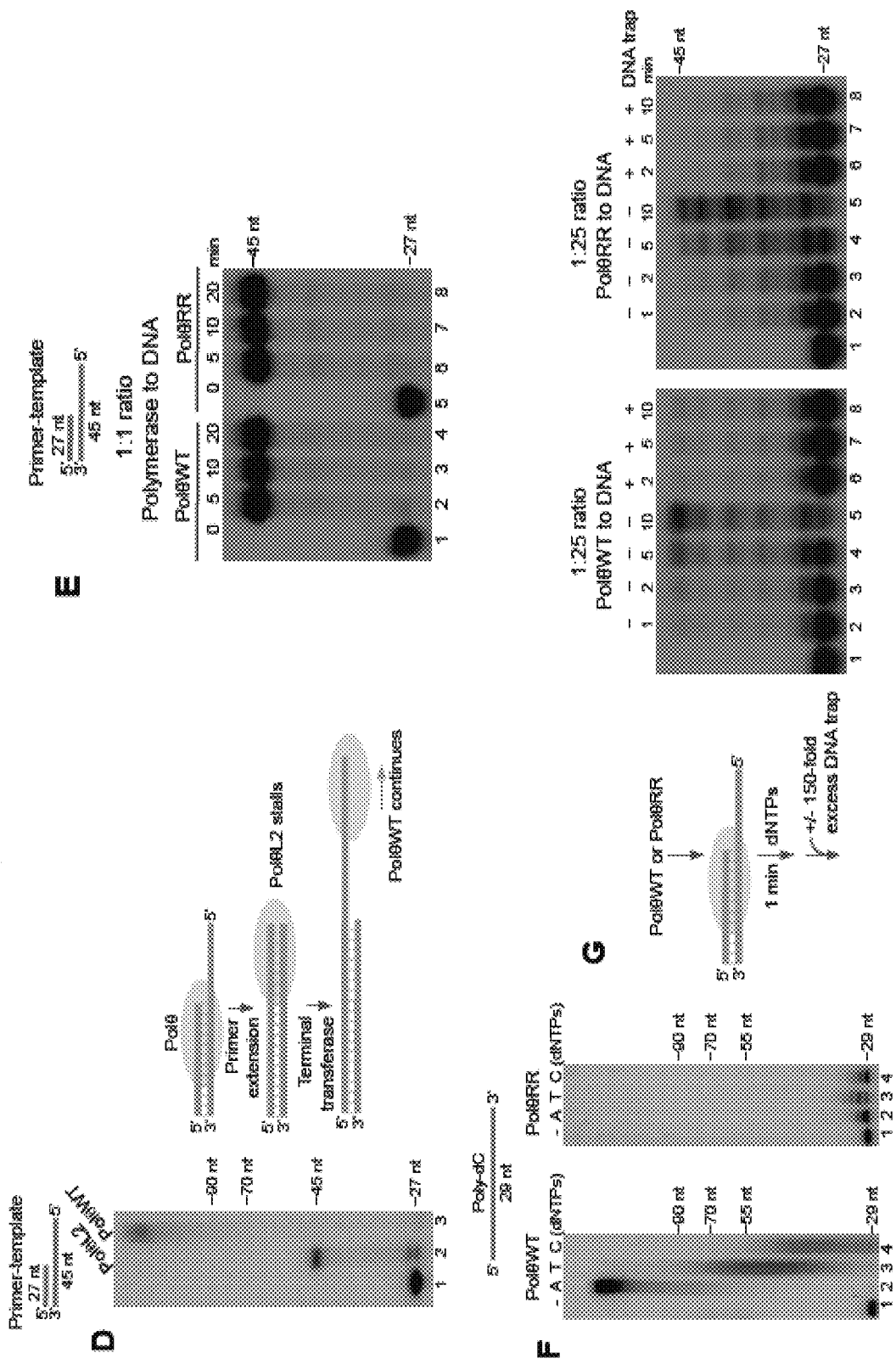
FIG. 27D depicts a denaturing gel showing PolθWT and PolθL2 extension of a primer-template with 5 mM $Mn^{2+}$ and all four dNTPs and a model of PolθWT-$Mn^{2+}$ and PolθL2-$Mn^{2+}$ activities on a primer-template.
FIG. 27E depicts a denaturing gel showing a time course of PolθWT and PolθRR extension of a primer-template in the presence of 10 mM $Mg^{2+}$ and all four dNTPs.
FIG. 27F depicts a denaturing gel Denaturing gel showing PolθWT (left) and PolθRR (right) extension of poly-dC ssDNA with 5 mM $Mn^{2+}$ and the indicated dNTPs.
FIG. 27G depicts a schematic of the assay and denaturing Denaturing gel showing PolθWT and PolθRR extension of an excess of radiolabeled primer-template with all four dNTPs and 10 mM $Mg^{2+}$ either in the presence or absence of 150-fold excess unlabeled DNA trap.

Conserved Residues Facilitate Polθ Processivity and Terminal Transferase Activity Next, the structural motifs that promote Polθ terminal transferase activity were identified. Polθ is a unique A family polymerase since it contains three insertion loops, and previous studies have shown that loop 2 is necessary for Polθ extension of ssDNA (Hogg et al., 2012; Kent, 2015). The position of this motif is conserved in Polθ and is located immediately downstream from a conserved positively charged residue, arginine (R) or lysine (K), at position 2254 (FIG. 27A). Recent structural studies of Polθ in complex with a primer-template and incoming nucleotide show that loop 2 lies relatively close to the 3' terminus of the primer, but is likely flexible in this conformation due to a lack of resolution (FIG. 27B) (Zahn et al., 2015). Considering that Polθ ssDNA extension with $Mg^{2+}$ is likely related to its activity with $Mn^{2+}$, it is possible that loop 2 would also confer template-independent terminal transferase activity. Indeed, a loop 2 deletion mutant of Polθ (PolθL2) failed to extend ssDNA under optimal template-independent terminal transferase conditions with $Mn^{2+}$ (FIG. 27C). Similar to previous results, PolθL2 fully extended a primer-template (FIG. 27D). Here, PolθWT extension continued beyond the template due to the polymerase's robust terminal transferase activity with $Mn^{2+}$ (FIG. 27D).

Structural studies showed that two conserved positively charged residues, R2202 and R2254, bind to the phosphate backbone of the 3' portion of the primer (FIGS. 27A and 27B) (Zahn et al., 2015). Since these positively charged residues are conserved in Polθ but not other A-family members (FIG. 27A), the charged residues might contribute to Polθ terminal transferase activity. First primer-extension of a double mutant version of Polθ in which R2202 and R2254 were changed to alanine (A) and valine (V), respectively (PolθRR) was tested. Recent studies showed that single R2202A and R2254V Polθ mutants were slightly defective in translesion synthesis (Zahn et al., 2015). PolθRR extended the primer in a similar manner to PolθWT (FIG. 27E). Yet, PolθRR showed a severe defect in template-independent terminal transferase activity compared to PolθWT under identical conditions with $Mn^{21}$ (FIG. 27F). Since PolθWT performs terminal transferase activity with high processivity, it was contemplated whether PolθRR exhibits reduced processivity. Indeed, PolθRR showed a significant deficiency in primer extension compared to PolθWT when a large excess of DNA was present, confirming a reduction in processivity (FIG. 27G). These data also suggest that PolθWT exhibits lower processivity during primer-template extension compared to ssDNA extension (compare FIGS. 27G and 17). Since PolθRR is defective in processivity and template-independent terminal transferase activity, this suggests that the polymerase must be processive on ssDNA to effectively perform template-independent terminal transferase activity. Together, these data identify conserved residues that contribute to Polθ terminal transferase activity by conferring processivity onto the enzyme through binding the 3' primer terminus.

Comparison of Polθ and TdT Terminal Transferase Activities

Figures 28A, 28B, 28C:
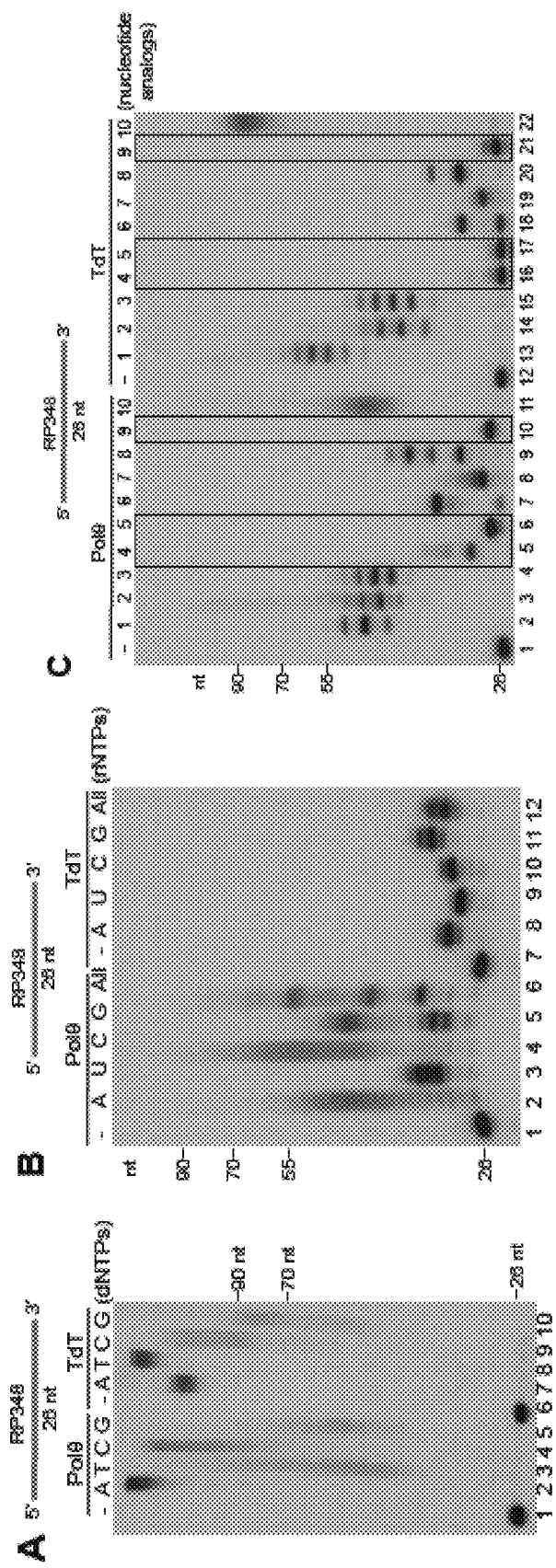
FIG. 28A through FIG. 28E, depicts a comparison of Polθ and TdT terminal transferase activities.

Importantly, terminal transferase activity is widely used to modify ssDNA ends for various types of applications including biotechnology, biomedical research, and synthetic biology. Currently, the only enzyme developed and marketed for these applications is terminal deoxynucleotidyl transferase (TdT) whose cellular function is to promote antibody diversity by transferring non-templated nucleotides to V, D and J exon regions during antibody gene maturation (Motea and Berdis, 2010). The activities of Polθ and TdT were compared as shown in FIG. 28A. Remarkably, Polθ exhibited a similar ability to extend ssDNA as TdT assayed under optimal conditions recommended by the supplier (FIG. 28A). The results also show that in this reaction Polθ and TdT preferentially utilize dATP and dTTP, respectively, which suggests different mechanisms of action (FIG. 28A).

Figure 28D:
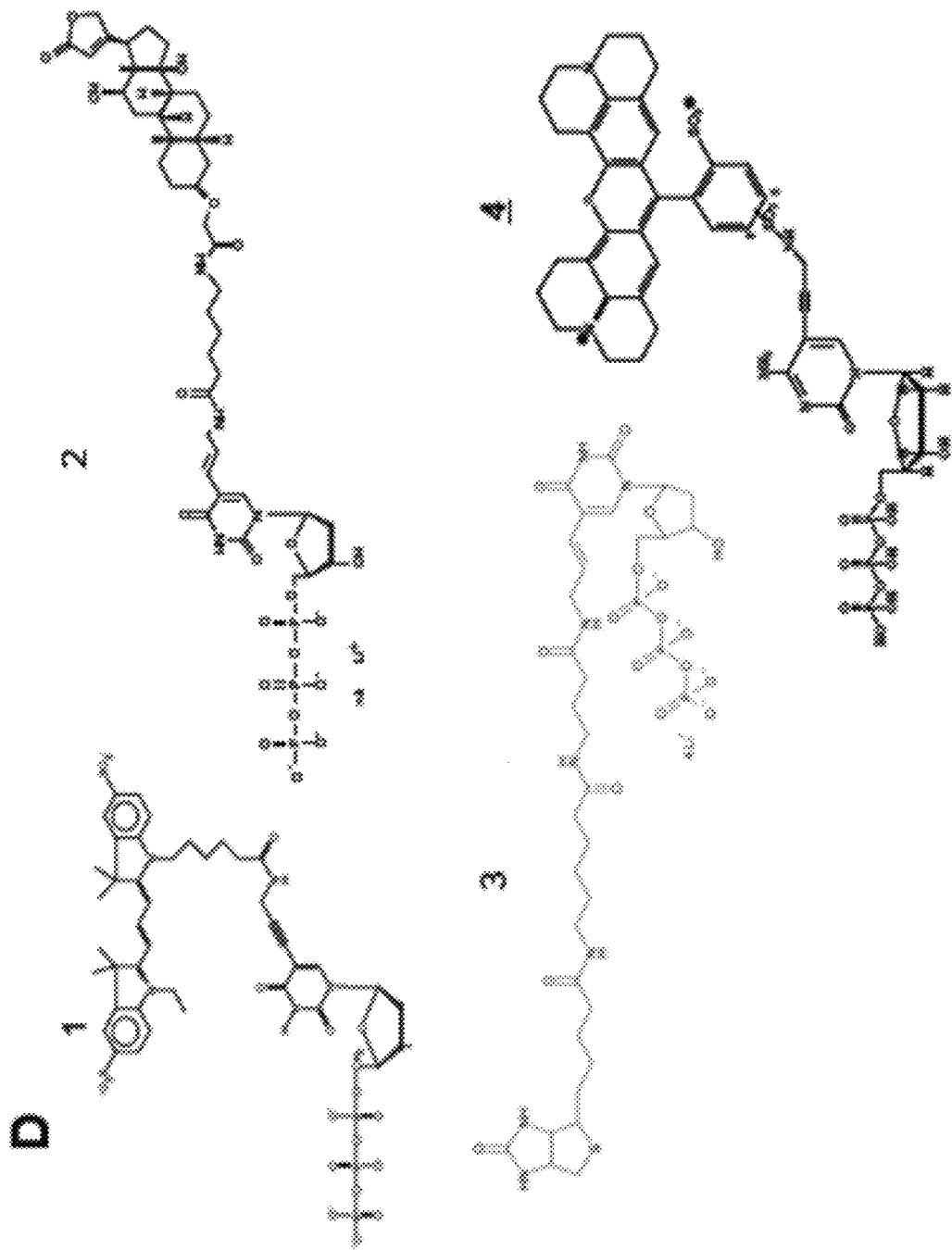
Figure 28D:
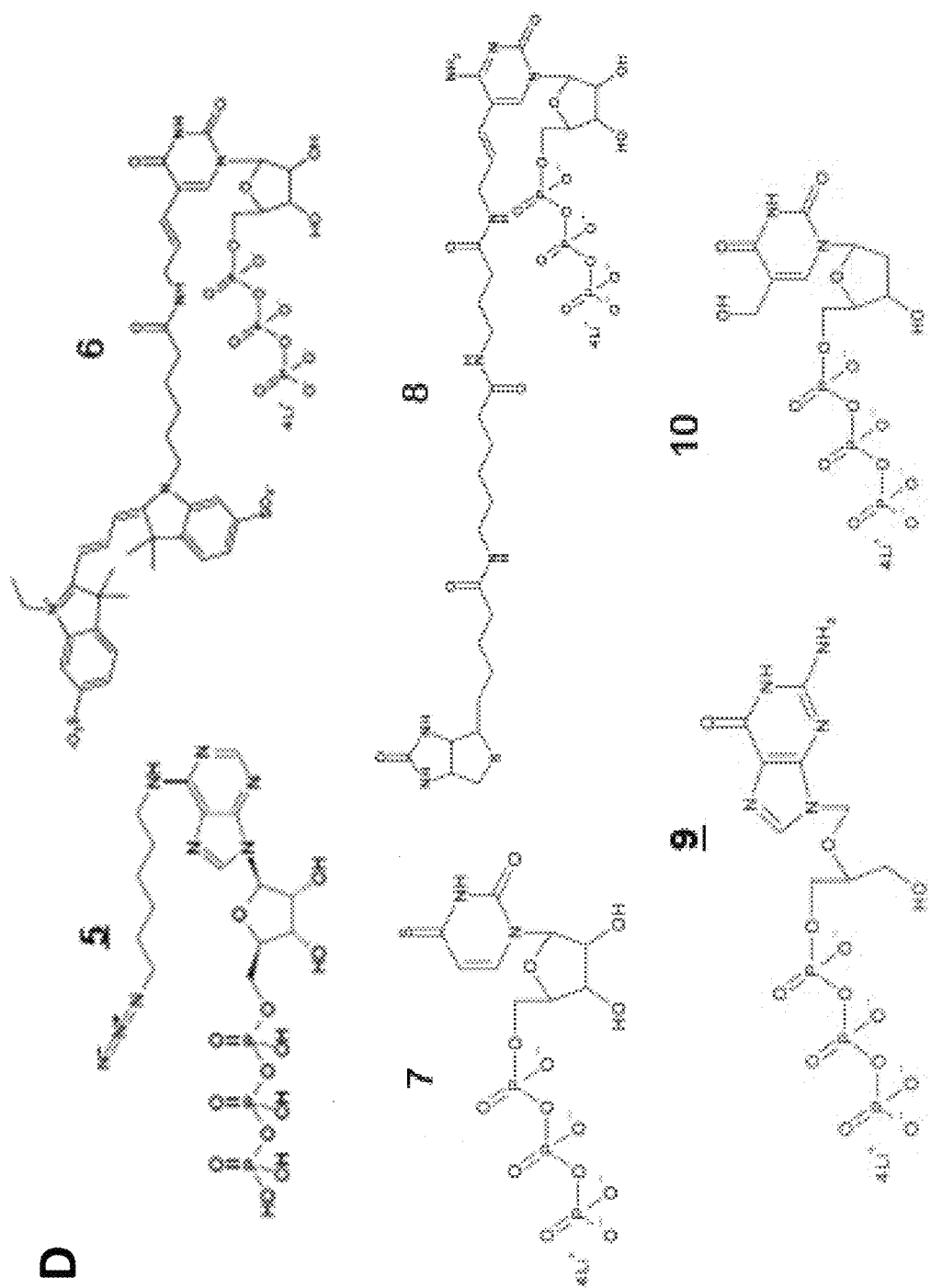

Many biotechnology and biomedical research applications require ssDNA substrates modified with fluorophores or other chemical groups, such as those that enable DNA attachment to solid surfaces. Therefore the ability of Polθ to transfer deoxyribonucleotides and ribonucleotides conjugated with different functional groups to the 3' terminus of ssDNA was examined. Again, using the supplier's recommended assay conditions for TdT, and identical concentrations of Polθ under its optimal conditions, Polθ-$Mn^{2+}$ was more effective in transferring ribonucleotides to ssDNA compared to TdT (FIG. 28B). Although previous studies have shown that Polθ strongly discriminates against ribonucleotides (Hogg et al., 2012), this fidelity mechanism is largely compromised under these conditions used for terminal transferase activity. Again, using the respective optimal conditions for Polθ and TdT at identical concentrations, Pol-$Mn^{2+}$ was more proficient in transferring most modified deoxy-ribonucleotides and ribonucleotides to ssDNA than TdT (FIGS. 28C and 28D). For example, Polθ more efficiently transferred eight out of ten modified nucleotides tested. In some cases, Polθ produced longer extension products than TdT (FIG. 28C). In other cases, Polθ transferred nucleotides that TdT was unable to incorporate (FIG. 28C, black boxes). For instance, Polθ efficiently transferred a nucleotide containing a linker attached to an azide group which is widely used for "click chemistry" applications (FIG. 28C, lane 6). In contrast, TdT failed to transfer this nucleotide altogether (FIG. 28C, lane 17). Moreover, TdT failed to transfer nucleotides containing a modified sugar and a linker attached to Texas Red, whereas these substrates were efficiently incorporated by Polθ (FIG. 28C, nucleotide analogs 4 and 9). These results show that Polθ efficiently transfers ribonucleotides and deoxyribonucleotides containing modifications on their base moieties, such as fluorophores and functional groups including biotin and digoxigenin, as well as nucleotides containing sugar modifications (i.e. ganciclovir mono-phosphate). Considering that Polθ also exhibits translesion synthesis activity, these results may be attributed to its natural ability to accommodate non-canonical nucleotides in its active site (Hogg et al., 2011; Yoon et al., 2014).

Figure 28E:
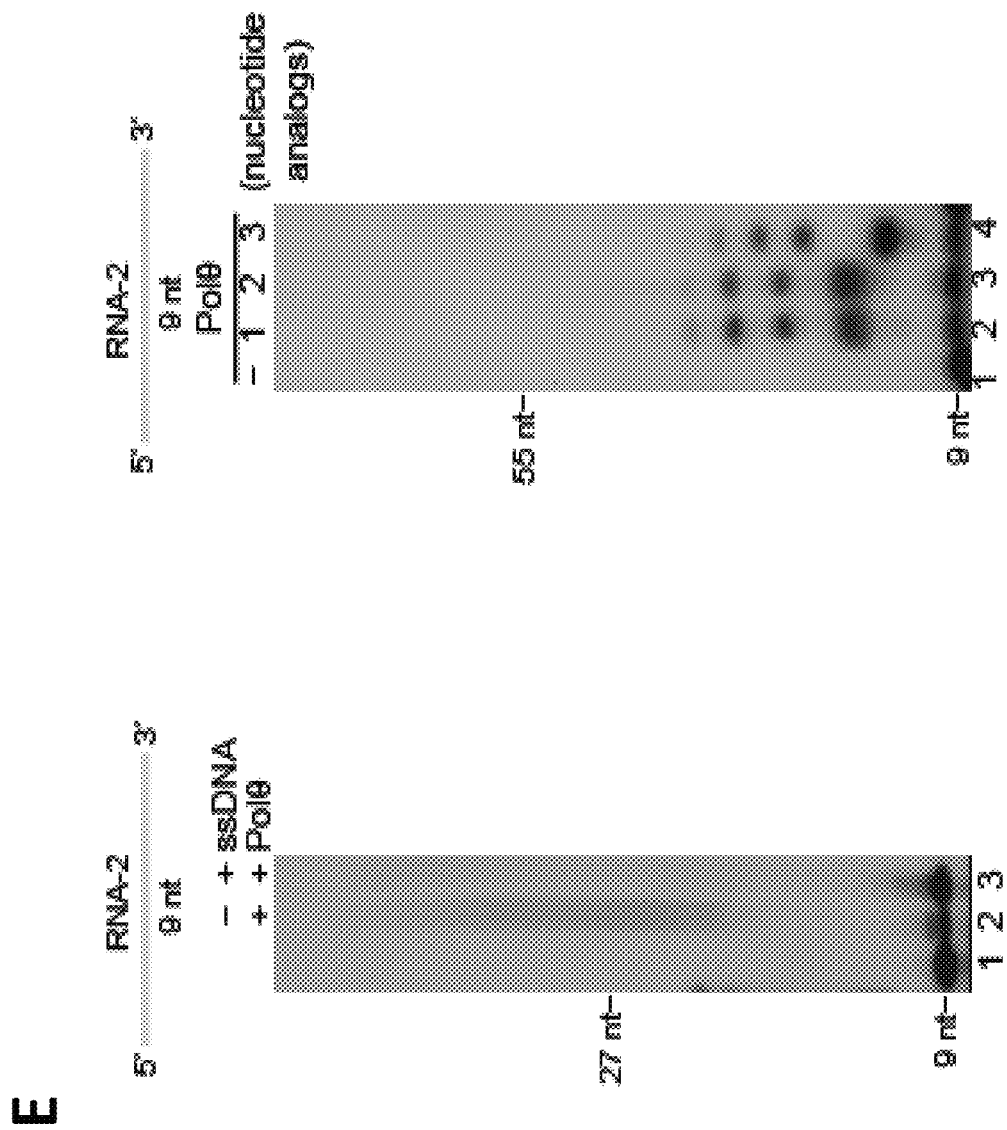

Lastly, whether Polθ exhibits terminal transferase activity on RNA was investigated. Surprisingly, Polθ transferred both canonical and modified nucleotides to RNA (FIG. 28E). Together, the results presented in FIG. 28 characterize Polθ as among the most proficient terminal transferases identified and demonstrate that Polθ is more effective than TdT in modifying nucleic-acid substrates for biomedical research and biotechnology applications.

Mechanisms by which a Single Polymerase can Synthesize DNA

Recent studies have discovered that mammalian Polθ is essential for MMEJ/alt-NHEJ, which promotes chromosome rearrangements and resistance to DNA damaging agents, including those used for chemotherapy (Kent, 2015; Mateos-Gomez et al., 2015; Yousefzadeh et al., 2014). Polθ was previously shown to be essential for alt-EJ in flies and worms (Chan et al., 2010; Koole et al., 2014), demonstrating a conserved role for this polymerase in higher eukaryotes. These cellular studies have shown that two types of insertions, non-templated and templated, are generated at alt-EJ repair junctions which are dependent on Polθ expression (Chan et al., 2010; Koole et al., 2014; Mateos-Gomez et al., 2015; Yousefzadeh et al., 2014). In the case of non-templated insertions, it has been proposed that Polθ promotes random transfer of nucleotides via a putative template-independent terminal transferase activity (Mateos-Gomez et al., 2015). Yet, biochemical studies have shown that Polθ lacks template-independent terminal transferase activity, creating a paradox between cellular and in vitro data (Kent, 2015; Yousefzadeh et al., 2014). In the case of templated insertions, a copy in trans model has been proposed which also has not been proven in vitro (Chan et al., 2010; Koole et al., 2014; Yousefzadeh et al., 2014). The data presented herein elucidates how Polθ generates both templated and non-templated nucleotide insertion mutations during alt-EJ, and characterize the polymerase as a highly robust terminal transferase for biotechnology and biomedical research applications.

First, Polθ exhibits robust template-independent terminal transferase activity in the presence of $Mn^{2+}$. Considering that structural studies show that differential binding of divalent cations within the active site of Polθ slightly alters its local conformation (Zahn et al., 2015), $Mn^{2+}$ binding likely facilitates an active site conformation more favorable for non-templated DNA synthesis. Since Polθ dependent nontemplated nucleotide insertions are commonly associated with alt-EJ in cells, these findings suggest that $Mn^{2+}$ acts as a co-factor of Polθ in vivo. For example, although the concentration of $Mn^{2+}$ is relatively low in cells (~0.2 mM) and is considerably less than $Mg^{2+}$ (~1.0 mM), these concentrations of $Mn^{2+}$ and $Mg^{2+}$ stimulate Polθ template-independent terminal transferase activity by 3-8 fold. Thus, cellular concentrations of $Mn^{2+}$ are likely to activate Polθ template-independent activity. Intriguingly, $Mn^{2+}$ has been shown to act as a necessary co-factor for the MRX nuclease complex and its mammalian counterpart, MRN, which is also essential for alt-EJ due to its role in generating 3' ssDNA overhangs onto which Polθ acts (Cannavo and Cejka, 2014; Trujillo et al., 1998). Thus, various enzymes involved in DNA repair are likely to utilize $Mn^{2+}$ as a cofactor in addition to $Mg^{2+}$.

Surprisingly, the Polθ-$Mn^{2+}$ complex exhibited a higher efficiency of transferring ribonucleotides and most modified nucleotide analogs to the 3' terminus of ssDNA than TdT at identical concentrations. For example, in the presence of ribonucleotides, Polθ-$Mn^{2+}$ generated substantially longer extension products, which demonstrates a lower discrimination against ribonucleotides. Polθ-$Mn^{2+}$ also produced longer extension products than TdT in the presence of most nucleotide analogs, including those that contain large functional groups. Moreover, Pol-$Mn^{2+}$ efficiently transferred certain nucleotide analogs that TdT failed to utilize as substrates. For instance, Pol-$Mn^{2+}$ exclusively transfers a nucleotide conjugated with Texas Red and a nucleotide containing an azide group which is widely used for "click" chemistry applications. Furthermore, Polθ-$Mn^{2+}$ is capable of transferring canonical and modified nucleotides to RNA, albeit with lower efficiency than DNA. Based on these unexpected findings, it is contemplated herein that Polθ will be more useful for modifying nucleic acid substrates for biotechnology, biomedical research and synthetic biology applications. Moreover, since Polθ does not require toxic reaction components like TdT, such as $Co^{2+}$ salts or salts of cacodylic acid, Polθ terminal transferase assays are a safer option for research and biotechnology applications.

The data presented herein raises the question why evolution selected for two robust terminal transferases: Polθ and TdT. It is well known that the primary function of TdT is to generate insertion mutations during NHEJ of V, D and J antibody gene regions, which promotes antibody diversity that is necessary for a strong immune system (Motea and Berdis, 2010). Since a diverse immunological defense is important for survival, a clear selective pressure for TdT existed. In the case of Polθ, it appears that the polymerase has also been selected to generate insertion mutations during end-joining, however, the evolutionary pressure for this particular mechanism is not as clear. For example, although Polθ is essential for alt-EJ, this pathway appears to occur infrequently compared to primary DSB repair processes, such as HR (Mateos-Gomez et al., 2015; Truong et al., 2013). Consistent with this, Polθ is not important for normal cell survival or development. Recent studies of *C. elegans*, however, surprisingly show that Polθ mediated alt-EJ is a primary form of repair in germ cells (van Schendel et al., 2015). Furthermore, it was shown that Polθ mediated alt-EJ promotes a deletion and insertion (indel) signature in propogated laboratory strains that is similar to indels found in natural isolates (van Schendel et al., 2015). These studies therefore suggest that Polθ is important for generating genetic diversity. Interestingly, human Polθ is highly expressed in testis, suggesting the polymerase might also play a role in facilitating genetic diversity in mammals (Seki et al., 2003).

Considering that alt-EJ also promotes replication repair as a backup to HR, Polθ likely benefits cell survival at the expense of indels when lethal DSBs fail to be repaired by the primary HR pathway (Truong et al., 2013). For example, Polθ mediated alt-EJ in *C. elegans* was shown to facilitate replication repair at stable G4 structures which may pose problems for the HR machinery and therefore potentially require an alternative and more accommodating error-prone form of repair (Koole et al., 2014). Polθ has also been shown to suppress large genetic deletions in *C. elegans*, which demonstrates an obvious benefit for the polymerase (Koole et al., 2014). Yet, whether these various functions of Polθ are conserved in mammals awaits further research.

These studies reveal that Polθ generates nucleotide insertions by oscillating between multiple mechanisms, which portrays a promiscuous enzyme that readily extends ssDNA by almost any means in order to catalyze end-joining products that frequently contain insertion mutations. For example, it was observed that Polθ generates nucleotide insertions during alt-EJ in vitro by spontaneously switching between three distinct modes of terminal transferase activity: non-templated extension, templated extension in cis, and templated extension in trans. Importantly, the characteristics of these insertions are nearly identical to those generated by Polθ mediated alt-EJ in cells, which indicates that Polθ also switches between these three mechanisms of terminal transferase activity in vivo. The ability of a polymerase to spontaneously switch between three distinct modes of DNA synthesis has not been demonstrated. Thus, this data reveal an unprecedented set of mechanisms by which a single polymerase can synthesize DNA, presumably for generating genetic diversity and as a last resort for repairing lethal DSBs at the expense of mutations.

Example 4: Polymerase θ Exhibits Terminal Transferase Activity

Figure 29:
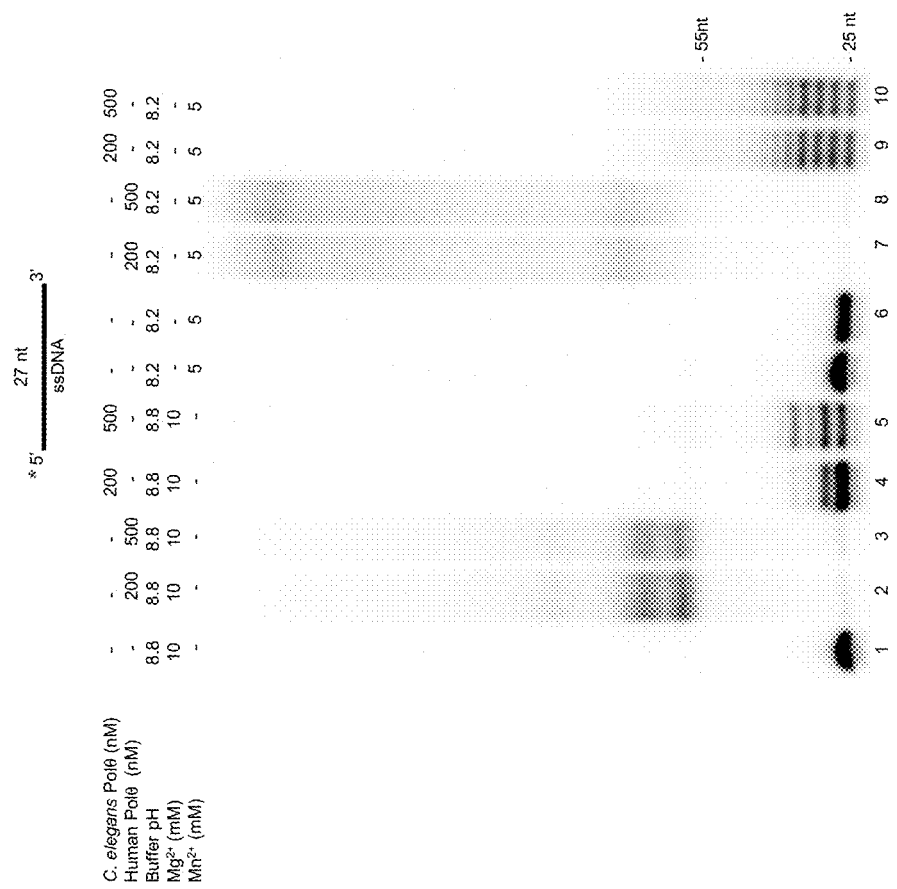
FIG. 29 depicts experimental results demonstrating that C. elegans Polθ exhibits terminal transferase activity. Shown is a non-denaturing gel demonstrating human Polθ and C. elegans Polθ extension of the indicated ssDNA in the presence of all four dNTPs and the indicated divalent cation and buffer pH.

FIG. 29 demonstrates the ability of invertebrate Polθ to modify the 3' ends of ssDNA. The polymerase domain of invertebrate and vertebrate Polθ differ within their respective insertion domains with regards to sequence identity. Invertebrate Polθ contains smaller insertion loops compared to vertebrate Polθ. Otherwise, the polymerase domains of these polymerases are very similar in sequence. The polymerase domain of *C. elegans* Polθ was purified and its terminal transferase activity was compared to human Polθ in FIG. 29. The results show that *C. elegans* Polθ also exhibits terminal transferase activity that is stimulated by $Mn^{2+}$. Thus, both vertebrate and invertebrate Polθ exhibit robust terminal transferase activity and can be used to modify the 3' terminus of nucleic acids with various types of nucleotides and nucleotide analogs for basic and applied research, and for commercial biotechnology and synthetic biology applications.

Figure 30:
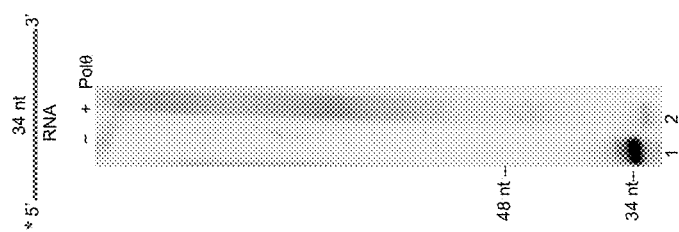
FIG. 30 depicts experimental results demonstrating that human Polθ exhibits efficient terminal transferase activity on long RNA. Shown is a non-denaturing gel showing human Polθ extension of the indicated RNA in the presence of all four dNTPs in 8.2 pH buffer containing 5 mM $Mn^{2+}$.

Next, it was examined whether Polθ is capable of efficient extension of RNA. FIG. 30 demonstrates that human Polθ efficiently transfers dNMPs to the 3' terminus of a relatively long RNA substrate 34 nt in length under optimal conditions with $Mn^{2+}$ present in the reaction buffer.

Figure 31:
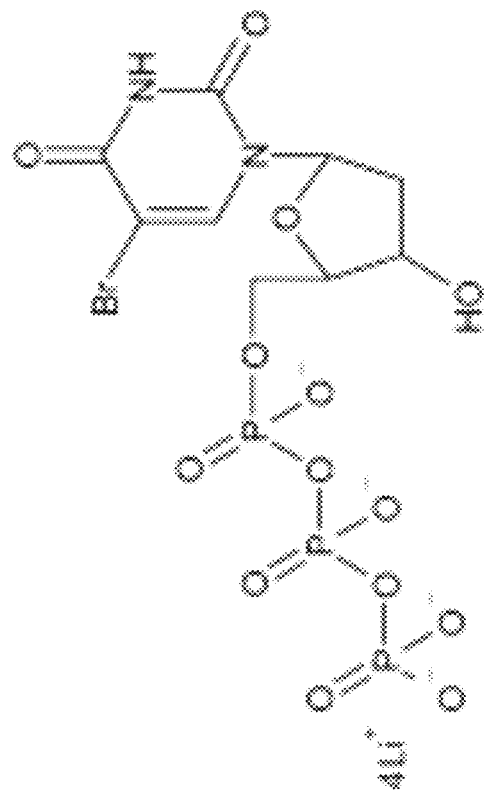
FIG. 31 depicts experimental results demonstrating that human Polθ efficiently transfers 5-bromo-2'-deoxyuridine-5'-monophosphate (5-bromo-dUMP) to ssDNA. Shown is a non-denaturing gel showing human Polθ extension of the indicated ssDNA in the presence of all four dNTPs (lane 2) or 5-bromo-2'-deoxyuridine-5'-triphosphate (lane 3) in 8.2 pH buffer containing 5 mM $Mn^{2+}$. Structure of 5-bromo-2'-deoxyuridine-5'-triphosphate (right).
Figure 31:
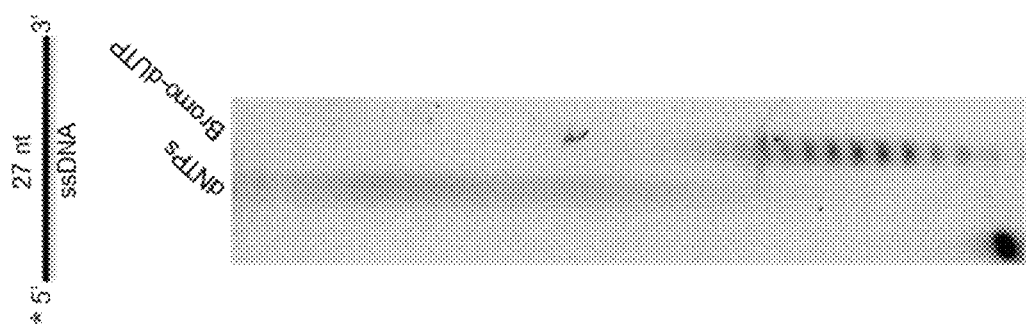

Several biotechnology and research applications require modification of DNA with the nucleotide analog 5-bromo-2'-deoxyuridine-monophosphate. In FIG. 31 it is shown that human Polθ efficiently transfers multiple 5-bromo-2'-deoxyuridine-monophosphates to the 3' terminus of ssDNA under optimal buffer conditions with $Mn^{2+}$ present in the reaction buffer.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A method of modifying a 3' terminal end of a nucleic acid with a substrate, the method comprising:
   forming an in vitro mixture comprising an A family polymerase consisting essentially of SEQ ID NO 1, a substrate, a nucleic acid comprising a single-stranded 3' end or overhang, and a reaction solution, wherein the reaction solution comprises at least one divalent metal;
   incubating the mixture, wherein the A family polymerase attaches the substrate to the single-stranded 3' end or overhang of the nucleic acid in vitro by a template-independent terminal transferase activity thereby forming a 3'-terminal end modified nucleic acid; and
   isolating a 3'-terminal end modified nucleic acid.

2. The method of claim 1, wherein the nucleic acid is selected from the group consisting of single stranded DNA (ssDNA), partial ssDNA, RNA and telomeric ssDNA.

3. The method of claim 1, wherein the substrate is selected from the group consisting of dATP, dGTP, dCTP, dATP, dUTP, ATP, CTP, UTP, a modified nucleotide, a labeled dNTP, and any combination thereof.

4. The method of claim 3, wherein the labeled dNTP is selected from cy3-dUTP, Digoxigenin-11-dUTP, Biotin-16AA-dUTP, Texas Red-5-dCTP, Cyanine 3-AA-UTP, 4-Thio-UTP, Biotin-16-AACTP, Ganciclovir Triphosphate, N6-(6-Azido)hexyl-adenosine-5'-triphosphate, and 5-Hydroxymethyl-2'-deoxyuridine-5'-Triphosphate.

5. The method of claim 1, wherein the divalent metal is selected from the group consisting of manganese ($Mn^{2+}$), cobalt ($Co^{2+}$), and a combination thereof.

6. The method of claim 1, wherein the divalent metal is at a concentration of about 1 mM to about 50 mM.

7. The method of claim 6, wherein the divalent metal is at a concentration of about 5 mM.

8. The method of claim 1, wherein the reaction solution further comprises glycerol, a non-ionic detergent, and a buffer.

9. The method of claim 8, wherein a concentration of the glycerol in the reaction solution is less than or equal to 20%.

10. The method of claim 9, wherein the concentration of glycerol in the reaction solution is 10%.

11. The method of claim 8, wherein the non-ionic detergent is NP-40.

12. The method of claim 8, wherein a concentration of the non-ionic detergent is less than 1%.

13. The method of claim 12, wherein the concentration of the non-ionic detergent is 0.1%.

14. The method of claim 8, wherein the buffer is MES/TRIS and wherein MES/TRIS is at a concentration of about 20 mM to about 100 mM.

15. The method of claim 8, wherein the pH of the buffer is 6.3-6.8.

16. The method of claim 15, wherein the pH of the buffer is 8.2.

17. The method of claim 1, wherein the incubating the mixture is incubating the mixture for at least 2 hours.

18. The method of claim 1, where the incubating the mixture is incubating the mixture at 25° C.-42° C.

19. The method of claim 18, where the incubating the mixture is incubating the mixture at 42° C.

20. A kit for modifying a 3' terminal end of a nucleic acid with a substrate, the kit comprising an A-family polymerase consisting essentially of SEQ ID NO 1 operable to attach a substrate to a single-stranded 3' end or overhang of nucleic acid in vitro by template-independent terminal transferase activity in the presence of a divalent metal and a reaction solution comprising the divalent metal.

21. The kit of claim 20, the kit further comprising the substrate.

22. The kit of claim 20, wherein the divalent metal is manganese ($Mn^{2+}$) or cobalt ($Co^{2+}$).

23. The kit of claim 20, wherein the reaction solution comprises 5 mM $Mn^{2+}$, 20 mM Tris HCl pH 8.2, 10% glycerol, 0.01% NP-40 and 0.1 mg/mL BSA.

24. A method of de novo synthesis of nucleic acids, the method comprising:
   forming an in vitro mixture comprising an A family polymerase consisting essentially of SEQ ID NO 1, at least one nucleobase, a nucleic acid comprising a single-stranded 3' end or overhang, and a reaction solution, wherein the reaction solution comprises at least one divalent metal;
   incubating the mixture, wherein the A family polymerase attaches the nucleobase to the single-stranded 3' end or overhang of the nucleic acid in vitro by a template-independent terminal transferase activity thereby forming an extended nucleic acid; and
   isolating the extended nucleic acid.

25. The method of claim 24, wherein the at least one nucleobase is an NTP, a dNTP, a fluorescently labeled dNTP, or a 3'-O-blocked reversible terminator analog of an NTP or dNTP.

26. The method of claim 24, wherein the at least one divalent metal is $Mn^{2+}$.

27. The method of claim 1, wherein the substrate is selected from the group consisting of a 3'-O-blocked reversible terminator analog of dATP, dGTP, dCTP, dUTP, ATP, CTP, UTP, and GTP.

* * * * *